(12) United States Patent
Steenstrup et al.

(10) Patent No.: US 7,696,318 B2
(45) Date of Patent: Apr. 13, 2010

(54) HOST CELL PROTEIN KNOCK-OUT CELLS FOR PRODUCTION OF THERAPEUTIC PROTEINS

(75) Inventors: Thomas Dock Steenstrup, Gentofte (DK); Peder Lisby Norby, Copenhagen O (DK)

(73) Assignee: Novo Nordisk Health Care AG, Zurich (CH)

( * ) Notice: Subject to any disclaimer, the term of this patent is extended or adjusted under 35 U.S.C. 154(b) by 0 days.

(21) Appl. No.: 11/995,109

(22) PCT Filed: Jul. 13, 2006

(86) PCT No.: PCT/EP2006/064220

§ 371 (c)(1),
(2), (4) Date: Jun. 24, 2008

(87) PCT Pub. No.: WO2007/006808

PCT Pub. Date: Jan. 18, 2007

(65) Prior Publication Data

US 2008/0299611 A1     Dec. 4, 2008

Related U.S. Application Data

(60) Provisional application No. 60/706,369, filed on Aug. 8, 2005.

(30) Foreign Application Priority Data

Jul. 13, 2005    (EP) .................................. 05106401

(51) Int. Cl.
*A61K 35/15*    (2006.01)
*A61K 35/14*    (2006.01)
*C07K 1/00*    (2006.01)

(52) U.S. Cl. .................. 530/380; 530/350; 530/381

(58) Field of Classification Search .................. 435/6, 435/69.1; 530/350, 380, 381; 536/23.5
See application file for complete search history.

(56) References Cited

FOREIGN PATENT DOCUMENTS

| EP | 0658168 | 11/2000 |
|---|---|---|
| WO | WO 98/12300 | 3/1998 |
| WO | WO 00/38517 | 7/2000 |
| WO | WO 2004/092735 | 10/2004 |
| WO | WO 2005/028630 | 3/2005 |
| WO | WO 2005/040187 | 5/2005 |
| WO | WO 2006/067230 | 6/2006 |

OTHER PUBLICATIONS

Jurlander, B. et al., "Recombinant Activated Factor VII (rFVIIa): Characterization, Manufacturing, and Clinical Development", Seminars in Thrombosis and Hemostasis, 2001, vol. 27, No. 4, pp. 373-383.

Mori, K. et al., "Engineering Chinese Hamster Ovary Cells to Maximize Effector Function of Produced Antibodies Using FUT8 siRNA", Biotechnology and Bioengineering, 2004, vol. 88, No. 7, pp. 901-908.

Yamane-Ohnuki, N. et al., "Establishment of FUT8 Knockout Chinese Hamster Ovary Cells : An Ideal Host Cell Line for Producing Completely Defucosylated Antibodies with Enhanced Antibody-Dependent Cellular Cytotoxicity", Biotechnology and Bioengineering, 2004, vol. 87, No. 5, pp. 614-622.

Sooy, K. et al., "Transcriptional Repression of the Rat Osteocalcin Gene by δEF1", Endocrinology, 2002, vol. 143, No. 9, pp. 3370-3375.

Hall, M. O. et al., "Both protein S and Gas6 stimulate outer segment phagocytosis by cultured rat retinal pigment epithelial cells", Experimental Eye Research, 2005, vol. 81, No. 5, pp. 581-591.

Chu, M.D. et al., XP-002361937, EMBL Data Library, 1993.

Josic, D. et al., "Preparation of vitamin K-dependent proteins, such as clotting factors II, VII, IX and X and clotting inhibitor Protein C", Journal of Chromatography, 2003, vol. 790, vol. 1-2, pp. 183-197.

Angelillo-Scherrer, A. et al., "Deficiency or inhibition of Gas6 causes platelet dysfunction and protects mice against thrombosis", Nature Medicine, 2001, vol. 7, No. 2, pp. 215-221.

Yan, S.B., "Review of Conformation-specific Affinity Purification Methods for Plasma Vitamin K-dependent Proteins", Journal of Molecular Recognition, 1996, vol. 9, pp. 211-218.

Furie, B. et al., "Antibodies Directed Against a γ-Carboxyglutamic Acid-rich Region of Bovine Prothrombin", The Journal of Biological Chemistry, 1978, vol. 253, No. 24, pp. 8980-8987.

Nelsestuen, G.L. et al., "Role of γ-Carboxyglutamic Acid", Journal of Biological Chemistry, 1976, vol. 251, No. 22, pp. 6886-6893.

Yan, S.C.B et al., "Characterization and Novel Purification of Recombinant Human Protein C from Three Mammalian Cell Lines", Biotechnology, 1990, vol. 8, pp. 655-661.

Brown, M.A. et al., "Identification and Purification of Vitamin K-dependent Proteins and Peptides with Monoclonal Antibodies Specific for γ-Carboxyglutamyl (Gla) Residues", Journal of Biological Chemistry, 2000, vol. 275, No. 26, pp. 19795-19802.

Furie, B. et al., "Conformation-specific Antibodies as Probes of the γ-Carboxyglutamic Acid-rich Region of Bovine Prothrombin", Journal of Biological Chemistry, 1979, vol. 254, No. 19, pp. 9766-9771.

Church, W.R. et al., "A Conserved Epitope on Several Human Vitamin K-dependent Proteins", Journal of Biological Chemistry, 1988, vol. 263, No. 13, pp. 6259-6267.

Bjoern and Thim et al., Activation of Coagulation Factor VII to VIIa, Research Disclosure, 1986, vol. 29, No. 60.

*Primary Examiner*—Jane Zara
(74) *Attorney, Agent, or Firm*—Shelby J. Walker

(57) ABSTRACT

The present invention relates to methods and means for making Vitamin K-dependent protein compositions which are devoid or substantially devoid of protein contaminants. In particular, methods and means useful for the reduction or elimination of protein contaminants also being Vitamin K-dependent proteins are described.

1 Claim, 6 Drawing Sheets

RansiRNA vector

A)

B)

HOST CELL PROTEIN KNOCK-OUT CELLS FOR PRODUCTION OF THERAPEUTIC PROTEINS

CROSS-REFERENCE TO RELATED APPLICATIONS

This application is a 35 U.S.C. § 371 national stage application of International Patent Application PCT/EP2006/064220 (published as WO 2007/006808 A1), filed Jul. 13, 2006, which claimed priority of European Patent Application 05106401.2, filed Jul. 13, 2005; this application further claims priority under 35 U.S.C. § 119 of U.S. Provisional Application 60/706,369, filed Aug. 8, 2005.

FIELD OF THE INVENTION

The present invention relates to methods for producing compositions comprising Vitamin K-dependent protein having a very low or negligible content of protein contaminants and to compositions derived from such methods. Such methods may either be used alone or in combination with other methods for the purpose of reducing the relative content of protein contaminants. The present invention is particularly relevant in the preparation of compositions of coagulation factors selected from Thrombin polypeptides (FII/FIIa), Factor X polypeptides (FX/FXa), Factor IX polypeptides FIX/FIXa), Factor VII polypeptides (FVII/FVIIa), and the anticoagulant Protein C, in particular Factor VII polypeptides.

BACKGROUND OF THE INVENTION

In the production of recombinant proteins from cultures of microorganisms or cell lines, the final production step is the recovery and optionally the concentration of the product of interest. Culture media in which the cells have been grown and which contain secreted proteins, and, in particular, cell lysates containing intracellular proteins of interest also contain, to a greater or lesser extent, other proteins produced by the cells, apart from other contaminants, such as media components, nucleic acids and the like. In order to obtain a purified protein product, it is therefore necessary to separate the protein of interest from other proteins and polypeptides and other impurities in the crude material containing the protein of interest. It is however, often difficult to remove protein contaminants comprising domains of the same nature as the polypeptide of interest.

Vitamin K-dependent proteins are distinguished from other proteins by sharing a common structural feature in their amino terminal part of the molecule. The N-terminal of these proteins, also referred to as the Gla-domain, is rich in the unusual amino acid γ-carboxy glutamic acid which is synthesized from glutamate in a Vitamin K dependent reaction catalysed by the enzyme γ-glutamyl carboxylase. Because of the presence of about 9 to 12 Gla residues, the Gla-domain is characterised by being capable of binding divalent cations such as $Ca^{2+}$. Upon binding of metal ions, these proteins undergo conformational changes which can be measured by several techniques such as circular dichroism and fluorescence emission.

The discovery of metal induced conformational changes of Gla-containing proteins (Nelsestuen et. al., J. Biol. Chem. 1976; 251, 6886-6893) together with identification of conformation specific polyclonal antibodies (Furie et al., J. Biol. Chem. 1978; 253, 8980-8987) opened the way for the introduction of conformation specific immunoaffinity chromatography. These antibodies could recognise and bind the Gla-domain in the presence of $Ca^{2+}$ ions but released the protein upon removal of $Ca^{2+}$ ions using a $Ca^{2+}$ chelator such as EDTA or citrate.

In 1980's conformation specific pseudoaffinity chromatography was developed making use of the unique property of Gla containing proteins to undergo metal induced changes in conformation. Pseudoaffinity chromatography differs from the conventional affinity chromatography in that there is no immobilized affinity ligand involved and it is performed on a conventional chromatographic matrix (Yan S. B., J. Mol. Recog. 1996; 9, 211-218). The Gla protein can be adsorbed to an anion exchange material by eliminating divalent metal ions. Subsequently, elution is performed by adding $Ca^{2+}$ to the elution buffer.

In 1986, Bjørn and Thim reported purification of rFVII on an anion exchange material taking advantage of $Ca^{2+}$-binding property of Gla-domain of FVII (Bjørn S, and Thim L., Research Disclosure, 1986, 26960-26962.). Adsorption was achieved in a buffer without $Ca^{2+}$ and elution of FVII was possible using a $Ca^{2+}$ containing buffer with low ionic strength and under mild conditions. Yan et al. have used the same principle for the purification of recombinant human Protein C (Yan S. B. et al., Bio/technology. 1990; 8, 655-661).

Brown et al. (Brown et al., J. Biol. Chem. 2000; 275, 19795-19802.) have reported monoclonal antibodies specific for Gla residues. These antibodies could recognize all of the Gla proteins tested: Factor VII, Factor IX, Factor II, Protein C, Protein S, GAS-6, bone matrix Gla protein, conantokin G. Several conformational specific antibodies raised against one Gla protein show cross reactivity with other Gla proteins (Furie B. and Furie B., J. Biol. Chem. 1979; 254, 9766-9771; Church et al., J. Biol. Chem. 1988; 263, 6259-6267).

While the presence of the Gla-domain provides an advantage for separation of Gla containing proteins from other proteins, the inventors of present invention observed that similar properties and behaviour of the Gla containing proteins makes it difficult to separate them from each other.

Proteins with a Gla-domain comprise the following proteins: GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.

The need for efficiently separating a Vitamin K-dependent protein of interest, such as a Gla-domain containing polypeptide of interest, from protein contaminants is a particularly relevant issue when dealing with the purification of such polypeptides produced in cell cultures, because the host cell may produce significant amounts of protein contaminants that may cause undesirable immunogenic reactions upon use of the polypeptide.

SUMMARY OF THE INVENTION

The present invention relates in a broad aspect to the generation of compositions comprising a Vitamin K-dependent protein of interest which is devoid or substantially devoid of at least one protein contaminant expressed by the host cell.

Thus in a first aspect the present invention relates to a host cell expressing a Vitamin K-dependent protein of interest, the host cell being modified to express a substantially lower amount of at least one protein contaminant expressed endogenous by the host cell in the absence of the modification. In one embodiment the host cell is transfected with a polynucleotide construct to encode the Vitamin K-dependent protein of interest.

The term "modified" as used herein refers to a cell that has been engineered by any man-made molecular or cell biology techniques or process useful in the industry.

In a second aspect the present invention relates to a method for producing a host cell according to the invention, the method comprising the following steps in any order:

a) optionally transfecting the host cell with a polynucleotide construct encoding a Vitamin K-dependent protein of interest; and b) modifying the host cell to express a substantially lower amount of at least one protein contaminant expressed endogenous by the host cell in the absence of the modification.

In a further aspect the present invention relates to a method for producing a composition comprising a Vitamin K-dependent protein of interest with a substantially lower amount of at least one protein contaminant expressed endogenous by the host cell in the absence of modification, the method comprising the steps of growing a host cell expressing a Vitamin K-dependent protein of interest, the host cell being modified to express a substantially lower amount of at least one protein contaminant expressed endogenous by the host cell in the absence of the modification, in a growth medium and harvesting the growth medium comprising the Vitamin K-dependent protein of interest.

In a further aspect the present invention relates to a method for producing a composition comprising a Vitamin K-dependent protein of interest with a substantially lower amount of at least one protein contaminant expressed endogenous by the host cell in the absence of modification, the method comprising the steps of:

a) producing a host cell according to the invention; and b) growing the host cell in a growth medium and harvesting the growth medium comprising the Vitamin K-dependent protein of interest.

In a further aspect the present invention relates to a composition produced by a method for producing a composition comprising a Vitamin K-dependent protein of interest with a substantially lower amount of at least one protein contaminant expressed endogenous by the host cell in the absence of modification, the method comprising the steps of growing a host cell expressing a Vitamin K-dependent protein of interest, the host cell being modified to express a substantially lower amount of at least one protein contaminant expressed endogenous by the host cell in the absence of the modification, in a growth medium and harvesting the growth medium comprising the Vitamin K-dependent protein of interest.

In a further aspect the invention relates to modified cells expressing a Vitamin K-dependent protein of interest useful for generating compositions comprising a Vitamin K-dependent protein of interest, devoid or substantially devoid of protein contaminants expressed by the host cell.

In a further aspect the invention relates to methods for reducing or eliminating the content of at least one protein contaminant in a composition comprising a Vitamin K-dependent protein of interest wherein at least one protein contaminant expressed by the host cell is inhibited.

In a further aspect the invention relates to new nucleic acid sequences encoding protein S in CHO cell.

In a further aspect the invention relates to a new amino acid sequence of protein S in CHO cell.

The vector is composed of two polymerase III promoters transcribing the siRNA template in each direction. The two RNA transcripts are complementary and anneal to form the final siRNA molecule. The vector contains a hygromycin resistance gene which makes it possible to select for stable cell clones.

Figure 1:
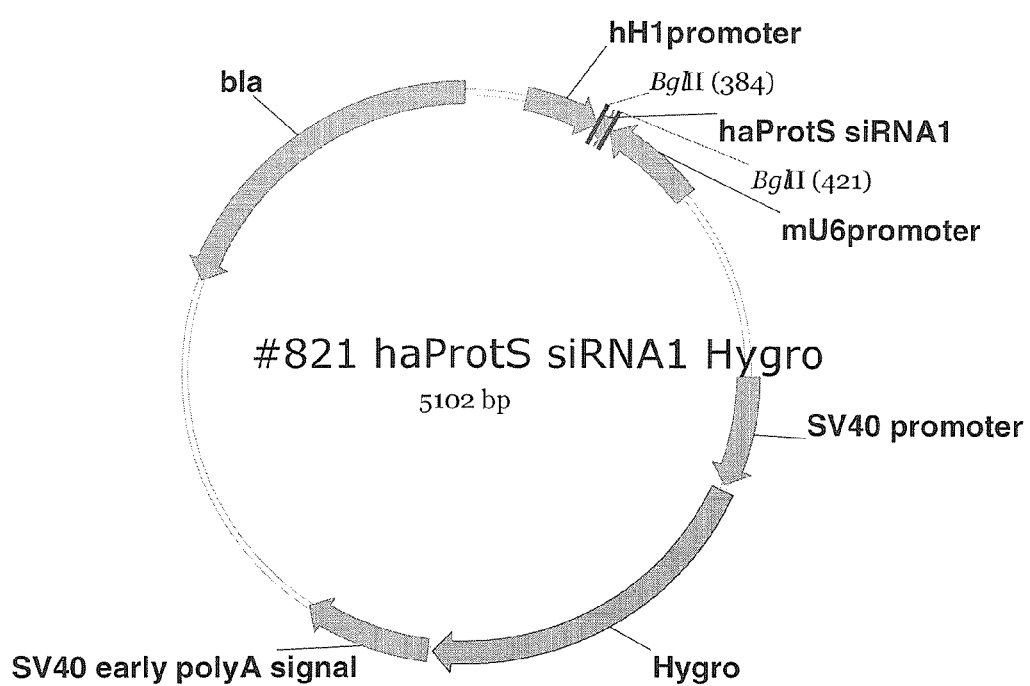
FIG. 1 illustrates the RansiRNA vector.
Figure 2:
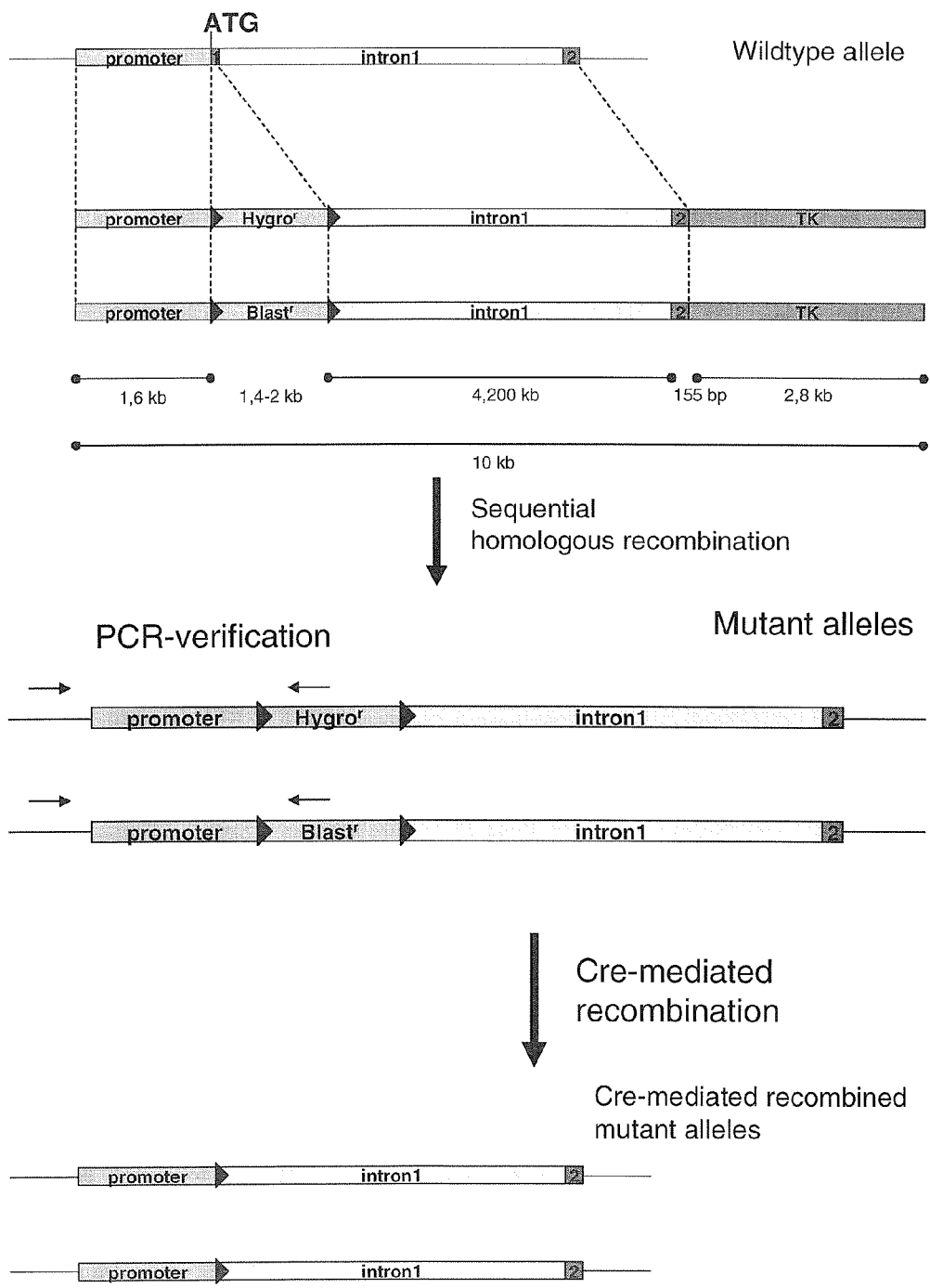

FIG. 2 illustrates steps in the Gene targeting method.

In the CHO Protein S gene targeting construct the coding part of exon 1 has been exchanged by a hygromycin or a blasticidin resistance gene for positive selection. Furthermore, the TK gene is inserted next to exon 2 for negative selection. Two cre/lox sites are flanking the resistance gene. Following homologous recombination the cell population can be screened using primers specific to promoter region outside the construct and to the resistance gene in the construct. Once the alleles have been knocked-out for wildtype Protein S, the cells may be transfected by an expression plasmids containing Cre recombinase. The Cre recombinase will recombinate at the cre/lox sites and resistance genes are deleted from the cell genome.

Figure 3:
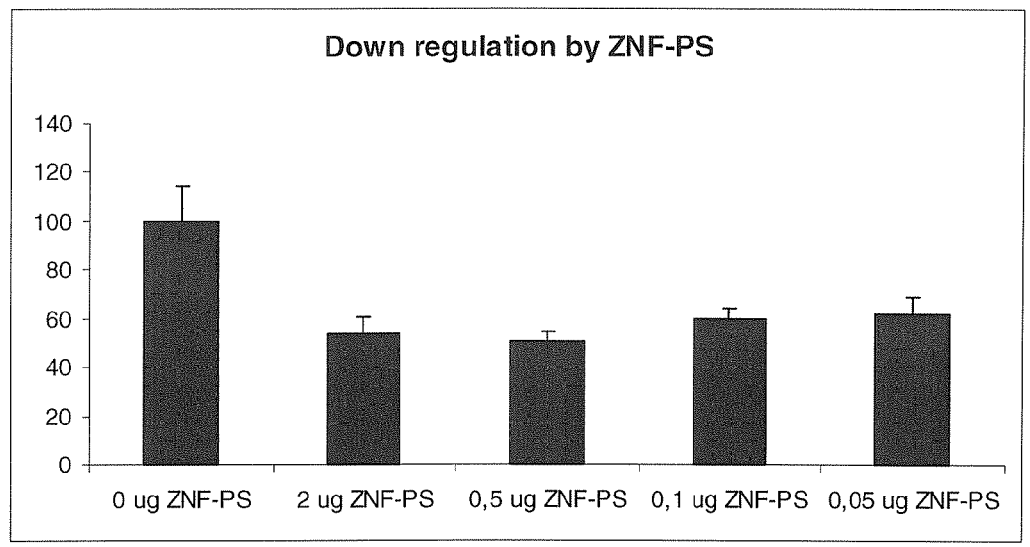
Figure 3:
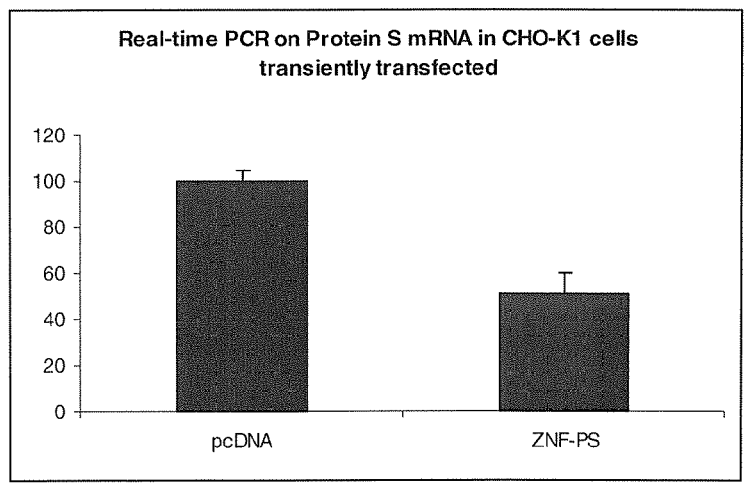

FIG. 3 illustrates down regulation of the Protein S gene in CHO-K1 cells using the synthetic made gene ZNF-PS.

FIG. 3a: The synthetic gene ZNF-PS downregulates Protein S transcription in CHO-K1 cells, determined by luciferase reporter assay. The figure shows luciferase readout from a reporter containing the Protein S promoter. The pRL-CMV (Promega, Madison) vector was used as control for transfection efficiency. ZNF-PS down regulates Protein S promoter activity by 50% in a transient transfection.

FIG. 3b: The synthetic gene ZNF-PS downregulates Protein S transcription in CHO-K1 cells, determined by real-time PCR on Protein S mRNA. The figure illustrates a realtime PCR quantitation of the Protein S mRNA in CHO-K1 transiently transfected with ZNF-PS. The pEGFP (Clontech, Mountain View) vector was used as control for transfection efficiency. In this experiment ZNF-PS also down regulates Protein S 50%.

Figure 4:
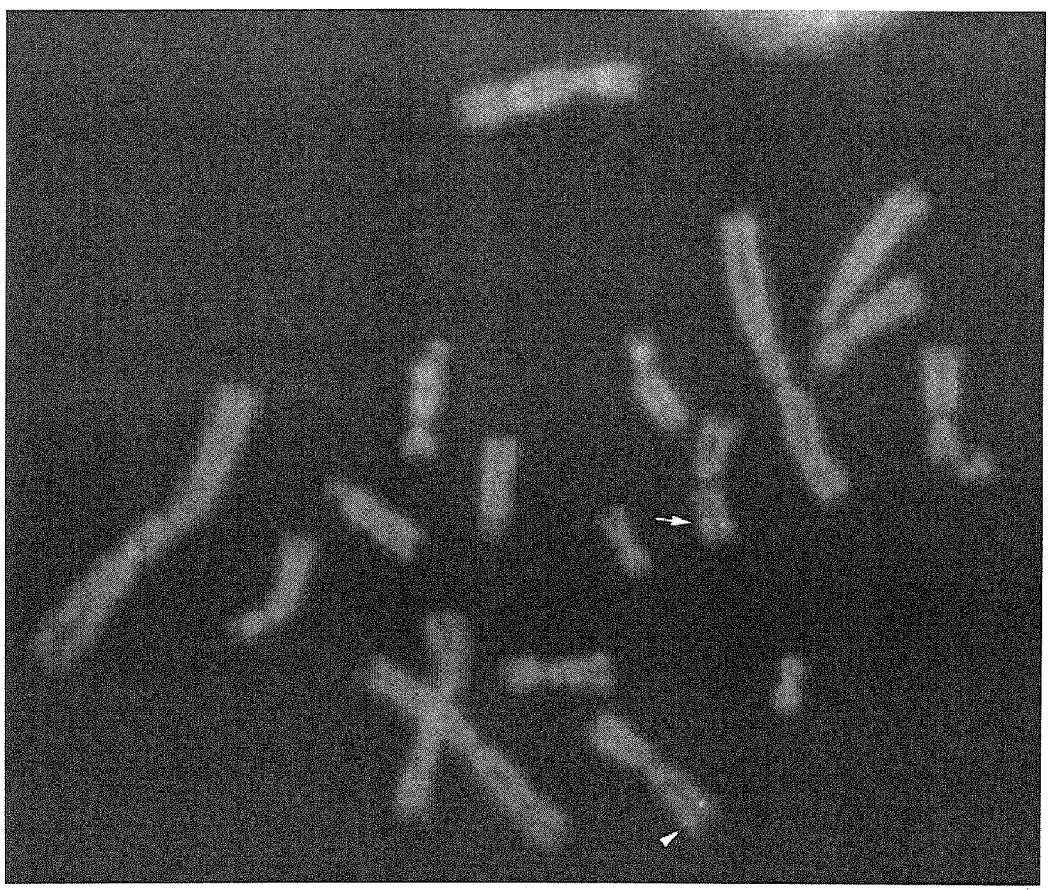

FIG. 4: The Protein S gene is localized onto two different chromosomes in the same metaphase of CHO-K1 cells. The figure illustrates Protein S gene localization in the CHO-K1 genome. FISH was per-formed on CHO-K1 chromosomes using Protein intron 1 as probe.

Figure 5:
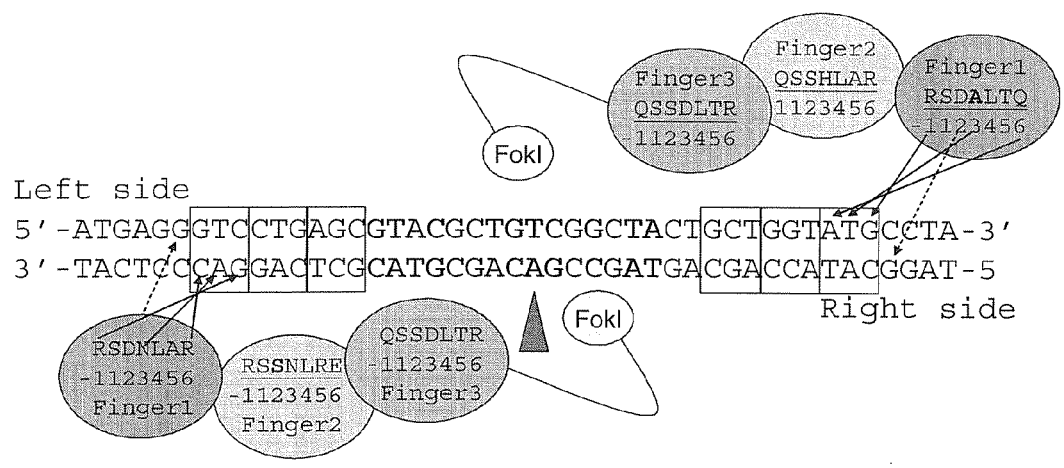

FIG. 5: Two zinc finger proteins fused to nucleases bind inside exon1 of the CHO Protein S gene. The figure illustrates DNA binding specificity of two zinc finger proteins fused to Fok I nuclease.

The left zinc finger protein is expected to bind to 5'-GTC-CTGAGC-3' (upper strand) and the right zinc finger will bind to 5'-GCTGGTATG-3' (upper strand) both sequence element is harbored by Protein S exon 1. The two zinc finger are either fused to Fok I og Sts I nucleases, the nucleases will homodimerize and perform the cleavage of the DNA strands.

Figure 6:
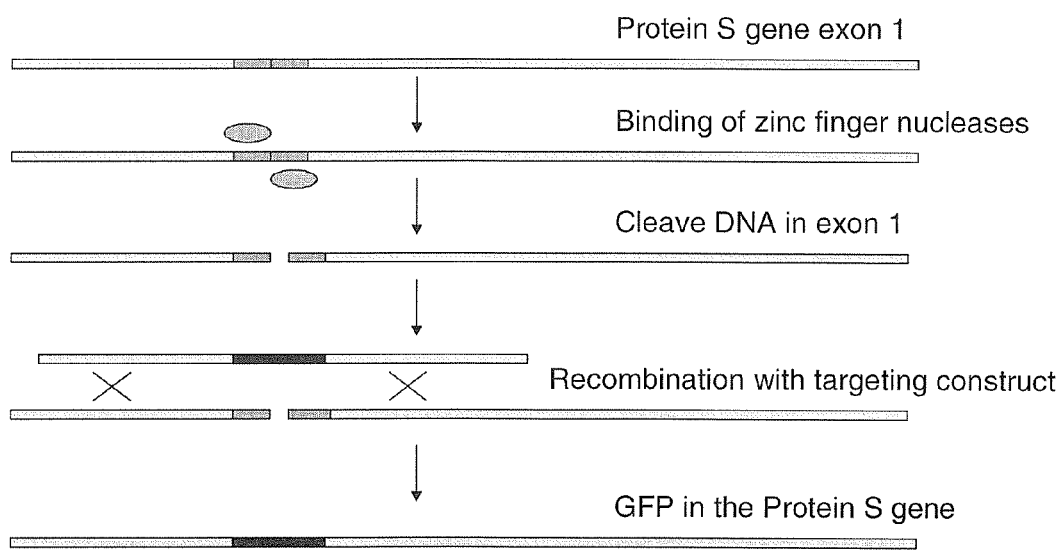

FIG. 6: Gene targeting by homologous recombination enhanced by zinc finger nuclease cleavage. The figure illustrates the step in homologous recombination enhanced by zinc finger nucleases.

The zinc finger nucleases will bind their specific binding sites within Protein S exon 1 and cleave the DNA strands. The gene targeting vector transfected along with the nucleases contains a large fragment identical to the Protein S gene, on each side of the EGFP gene. Recombination occurs between the Protein S gene and targeting vector. Recombinant cells can be sorted due to EGFP expression.

DETAILED DESCRIPTION OF THE INVENTION

The present invention relates to a host cell for the production of recombinant proteins, wherein this host cell is modified to express a substantially lower amount of at least one protein contaminant expressed endogenous by the host cell in the absence of the modification.

It will be understood that any method or technique for reducing expression of the contaminating protein may be used. The examples of such methods including siRNA targeting, targeted gene knock-out, transfection with a transcriptional factor, and site-specific cleavage of the DNA strands encoding protein contaminants are not to be construed limiting in any way. In principle, any molecular biology, cell biology, or selection method may be used to reduce the expression level of a particular protein contaminant. The present invention is particular useful in the situation, where the Vitamin K-dependent protein of interest is very closely related with one or more protein contaminants, such as when the protein contaminant is a second vitamin K-dependent protein. Due to the close relationship between a vitamin K-dependent protein of interest and a protein contaminant, which is a second vitamin K-dependent protein, such protein contaminant may be very difficult remove by purification methods.

The present invention further relates to compositions comprising Vitamin K-dependent proteins of interest devoid or substantially devoid of at least one protein contaminant expressed by a host cell.

In one embodiment of the invention, the Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin. The Vitamin K-dependent proteins may be in either an activated or a non-activated form, such as Factor II and Factor IIa, and Factor X and Factor Xa.

In one embodiment of the invention the Vitamin K-dependent protein of interest is a coagulation factor, such as e.g. FVII or FVIIa polypeptides. In one embodiment the Vitamin K-dependent protein of interest is wild type human FVIIa.

In one embodiment of the invention, the protein contaminants is a second different Vitamin K-dependent protein. Thus, the protein of interest and the protein contaminant may both be a Vitamin K-dependent protein.

In one embodiment of the invention the protein contaminants is Protein S. In one embodiment, the protein contaminants is hamster Protein S.

In one embodiment of the invention the host cell is selected from the group consisting of CHO cells, 293 (HEK293) cells, BKH cells, HKB11 cells, SP2/0 cells, and NS0 cells.

The present invention furthermore relates to a host cell expressing a Vitamin K-dependent protein of interest, which host cell comprises a siRNA construct targeting at least one protein contaminant expressed by the host cell.

The term "siRNA" as used herein refers to small interfering RNA, sometimes known as short interfering RNA or silencing RNA known in the art of molecular biology.

In one embodiment the host cell has been modified by transfection with at least one siRNA polynucleotide construct targeting a mRNA encoding a protein contaminant expressed endogenous by the host cell.

In one embodiment the host cell expressing a Vitamin K-dependent protein of interest comprises a siRNA construct targeting at least one protein contaminant expressed by the host cell, wherein the protein contaminant is a second vitamin K-dependent protein.

In one embodiment the host cell expressing a Vitamin K-dependent protein of interest comprises a siRNA construct targeting at least one protein contaminant expressed by the host cell, wherein the protein contaminant is Protein S.

The present invention also relates to a cell expressing a Vitamin K-dependent protein of interest comprising a disrupted gene for at least one protein contaminant expressed by the host cell.

In one embodiment the host cell has been modified by disruption by gene knock-out of at least one endogenous gene encoding a protein contaminant expressed endogenous by the host cell. In one embodiment the endogenous gene encoding Protein S has been disrupted by gene knock-out of exon 1.

In one embodiment the host cell expressing a Vitamin K-dependent protein of interest comprises a disrupted gene for at least one protein contaminant expressed by the host cell, wherein the protein contaminant is a second vitamin K-dependent protein.

In one embodiment the host cell expressing a Vitamin K-dependent protein of interest comprises a disrupted gene for at least one protein contaminant expressed by the host cell, wherein the protein contaminant is Protein S.

In one embodiment the host cell expressing a Vitamin K-dependent protein of interest comprises a disrupted gene for Protein S, wherein the Protein S gene is disrupted by omission of exon 1.

In one embodiment the host cell expressing a Vitamin K-dependent protein of interest has been modified by transfection with at least one transcription factor binding to a DNA element of the gene encoding the protein contaminant expressed endogenous by the host cell.

In one embodiment the host cell expressing a Vitamin K-dependent protein of interest has been modified by transfection with at least one nuclease fusion protein for site-specific cleavage of the DNA strands encoding the protein contaminant expressed endogenous by the host cell.

The present invention furthermore relates to a cell expressing a Vitamin K-dependent protein of interest comprising a transcription factor binding to at least one protein contaminant expressed by the host cell.

In one embodiment the host cell expressing a Vitamin K-dependent protein of interest comprising a transcription factor binding to the DNA sequence encoding at least one protein contaminant, the protein contaminant is a second vitamin K-dependent protein.

In one embodiment the host cell expressing a Vitamin K-dependent protein of interest comprises a transcription factor binding to the DNA sequence encoding at least one protein contaminant, the protein contaminant is Protein S.

In one embodiment of the invention the transcription factor is a Zinc finger protein. In one embodiment of the invention the Zinc finger protein binds a DNA element comprising the sequence of SEQ ID NO 35.

In one embodiment of the invention the Zinc finger protein binds the GGAGAGGAGGGGGGG DNA element.

In one embodiment the host cell expressing a Vitamin K-dependent protein of interest is modified by random mutagenesis for disruption of at least one endogenous gene encoding a protein contaminant expressed endogenous by the host cell.

The present invention also relates to a method for reducing the content of at least one protein contaminant in a composition comprising a Vitamin K-dependent protein of interest, wherein at least one protein contaminant expressed by the host cell is inhibited.

In one embodiment the method for reducing the content of at least one protein contaminant in a composition comprising a Vitamin K-dependent protein of interest, wherein at least one protein contaminant expressed by the host cell is inhibited is a method comprising the use of siRNA.

In one embodiment the method for reducing the content of at least one protein contaminant in a composition comprising a Vitamin K-dependent protein of interest, wherein at least one protein contaminant expressed by the host cell is inhibited is a method comprising the use of Random mutagenesis.

In one embodiment the method for reducing the content of at least one protein contaminant in a composition comprising a Vitamin K-dependent protein of interest, wherein at least one protein contaminant expressed by the host cell is inhibited is a method comprising the use of Targeted knock-out.

The present invention furthermore relates to a nucleic acid sequence comprising the CHO Protein S cDNA sequence having the sequence of SEQ ID NO 3 or any functional fragments thereof.

The present invention also relates to a nucleic acid sequence comprising the CHO Protein S coding sequence having the sequence of SEQ ID NO 4 or any functional fragments thereof.

The present invention relates to an amino acid sequence comprising CHO Protein S sequence having the sequence of SEQ ID NO 5 or any functional fragments thereof.

The methods and means described herein may in principle be applied for generating compositions comprising any Vitamin K-dependent protein of interest which is devoid or substantially devoid of protein contaminants.

"Polypeptides" means any protein comprising the amino acid sequence of the wild-type protein, as well as their respective "variants", "related polypeptides", "derivatives" and "conjugates" thereof.

In particular, as used herein, the terms "Factor VII polypeptide" or "FVII polypeptide" means any protein comprising the amino acid sequence 1-406 of wild-type human Factor VIIa (i.e., a polypeptide having the amino acid sequence disclosed in U.S. Pat. No. 4,784,950), variants thereof as well as Factor VII-related polypeptides, Factor VII derivatives and Factor VII conjugates. This includes FVII variants, Factor VII-related polypeptides, Factor VII derivatives and Factor VII conjugates exhibiting substantially the same or improved biological activity relative to wild-type human Factor VIIa.

The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

Variants of Factor VII may exhibit different properties relative to human Factor VII, including stability, phospholipid binding, altered specific activity, and the like.

"Factor VII" or "Factor VIIa" within the above definition also includes natural allelic variations that may exist and occur from one individual to another. Also, degree and location of glycosylation or other post-translation modifications may vary depending on the chosen host cells and the nature of the host cellular environment.

As used herein, "wild type human FVIIa" is a polypeptide having the amino acid sequence disclosed in U.S. Pat. No. 4,784,950.

The term "Factor VII derivative" as used herein, is intended to designate a FVII polypeptide exhibiting substantially the same or improved biological activity relative to wild-type Factor VII, in which one or more of the amino acids of the parent peptide have been genetically and/or chemically and/or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated FVII derivatives as disclosed in WO 03/31464 and U.S. patent applications U.S. 20040043446, U.S. 20040063911, U.S. 20040142856, U.S. 20040137557, and U.S. 20040132640 (Neose Technologies, Inc.); FVII conjugates as disclosed in WO 01/04287, U.S. patent application 20030165996, WO 01/58935, WO 03/93465 (Maxygen ApS) and WO 02/02764, U.S. patent application 20030211094 (University of Minnesota).

The term "improved biological activity" refers to FVII polypeptides with i) substantially the same or increased proteolytic activity compared to recombinant wild type human Factor VIIa or ii) to FVII polypeptides with substantially the same or increased TF binding activity compared to recombinant wild type human Factor VIIa or iii) to FVII polypeptides with substantially the same or increased half life in blood plasma compared to recombinant wild type human Factor VIIa. The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

Non-limiting examples of Factor VII variants having substantially the same or increased proteolytic activity compared to recombinant wild type human Factor VIIa include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189 (corresponding to WO 02/077218); and FVII variants exhibiting increased proteolytic stability as disclosed in WO 02/38162 (Scripps Research Institute); FVII variants having a modified Gla-domain and exhibiting an enhanced membrane binding as disclosed in WO 99/20767, U.S. Pat. No. 6,017,882 and U.S. Pat. No. 6,747,003, U.S. patent application 20030100506 (University of Minnesota) and WO 00/66753, U.S. patent applications U.S. 20010018414, U.S. 2004220106, and U.S. 200131005, U.S. Pat. No. 6,762,286 and U.S. Pat. No. 6,693,075 (University of Minnesota); and FVII variants as disclosed in WO 01/58935, U.S. Pat. No. 6,806,063, U.S. patent application 20030096338 (Maxygen ApS), WO 03/93465 (Maxygen ApS), WO 04/029,091 (Maxygen ApS), WO 04/083,361 (Maxygen ApS), and WO 04/111,242 (Maxygen ApS), as well as in WO 04/108,763 (Canadian Blood Services).

Non-limiting examples of FVII variants having increased biological activity compared to wild-type FVIIa include FVII variants as disclosed in WO 01/83725, WO 02/22776, WO 02/077218, WO 03/027147, WO 04/029090, WO 05/075635, and European patent application with application number 05108713.8 (Novo Nordisk A/S), WO 02/38162 (Scripps Research Institute); and FVIIa variants with enhanced activity as disclosed in JP 2001061479 (Chemo-Sero-Therapeutic Res Inst.).

Examples of variants of factor VII include, without limitation, P10Q-FVII, K32E-FVII, P10Q/K32E-FVII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/

K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158D/E296V/M298Q/K337A/S314E-FVII, F374Y/L305V/V158D/E296V/M298Q/S314E-FVII, F374Y/L305V/E296V/M298Q/V158T/S314E-FVII, F374Y/L305V/E296V/M298Q/K337A/V158T-FVII, F374Y/L305V/E296V/K337A/V158T/S314E-FVII, F374Y/L305V/M298Q/K337A/V158T/S314E-FVII, F374Y/L305V/V158D/E296V/M298Q/K337A-FVII, F374Y/L305V/V158D/E296V/K337A/S314E-FVII, F374Y/L305V/V158D/M298Q/K337A/S314E-FVII, F374Y/L305V/E296V/M298Q/K337A/V158T/S314E-FVII, F374Y/L305V/V158D/E296V/M298Q/K337A/S314E-FVII, S52A-Factor VII, S60A-Factor VII; R152E-Factor VII, S344A-Factor VII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn; FVII having substitutions, additions or deletions in the amino acid sequence from 304Arg to 329Cys; and FVII having substitutions, additions or deletions in the amino acid sequence from 153Ile to 223Arg.

Thus, substitution variants in a factor VII polypeptide include, without limitation substitutions in positions P10, K32, L305, M306, D309, L305, L305, F374, V158, M298, V158, E296, K337, M298, M298, S336, S314, K316, K316, F374, S52, S60, R152, S344, T106, K143, N145, V253, R290, A292, G291, R315, V317, and substitutions, additions or deletions in the amino acid sequence from T233 to N240 or from R304 to C329; or from I153 to R223, or combinations thereof, in particular variants such as P10Q, K32E, L305V, M306D, D309S, L305I, L305T, F374P, V158T, M298Q, V158D, E296V, K337A, M298Q, M298K, S336G, S314E, K316H, K316Q, F374Y, S52A, S60A, R152E, S344A, T106N, K143N, N145T, V253N, R290N, A292T, G291N, R315N, V317T, and substitutions, additions or deletions in the amino acid sequence from T233 to N240, or from R304 to C329, or from I153 to R223, or combinations thereof.

"A Vitamin K-dependent protein of interest" as used herein refers to the single Vitamin K-dependent protein product produced by the host cells, which is relevant to obtain in the most pure form. In one embodiment vitamin K-dependent protein of interest is the protein product produced in the highest amount by the host cell. In one embodiment, the Vitamin K-dependent protein of interest in transfected into the host cell.

"Composition" as used herein, means any composition, such as a liquid composition, such as an aqueous liquid composition.

The Vitamin K-dependent protein of interest is most typically one produced under cell culture conditions, i.e. the Vitamin K-dependent protein of interest is either obtained directly as a constituent of a cell culture supernatant, or obtained from a cell culture supernatant after one or more subsequent purification process steps.

Typically, the total content of protein contaminants in the non-purified composition is at least 200 ppm, such as at least 300 ppm, e.g. at least 400 ppm, or at least 500 ppm. Also typically, the total content of Protein S contaminants in the non-purified composition is at least 200 ppm, such as at least 300 ppm, e.g. at least 400 ppm, or at least 500 ppm.

"Protein contaminant" and "protein contaminants" as used herein, means protein or polypeptide constituents produced endogenously by the host cell and constituting an impurity in relation to the Vitamin K-dependent protein of interest. Thus, the Vitamin K-dependent protein of interest is obviously not be counted as a protein contaminant.

"Devoid or substantially devoid" as used herein, refers to a composition wherein the total content of a protein contaminant in the composition is at the most 500 ppm, such as at the most 100 ppm, such as at the most 10 ppm, e.g. at the most 1 ppm, or at the most 0.1 ppm. Also typically, the total content of Protein S contaminants in the composition is at the most 500 ppm, such as at the most 100 ppm, such as at the most 10 ppm, e.g. at the most 1 ppm, or at the most 0.1 ppm.

The phrase "express a substantially lower amount of at least one protein contaminant" as used herein, refers to the expression level of an endogenous protein contaminant, which is reduced by at least 30%, such as by at least 40%, such as by at least 50%, such as by at least 60%, such as by at least 80%, such as by at least 90%, such as by at least 95%, such as by at least 99%.

A particularly relevant class of protein contaminant are proteins very similar to the Vitamin K-dependent protein of interest, such as any other protein containing a Gla-domain including the proteins: GAS-6, Protein S, Factor II (Prothrombin), Factor Xa, Factor IXa, Protein C, Factor VIIa, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Matrix Gla protein, and Osteocalcin.

As a non-limiting example, Protein S is sometimes seen as an impurity in the production of recombinant FVIIa in mammalian cells. Protein S is like FVII a Vitamin K-dependent plasma glycoprotein containing an EGF-like domain and a gamma-carboxy-glutamate (Gla) domain. Due to the structural similarity between FVII(a) and Protein S, it is difficult to recover FVII by means of chromatographic methods supra without contamination with Protein S. It would therefore be desirable to prevent the expression of Protein S by the host cell. This may be obtained by targeting the mRNA or the genome.

Stable expression of small interfering RNA, siRNA, is a new technology that enables reduction of targeted mRNA and thus suppression of targeted gene expression in mammalian cells (T. R. Brummelkamp, R. Bernards, and R. Agami. Science 296(5567): 550-553, 2002 & M. Mivaaishi and K Taira. Nat. Biotechnol 20(5):497-200, 2002.) A number of individual siRNA have been generated in a strategy similar to the ones described in the references. Some of these siRNAs have proven useful (Example 2).

The use of random mutagenesis to introduce genomic changes in the host cells, some of which may prevent the generation of mRNA in the host cell may also be exploited. This may be achieved by treating a population of CHO cells with a mutagen such as e.g. Ethyl Methane Sulfonate, EMS, which induces point mutations in the cells. The surviving cells may exhibit altered phenotypes, because of these mutations. The cells may be seeded in a screening format (e.g. 96-well plates) to allow isolation of clonal cell populations. Following a growth period, medium may be harvested from the wells and assayed for Protein S content. Clones without Protein S expression may be isolated and used for production of Protein S-free Factor VII.

Disruption of the genome may be obtained by gene targeting or the knock-out technique (Example 3). The generation of knock-out cells is a well-described technique for eradicating expression of endogenous proteins, and a CHO knock-out cell was recently described in Yamane-Ohnuki et al. Biotechnol. Bioeng. 87 (5):614-622, 2004.

Genomic Protein S knockout plasmid was generated and transfected into CHO cells. By homologous recombination the Protein S gene in the CHO cells was disrupted. This procedure was repeated until all alleles of the Protein S gene was stably removed (Example 3).

Transcription factor engineering for transcriptional down regulation is an alternative way of modifying the gene expression (Example 4).

These methods may in theory be suitable for removing any unwanted host cell protein contaminants. For all of these methods to be applied it requires the knowledge of the gene sequence of the contaminating protein. The sequence of Protein S for Chinese Ovary Hamster, CHO, is not public available and a cloning of CHO Protein S cDNA was performed as described in Example 1 and disclosed as SEQ ID NO 1. The CHO Protein S coding sequence and the CHO Protein S amino acid sequence are disclosed as SEQ ID NO 2 and 3 respectively.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

Embodiments of the Invention

1. A composition comprising a Vitamin K-dependent protein of interest devoid or substantially devoid of at least one protein contaminant expressed by a host cell.
2. The composition according to embodiment 1, wherein the Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.
3. The composition according to embodiment 1, wherein at least one of said protein contaminants is a vitamin K-dependent protein.
4. The composition according to embodiment 1, wherein at least one of said protein contaminants is Protein S.
5. The composition according to embodiment 1, wherein the host cell is selected from the group consisting of CHO cells, 293 (HEK293) cells, BKH cells, HKB11 cells, SP2/0 cells, and NS0 cells.
6. A cell expressing a Vitamin K-dependent protein of interest according to any of embodiments 1-5 further comprising a siRNA construct targeting at least one protein contaminant expressed by the host cell.
7. The cell according to embodiment 6, wherein said at least one protein contaminant is a vitamin K-dependent protein.
8. The cell according to any of embodiments 6-7, wherein said at least one protein contaminant is Protein S.
9. A cell expressing a Vitamin K-dependent protein of interest according to any of embodiments 1-5 further comprising a disrupted gene for at least one protein contaminant expressed by the host cell.
10. The cell according to embodiment 9, wherein said at least one protein contaminant is a vitamin K-dependent protein
11. The cell according to any of embodiments 9-10, wherein said at least one protein contaminant is Protein S.
12. The cell according to any of embodiments 9-11, wherein the Protein S gene is disrupted by omission of exon 1
13. A cell expressing a Vitamin K-dependent protein of interest according to any of embodiments 1-5 further comprising a transcription factor binding to at least one protein contaminant expressed by the host cell.
14. The cell according to embodiment 13, wherein said at least one protein contaminant is a vitamin K-dependent protein
15. The cell according to any of embodiments 13-14, wherein said at least one protein contaminant is Protein S.
16. The cell according to any of embodiments 13-15, wherein the transcription factor is a Zinc finger protein.
17. The cell according to any of embodiments 15-16, wherein the Zinc finger protein binds the GGAGAG-GAGGGGGGG DNA element.
18. A method for reducing the content of at least one protein contaminant in a composition comprising a Vitamin K-dependent protein of interest wherein at least one protein contaminant expressed by the host cell is inhibited
19. The method according to embodiment 18, wherein the method comprises the use of siRNA.
20. The method according to embodiment 18, wherein the method comprises the use of Random mutagenesis.
21. The method according to embodiment 18, wherein the method comprises the use of Targeted knock-out.
22. A nucleic acid sequence comprising the CHO Protein S cDNA sequence having the sequence of SEQ ID NO 1.
23. A nucleic acid sequence comprising the CHO Protein S coding sequence having the sequence of SEQ ID NO 2.
24. An amino acid sequence comprising CHO Protein S sequence having the sequence of SEQ ID NO 3.

Further Embodiments of the Invention:

1a. A host cell expressing a Vitamin K-dependent protein of interest, said host cell being modified to express a substantially lower amount of at least one protein contaminant expressed endogenous by said host cell in the absence of said modification.
2a. The host cell according to embodiment 1a, wherein said Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.
3a. The host cell according to any one of embodiments 1a-2a, wherein said protein contaminants is a second vitamin K-dependent protein.
4a. The host cell according to any one of embodiments 1a-3a, wherein said protein contaminant is Protein S.
5a. The host cell according to any one of embodiments 1a-4-a, wherein the host cell is selected from the group consisting of CHO cells, 293 (HEK293) cells, BKH cells, HKB11 cells, SP2/0 cells, and NS0 cells.
6a. The host cell according to any one of embodiments 1a-5a, wherein said cell has been modified by transfection with at least one siRNA polynucleotide construct targeting a mRNA encoding a protein contaminant expressed endogenous by said host cell.

7a. The host cell according to any one of embodiments 1a-6a, wherein said cell has been modified by disruption by gene knock-out of at least one endogenous gene encoding a protein contaminant expressed endogenous by said host cell.

8a. The host cell according to embodiment 7a, wherein the endogenous gene encoding Protein S has been disrupted by gene knock-out of exon 1.

9a. The host cell according to any one of embodiments 1a-8a, wherein said cell has been modified by transfection with at least one transcription factor binding to a DNA element of the gene encoding said protein contaminant expressed endogenous by said host cell. 10a. The host cell according to embodiment 9a, wherein said transcription factor is a Zinc finger protein.

11a. The host cell according to embodiment 10a, wherein said Zinc finger protein binds a DNA element comprising the sequence of SEQ ID NO 35.

12a. The host cell according to any one of embodiments 1a-11a, wherein said cell has been modified by random mutagenesis for disruption of at least one endogenous gene encoding a protein contaminant expressed endogenous by said host cell.

13a. A method for producing a host cell according to any one of embodiments 1a-12a, said method comprising the following steps in any order:

a) optionally transfecting said cell with a polynucleotide construct encoding a Vitamin K-dependent protein of interest; and b) modifying said cell to express a substantially lower amount of at least one protein contaminant expressed endogenous by said host cell in the absence of said modification.

14a. The method according to embodiment 13a, wherein said Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.

15a. The method according to any one of embodiments 13a-14a, wherein said protein contaminants is a second vitamin K-dependent protein.

16a. The method according to any one of embodiments 13a-15a, wherein said protein contaminant is Protein S.

17a. The method according to any one of embodiments 13a-16a, wherein the host cell is selected from the group consisting of CHO cells, 293 (HEK293) cells, BKH cells, HKB11 cells, SP2/0 cells, and NS0 cells.

18a. The method according to any one of embodiments 13a-17a, wherein said cell has been modified by transfection with at least one siRNA polynucleotide construct targeting a mRNA encoding a protein contaminant expressed endogenous by said host cell.

19a. The method according to any one of embodiments 13a-18a, wherein said cell has been modified by disruption by gene knock-out of at least one endogenous gene encoding a protein contaminant expressed endogenous by said host cell.

20a. The method according to embodiment 19a, wherein the endogenous gene encoding Protein S has been disrupted by gene knock-out of exon 1.

21a. The method according to any one of embodiments 13a-20a, wherein said cell has been modified by transfection with at least one transcription factor binding to a DNA element of the gene encoding said protein contaminant expressed endogenous by said host cell.

22a. The method according to embodiment 21a, wherein said transcription factor is a Zinc finger protein.

23a. The method according to embodiment 22a, wherein said Zinc finger protein binds a DNA element comprising the sequence of SEQ ID NO 35.

24a. The method according to any one of embodiments 13a-23a, wherein said cell has been modified by random mutagenesis for disruption of at least one endogenous gene encoding a protein contaminant expressed endogenous by said host cell.

25a. A method for producing a composition comprising a Vitamin K-dependent protein of interest with a substantially lower amount of at least one protein contaminant expressed endogenous by said host cell in the absence of modification, said method comprising the steps of:

a) producing a host cell according to any one methods of embodiments 13a-24a; and b) growing said host cell in a growth medium and harvesting said growth medium comprising said Vitamin K-dependent protein of interest.

26a. A composition produced by the method according to embodiment 25a.

27a. A nucleic acid sequence comprising the sequence of SEQ ID NO 1.

28a. A nucleic acid sequence comprising the sequence of SEQ ID NO 2.

29a. An amino acid sequence comprising the sequence of SEQ ID NO 3.

EXAMPLES

Example 1

Cloning of CHO Protein S cDNA

The Chinese Hamster Ovary, CHO, Protein S cDNA sequence was not known from any nucleotide or protein database but was expected to have high identity to the nucleotide sequence of Protein S from other rodents.

CHO Protein S PCR fragments were generated from CHO cDNA using primers designed from alignment between mouse and rat Protein S cDNA sequences or genomic sequences. The cDNA fragments were sequenced and assembled to form a full-length coding sequence for the CHO Protein S gene. The full-length CHO Protein S cDNA was cloned by PCR using the primers "CHO ProtS forward" and "CHO ProtS reverse" and CHO-K1 derived cDNA as template.

The predicted CHO Protein S amino acid sequence has 90.5% identity to mouse Protein S and 90.7% identity to rat Protein S.

CHO ProtS forward (SEQ ID NO 1):
5'-GCCCAGGCTCGCAGCTCCTCTGG-3'

CHO ProtS reverse (SEQ ID NO 2):
5'-CAGGTGACACCTGCCAGCTGGTG-3'

CHO Protein S cDNA sequence (SEQ ID NO 3):
gcccaggctcgcagctcctctgggcggagcgccggctcggtccccgctgcgccagccgtgatccccggcagcctgctcagcaa tgagggtcctgagcgcgcgctgtcggctactgctggtatgcctagccctggtgctgccagcctcggagacaaacttttttgtcaa aagaacatgcctcgcaagtcctggtgaggaagcgccgcgcaaataccttgcttgaagaaactaaaaagggcaatcttgaaa gagaatgcatcgaagagctctgcaataaagaggaagccagggaggtctttgaaaacaatcccgaaacggattattttttatcc aaaatatttggttgtctgggcatgttccgtgctggcctgttcagtgctgcgcggcagtctgttaatgcttaccccgacctcagga gctgtgtcaatgccatcccagaccaatgtgatcctatgccatgcaatgaagatgggtatctgagctgcaaagatggccaagct gctttcacatgcatctgcaaaccaggatggcaaggggacaaatgccagtttgatgtaaatgaatgtaaagatcccttaaatgta aatgggggctgcagccagatttgtgacaacactcctggaagttaccactgctcctgcagaagtggctttgctatgctttcaaaca aaaaagactgcaaagatgtggatgaatgctctatgaagcccagtgtttgtggctcagctgtgtgcaagaacactccaggaga ctatgagtgtgaatgtcctgacggctacagatatgatccctcatcgaagtcttgcaaagatgtggacgaatgctctgagaacat gtgtgctcaattgtgtgtcaattaccctggaggctactcttgttactgtgatggaaagaaaggattcaagcttgcccaagatcag aagagttgtgagggtattccagtgtgccttcccttgaaccttgacaaaaattatgaattattgtacttggctgagcagtttgtagg agttgtcttatatctgaaatttcgtttgccagaaattaccagattttcagctgaatttgattttcggacatatgattcagagggcatc atcctgtatgcagaatctcttgatcactcaaattggctcctgattgcacttcgtgatggaaaaattgaagttcagtttaagaatga gttttcaacccaaatcacaaccggaggcaatgttattaacaatggtaaatggaacatggtatccgtggaagaattagacgaca gtgttagcattaaaatagctaaagaagctgtgatgaatataaataaatttgggagcctcttaaacctacagatggatttctgga caccaaaatatactttgcaggattacctcgggtagtggaaagtgcactcattaaaccgattaaccctcgtctggatggatgtata cgaggctggaacttgatgaaacaaggagctttaggtgcaaaggaaattattcaaggaaaacaaaataagcattgcttcctcat ggtggagaagggctcctactaccctggttctggaattgctcggttcagcatagattacaataatgtaaccaatgcagagggctg gcaaataaatgtgaccttgaatattcgtccatccactggcactggaattatgcttgccttggtttctggagacaaagtgcccttg ccttgtccttggtgggctccagctctgaaaattctcaggatattgtggtatttgttgaaaattcagtggtggctcgaatggaggcc ataactctgtgttctgaccagcaatcccaactgaaatgtaatgttaacagacatggcctagagctatggagcccactgaagaa agatgtcatctactctaaagatatttcaaggacaactagcagtcttggacaaagcaatgaaaggaaacgtggccacttatctgg gtggcattccagatctttccttcagtgccacgccagtgaatgccttctacagtggctgcatggaagtgaacatcaacgggtgc agttggatctggatgaagccatttctaaacataatgacatcagagctcactcatgtccttcagttaagaaaatccagaagaacg tctaatgtctgttttctgtgcttataatgccccttccttgtaattatgctcacgcccctatcaccagctggcaggtgtcacctgtgaa gtgcaatgtttgaaatgatgtggactttgtccttcagattttgttatataaaccacgttttttttttttttttaaagtctttcttctattg ctgtctagaaattaaataa CHO Protein S coding sequence (SEQ ID NO 4):
atgagggtcctgagcgcgcgctgtcggctactgctggtatgcctagccctggtgctgccagcctcggagacaaacttttttgtca aaagaacatgcctcgcaagtcctggtgaggaagcgccgcgcaaataccttgcttgaagaaactaaaaagggcaatcttgaa agagaatgcatcgaagagctctgcaataaagaggaagccagggaggtctttgaaaacaatcccgaaacggattattttttatc caaaatatttggttgtctgggcatgttccgtgctggcctgttcagtgctgcgcggcagtctgttaatgcttaccccgacctcagg agctgtgtcaatgccatcccagaccaatgtgatcctatgccatgcaatgaagatgggtatctgagctgcaaagatggccaagc tgctttcacatgcatctgcaaaccaggatggcaaggggacaaatgccagtttgatgtaaatgaatgtaaagatcccttaaatgt aaatgggggctgcagccagatttgtgacaacactcctggaagttaccactgctcctgcagaagtggctttgctatgctttcaaac aaaaaagactgcaaagatgtggatgaatgctctatgaagcccagtgtttgtggctcagctgtgtgcaagaacactccaggag -continued

```
actatgagtgtgaatgtcctgacggctacagatatgatccctcatcgaagtcttgcaaagatgtggacgaatgctctgagaaca tgtgtgctcaattgtgtgtcaattaccctggaggctactcttgttactgtgatggaaagaaaggattcaagcttgcccaagatca gaagagttgtgagggtattccagtgtgccttcccttgaaccttgacaaaaattatgaattattgtacttggctgagcagtttgtag gagttgtcttatatctgaaatttcgtttgccagaaattaccagattttcagctgaatttgattttcggacatatgattcagagggca tcatcctgtatgcagaatctcttgatcactcaaattggctcctgattgcacttcgtgatggaaaaattgaagttcagtttaagaat gagttttcaacccaaatcacaaccggaggcaatgttattaacaatggtaaatggaacatggtatccgtggaagaattagacga cagtgttagcattaaaatagctaaagaagctgtgatgaatataaataaatttgggagcctctttaaacctacagatggatttctg gacaccaaaatatactttgcaggattacctcgggtagtggaaagtgcactcattaaaccgattaaccctcgtctggatggatgt atacgaggctggaacttgatgaaacaaggagctttaggtgcaaaggaaattattcaaggaaaacaaaataagcattgcttcc tcatggtggagaagggctcctactaccctggttctggaattgctcggttcagcatagattacaataatgtaaccaatgcagagg gctggcaaataaatgtgaccttgaatattcgtccatccactggcactggaattatgcttgccttggtttctggagacaaagtgccc tttgccttgtccttggtgggctccagctctgaaaattctcaggatattgtggtatttgttgaaaattcagtggtggctcgaatggag gccataactctgtgttctgaccagcaatcccaactgaaatgtaatgttaacagacatggcctagagctatggagcccactgaag aaagatgtcatctactctaaagatattcaaggacaactagcagtcttggacaaagcaatgaaaggaaacgtggccacttatct gggtggcattccagatctttccttcagtgccacgccagtgaatgccttctacagtggctgcatggaagtgaacatcaacggggt gcagttggatctggatgaagccatttctaaacataatgacatcagagctcactcatgtccttcagttaagaaaatccagaagaa cgtctaa CHO Protein S amino acid sequence (SEQ ID NO 5):
mrvlsarcrlllvclalvlpasetnflskehasqvlvrkrrantlleetkkgnlerecieelcnkeearevfennpetdyfypkylgcl gmfraglfsaarqsvnaypdlrscvnaipdqcdpmpcnedgylsckdgqaaftcickpgwqgdkcqfdvneckdplnvng gcsqicdntpgsyhcscrsgfamlsnkkdckdvdecsmkpsvcgsavckntpgdyececpdgyrydpssksckdvdecs enmcaqlcvnypggyscycdgkkgfklaqdqksceginpvclplnldknyellylaeqfvgvvlylkfrlpeitrfsaefdfrtyds egiilyaesldhsnwllialrdgkievqfknefstqittggnvinngkwnmvsveelddsvsikiakeavmninkfgslfkptdgf ldtkiyfaglprvvesalikpinprldgcirgwnlmkqgalgakeiiqgkqnkhcflmvekgsyypgsgiarfsidynnvtnaeg wqinvtlnirpstgtgimlalvsgdkvpfalslvgsssensqdivvfvensvvarmeaitlcsdqqsqlkcnvnrhglelwsplk kdviyskdiqgqlavldkamkgnvatylggipdlsfsatpvnafysgcmevningvqldldeaiskhndirahscpsvkkiqk nv
```

Example 2

CHO Protein S mRNA Degradation by Use of Small Interfering RNA

The mRNA of Protein S in Chinese Hamster Ovary (CHO) cells can be degraded by the introduction of small interfering RNA, siRNA, into the cells. siRNA is a short double-stranded RNA molecule that may separate inside the cell and the antisense part of the molecule may hybridize to a complementary mRNA and induce cleavage of this mRNA by a process in which the Dicer nuclease plays a key role. The effect of siRNA is described in Elbashir-S M et al., Nature 411 (2001) 494-498. siRNA may be synthesized as single-stranded RNA and subsequently annealed to form the double-stranded siRNA molecule. The siRNA molecule may subsequently be transiently transfected into cells and exert its function. Alternatively, siRNA may be expressed as a hairpin molecule under regulation of a Polymerase III promoter as described in Brummelkamp T R; Bernards R; Agami R, Science 296 (2002) 550-553.

A vector that permits the transcription of each of two complementary strands by individual promoters was developed in our laboratory. The vector is called RansiRNA because random DNA can be inserted into it and both strands of the insert can be transcribed. The RansiRNA vector contains the human H1 polymerase III promoter and the mouse U6 polymerase III promoter. The two promoters are pointed towards the siRNA template from each direction, transcribing the sense and antisense strand of the siRNA molecule, respectively. The vector also harbors the hygromycin drug resistance gene. The RansiRNA vector is similar, but not identical, to the pHippy vector described by Kaykas & Moon (Kaykas-A & Moon-R T, BMC Cell Biology Vol. 5 (1) pp. 16 (2004).

Several target siRNA sequences were selected from the CHO Protein S coding sequence, only targets containing the sequence AGN$_{17}$CT (SEQ ID NO 6) were chosen. Each target sequence were purchased as two complementary DNA oligonucleotides extended with A's 5' to the target and T's 3' the target which serve as termination signal when transcribed in reverse and forward direction. The oligonucleotides also harbor a four base-pair 5'-overhang which is compatible with the Bgl II restriction site (GATC). The annealed oligonucleotides are cloned into the BglII-site of the RansiRNA-hygro vector.

The specified siRNA constructs were stably transfected into a CHO K1 cell line expressing a human FVII analogue. Cells were plated in 6-well plates at density of $2 \times 10^5$ c/well in complete medium (DMEM medium containing 10% FBS, non-essential amino acids and vitamin K). After two days the cells were transfected at 90% confluency. Transfection using Lipofectamine-2000 (Invitrogen) was performed according to recommendations from the manufacturer. After 48 hours the cells were transferred to selection medium, which was composed of complete medium additionally supplemented with 300 ug/ml hygromycin. After selection for 14 days, cells were cloned by limiting dilution. After clones had grown up the FBS containing complete medium was changed to serum free medium (PF CHO supplemented with vitamin K, Hyclone) in order to avoid detection of bovine protein S in the following ELISA. The supernatant from approximately 100 clones for each siRNA construct were screened by protein S ELISA using human protein S as standard. The same supernatant was also screened by a human FVII ELISA. The clones that had the lowest expression of protein S and that had not lost the expression of FVII were further characterized. Clones that had down regulated the expression of protein S to the level of only 10% of the expression level exhibited by the parental CHO K1 FVII expressing cell line were isolated.

siRNA Target Sequences

```
#821 siRNA1 target (SEQ ID NO 7):
5'-agtgtgaatgtcctgacggct-3'

#821 siRNA1 upper oligo (SEQ ID NO 8):
5'-gatctaaaaaagtgtgaatgtcctgacggcttttta-3'

#821 siRNA1 lower oligo (SEQ ID NO 9):
5'-gatctaaaaaagccgtcaggacattcacactttttta-3'

#822 siRNA2 target (SEQ ID NO 10):
5'-agctgcaaagatggccaagct-3'

#822 siRNA2 upper oligo (SEQ ID NO 11):
5'-gatctaaaaaagctgcaaagatggccaagcttttta-3'

#822 siRNA2 lower oligo (SEQ ID NO 12):
5'-gatctaaaaaagcttggccatctttgcagcttttta-3'

#835 siRNA4 target (SEQ ID NO 13):
5'-agaacatgcctcgcaagtcct-3'

#835 siRNA4 upper oligo (SEQ ID NO 14):
5'-gatctaaaaaagaacatgcctcgcaagtcctttttta-3'

#835 siRNA4 lower oligo (SEQ ID NO 15):
5'-gatctaaaaaaggacttgcgaggcatgttctttttta-3'

#836 siRNA5 target (SEQ ID NO 16):
5'-agaaactaaaaagggcaatct-3'

#836 siRNA5 upper oligo (SEQ ID NO 17):
5'-gatctaaaaaagaaactaaaaagggcaatctttttta-3'

#836 siRNA5 lower oligo (SEQ ID NO 18):
5'-gatctaaaaaagattgcccttttagtttctttttta-3'

#837 siRNA6 target (SEQ ID NO 19):
5'-agccagatttgtgacaacact-3'
```

```
-continued
#837 siRNA6 upper oligo (SEQ ID NO 20):
5'-gatctaaaaaagccagatttgtgacaacactttttta-3'

#837 siRNA6 lower oligo (SEQ ID NO 21):
5'-gatctaaaaaagtgttgtcacaaatctggcttttta-3'
```

Example 3

Gene Targeting of CHO Protein S

A definitive way of abolishing protein expression of Protein S is to disrupt the gene. The technique of "gene targeting" or "gene knock-out" in mice has been known for many years. Gene targeting in cultured cells is also well established, and an example of a CHO knock-out cell was recently described in Yamane-Ohnukiet et al. Biotechnology and Bioengineering, 87(5): 614-622, 2004.

We predicted the exon structure of the CHO Protein S gene by an alignment of the CHO Protein S cDNA to the human gene. Primers designed to bind in exon 1 and exon 2 of CHO Protein S was used in a Polymerase Chain Reaction, PCR, the template was CHO genomic DNA. The amplified 4.4 kb product was sequenced. Primers binding exon 2 and exon 3 was used to PCR amplify intron 2. An amplified fragment of 3.5 kb harboring intron 2 was cloned and sequenced.

The regions upstream of exon 1 from mouse and rat Protein S were aligned and sequence stretches with high identity were used to design oligonucleotide primers for use in PCR. A 1650 bp 5'UT/promoter band was cloned and sequenced. The gene targeting construct will combine the "1.6 kb 5' UT/promoter fragment", "Plox-PGK-hygromycin resistance gene-Plox", "intron 1", "exon 2" and "PGK-TK". This construct is omitting the coding sequence from exon 1 in CHO Protein S, encoding the amino acids MRVLSVRCRLLLVCLALVL-PASETN (SEQ ID NO 22). A second construct containing the blasticidin drug resistance gene can be made in a similar way.

The "hygromycin"-gene targeting construct can electroporated into CHO cells and cells plated in dishes. The next days the cells are exposed to 600 microg/ml hygromycin and 1 micromolar ganciclovir. The clones are now selected for hygromycin resistance gene and against herpes simplex thymidine kinase gene. After colonies appeared they will be transferred to 96 wells plates. The cells grow to confluence and duplicates of the plates will be made. Genomic DNA is harvested from the cell clones and PCR-reactions using a hygromycin resistance gene specific primer and a primer 3' the promoter present in the construct are performed. Clones with a positive PCR-band are grown in flasks and a Southern blot will be made to verify the PCR result. Second, the targeting construct harboring the blasticidin resistance gene are electroporated into the hemizygous CHO cells whereafter the cells are selected for the blasticidin resistance gene and against thymidine kinase gene using 10 microg/ml blasticidin and 1 micro-molar ganciclovir. Again, cell clones are PCR verified using a blasticidin resistance gene specific primer and a primer 3' to the promoter present in the construct. Positive clones are again tested by Southern blots. Homozygous disruptants are transfected with a Cre recombinase expressing plasmid. Cre recombinase will recombine the lox sites and remove the drug-resistance genes.

Intron 1 primers:
CHO-protein-S-exon1-forw2 (SEQ ID NO 23):
5'-CTGCTGGTATGCCTAGCCCTGGTG-3'

CHO-protein-S-exon2-rev2 (SEQ ID NO 24):
5'-TGCAGAGCTCTTCGATGCATTCTC-3'

Intron 2 primers:
CHO-protein-S-exon2-forw2 (SEQ ID NO 25):
5'-AAGGGCAATCTTGAAAGAGAATGC-3'

CHO-protein-S-exon3rev (SEQ ID NO 26):
5'-CCAAATATTTTGGATAAAAATAATC-3'

5'UT/promoter primers:
PS-CHO promoter f2 (SEQ ID NO 27):
5'-AARCAACCCCTTTTGACCAT-3'

CHO-protein-S.promoterRev1 (SEQ ID NO 28):
5'-CCCAGAGGAGCTGCGAGCCTG-3'

5'UT/promoter (immediately 5' to coding sequence) (SEQ ID NO 29):
aarcaaccccttttgaccatacacatttctactctttgtgtttgctggagctgttttctccccacactcaaccccctttgctgaagcct ggaacttgctttccacagcttaagttgttataggtttcaatcatctgtccacctccctgactttcataattttgtgaaatacccttgca tatatatgggactaaatattattttctcctggttgtccataatagattaatttaattcctaaacaaagaacagaacatagattgg tatagtagaagagtttcccttctccctactgcatgaatggaaattccccaaaccatccttatcagagaaattaactcacatactag tcacctttcattcagctggatgacaaaatcattttaaaaaaagagaataaagaaaacagataagaacaactagatctaggaat aatacttaaaatatgattctgcttagtaggtttcattcacacacctagaaaaaaaaatcagtcaatgtttcctttgggcagaaaat gagcaataatgggtatgcattgaccactactgttggacatagccttattgcttcatatagcatctattcaaagtctcagatcaaca ctatgaaaacctgtcatctctgtattagatgatgtgactggggctgtaaagggtaagctcttttcttacagctatacaacaacgct aagaccaagttctgtgctttgagcccaggcagtttagtttcccaggagcaacctaaagcctgattcacaggcatatgtatgatcc aaactgaatggtagtacatcaataccaaaacaatctattggtggaaacacaccataggtgatcgaaatactccattttcttttcct ctcatgacttctgttctgagcagtcctcttcctaaagtctacattgtcttctgagttcaggctgacatcttgacatcctcctggctgg cacagtctctggacaaggagggaagaaggagagaaggggaaagggagaggaggggggagggagagaaagaatggg aagaggaaggatatgaaagagagaagagaggagggaaggcgggaggaagggagggagggagggagggagagagg gagagagaggagagagagagagagagagagagagagagagagagagagagagagagagagagagagagagggagaggg agagagagacagagagagagagagggagagggagagagagagagagagagagagagagagagagagagagagagag agtgaggagagagagagagtttctcttcaccattggacattcctaaagaaaagaagtaaatgcaggattggggacagtga cagaggacctctgataaactttctgaggcctctgacctcactctctcggagccctcctccaccaccaccccccccctccctagct gagaaaagcttccaggaaatgtcccagtcatcgcttcccctcccgggctgggggctgggagcgggcggtcccctcaggccag ggctgctccggccgcgctcgggcagggccacaacagagctgggaaagctgagcccaggctcgcagctcctctgggcggagc gccggctcggtccccgctgcgccagccgtgatccccggcagcctgctcagca exon1 (SEQ ID NO 30):
atgagggtcctgagcgtacgctgtcggctactgctggtatgcctagccctggtgctgccagcctcggagacaaac intron1 (SEQ ID NO 31):
tgtaagtaatccatacctcctggcttctccattccctatgtgccccggcttgaagattttccactaggctgtttgctgcctcctaagtt tccagtaagtccgccaccattcagagagtcgcggcagcctgggtctggtgggcagtgtaaaggtgggacaggatcaaagctt gccttgctttgagaaccattgtccacaggacttgattccagaacccgggtgacactaagtgtcaaaggaattgcttgaacatag tcctaaatattgctaggaaagctaagtcaagcctgttgccctcctcccgtttacaagagtgccccagcccgcaccctctcctgcg gctaaccttccttttgcaatttctggactttgaacttgattgactggtctcacattgacaaactgtttggggactgctggggtgttac atatgattctctaaccttgatataagaaatagctgttggatgttaccttgtaccgaggatcattttctgagggttttgactgttgcc gctttgagatggcagcaagaattctgtacaacacacacattttgtgtttcttggtcttttcctcttcccattctcagattccgggcag -continued

```
tatatcgagttttctcttagaaatataaaacgaaccacaaggttttagtacattttaatggtcaattaaattgttttagaagcttaa
atatgttcataattaacactgcttctttgtctctttgtagtcccagtcactggcatgggagcaataactgtataacaaataccact
taggtcactgcgagcaccaaagaaacttttcaaagatggtaattaagtaggagtttgctggaattgcaagttttattaattagt
aaggaatctagcctgatattttaaatgtctaactaagttaaagaccagaatgaaactggttcattttattgaggataaacaa
gttacagttataaagcctcaacaatcaaagccctacgatgaagcagcgtgtgactgtatgcacatgatctatcttgttcagagg
aacaatcaaacattttcagatagcatcagggcggtggtactcgcctataatcctagcaaagtcagaggcaagcagatctc
tgtgttcaaggccagcctagtctacagagtgagttccaggacaactgggctacacagagaaacctgtctcagagaaaaca
aaataaaaccaaattcagatagctggtgtttgggaaaagagcaaaagacagcagtgctggccacacagagagtagacaag
ttcattctacaaggacatcacagaaagaatatgtgacccaatgacgaccataaactttcttgttcctgtgtcaaattatctccggt
ttattgatgaagaaccagacactatgagctgcgtctcctccttaagattttgttttggtgtcttgttttgtcaaggggtttcattgtg
gccctgagcattagatccagggctttgtgcatgctaggccagggagctatattcccgaactccagaagactaggaatttgagat
ataaatagaatttgaattaccttctgtacaattgattgtatggttctagaaatattgctatattaagggaagcctttgcagaagac
agttattttgagatggtgcataacacaaaagaaatgaactaaagcctgaggcctgctctgtagctctgccttgcccttagcctac
aataactttctttacctttcaagcatgtgccaccacgcctgactttcaggcccttcattttaacaagaaagcaagtattcagttatc
aactgactttccaaatgcatttgtatgaataaaaactacaaaaatataaaataagaactatacacacaaaagccttgtattta
aaatttacgctgtggacatattttgctcatcattcgtgagagcttgcggtaaaaaggcaaaggggaagaggaggatatctatt
tgggtaggctaatttggccttatccagacttccctttgggtggatgcagtctgcccagcacactattggcccatttcttctacatg
gctttgtgctctgctctgcccttagctaattgtcccctttgacatgcttttgtctttccttaaagtttctatacttcaaaaaccatcccgc
tacactaatggagtgattttctcaagggttgctttatgtttgggggtttgtactgcaagagttagtttctgatatagcaatggtgata
gtatagtcttctaccatgaactctatgccagcaagtacaggggtatatttcacatgggtgttttctgttcactgagtttcatgtcttc
tttgtatcttttgttttgttttgtgagacagggtttctctgtagcttttgagtcagtcctggaacttgctggccggccttgaactcaca
gagattcacctgcctctgcctcccaagtgctgggatttaaggtgtgagtcaccactgccaggttttttctttgtatcttgagtgaac
taaataggtaagctttaaataataatatgagcagtctatttatatacattaaatattaaatgcattgtgagatgagcatagccttt
gaggcccaggaacagaaagatttacttcacattgtaaatatactggtatacatacaaacgtacatacnnnnnnngtgtgtgt
gtgtgtgtgtgtgtgcatgccatagcacacatgtgaagtccagagtacagcattctcttttctacctttctgtagattcttgt
ggtcagagtcaggtcaaatcaaatcagacagatgcatgtataaaatgctcttacccactgaaccatcttgctgcttggtccaca
agcttagtggaagaatgctgggaagtgaatagtatgttttaaatgtagttaaccttgacttttgttgttgttgctgttattgagg
ccacattttcattgttctgagaaaatattactattttcctcagacagaattatatatttatttgaagttcatgaattccatattattttc
ctgtatttattacaaatagcatgcttaaacacttccaagtagtgaaacagctgctcatgtaggacacggattattgacagtgctg
ccatttatcagccagtaatccacttggcaggtagcacgctcatcgttatcctttatgcacacaaagccttgtttgaattttatcttt
aatgagtgtcaatgaaatggaaagagataagagttaaaaatacaacccaaactattgtatttacatttctcttttagaagaaac
ctaaagcagcattacttcttgcccatatttaataaataacatcatttacccttgttccctgcctccagactctcccatatactcctcttt
caattttattggccccttaaatgacatatcattacatgtatatccctacacataagtataaccagttcagtttgtataatgttacttg
catgtgttttcaatgctgatcatttggtagtggataaccaatggtgtgccctatgaaggggcagagtatttgtatcatgcttag
cattcctttgttgactgtaggattttgtttaaggttgaggtctcttggtctttccctgtctgcttctgcatgtccatggccatccttgtt
cagctcatgtttatgtagtcatgctgatgaggctttatggatgtagcttctgacattgctaagcaacacagtctcagcaaactccc
cagtcctctggttcttacaatctttccacactgtttcaccatgttgtctgagccttaggtgctgaagttgttttgtgtctgtatccattg
ggactaggctccacatgtctgcattttgattacttgtggttttctgtaacggtctctatgtgttgcaacgagaaggagtagttgctt
tgacgatgtgtaaagactatcttgtgggtataaggacaaatatttgcatgaagctatggattatgctggtctcaagcatgaactg
gataaattgtacagctcacacaaaacagctatagctagctgcacagtcaggcatgcactgatctgcttggggagttgttaacca
```

-continued aagggcttacatagctatgtatttctaagctctagttttactatcacaaagaaaattaattcacccttaattgtttaataagatgat atatcttagggaaaaaatgaaggtctttttttgacttatataaaagcttatgttttctacagttt exon2 (SEQ ID NO 32):
tgtcaaaagaacatgcctcgcaagtcctggtgaggaagcgccgcgcaaataccttgcttgaagaaactaaaaagggcaatct tgaaagagaatgcatcgaagagctctgcaataaagaggaagccagggaggtctttgaaaacaatcccgaaacg intron2 (SEQ ID NO 33):
gtaagagttcgtggaaatgaccaagtccacactcggatatatattggcagtcagaacactgccagcttgagctaccttgcttct gtttgaaagctaatgacttaggagttcatttctcatgtgttaccactgacatttcaggcaggctgccaatgacaggcactccagc caaactccatttcccttaagtctcattactcgcaactagtatcgactttataatgtgtgactattttattatcctaaccaaatctggta gccttgagggtgcaagagaagatgcgactgaagggtaagtgaccatatatgtacttgcattgtcactgtgcttttgttttggttg attgtgtttgagacagtctcttactctgtagctccaactacaaggagctccctatccatctgctttggcttcagcctcccaagtact gtgattatagactggtgtgtcttgccatttatctttaagaggctctagatagaaatggggccacctaactgagattagtcattaca gcattatgtatgctgactgtatactattctgtaaccttcatgaagtttcccgaggccactgataatcagcagtaatcattagtgtct aaaaatttccaagttacccacccgccaaacataacataaagacagcaacatgggactctttgtccattctgtgtttcaggagag ggcaatttatagtatgcttgtaactaacaggagtagcattaatatctccaaggagcactttgagcatgaccttgagagtctacat ggaacactgttcagggtctcctcagatgttctacctgagctgaattatacaatctggaggaaaagaaagagatgacatacaca aggctcctcctttgcctctgccacagctcccagaaccatgacaacagctgagtgataaagagcaaggactctttgtccatactta gaaaatttgtccccaactgtagctacttgtggtctgtggttgttattgtagctcttttttaatccctatgtgttctgataggttcaaag aagaaattttccccaaatatgcaacaattaaattttaatctacctagaattgagacaaaaatgtgacgaaataccttgatcaaa aaaacaactcaggaggaaagggtttttttttttttttggtttactaacctgaattgagggaagcaaaagtaggagctcaaacc aggtgggaacctggaggcaggagctgatgcagaggcatggaggagtgctgcttactggtctgctcctcatggcttgctcagct tgttttcttatagaacccagggccaccgtcacaaaagtaccatcacctgcaatgggttgggccttcccagggatctctgatta agaaaattccctacaggtctgtctacaattctttttgtttgtttgtttgtttgtttgtttgttttcgagacagggtttgtctgtata gctttggagcctgtcctggaactcactctgtagaccaggttggcctcgaagtcacaaagatccacctgcctttgcctccctagtgc tgggattaaaggcttgtgtcaccactgccaggcctattttaaggaagcatttttctccttgagattccttcctctcaaatgattctag cttgtatcaagttgacataaaattagccagcacagacaacaacaatagaaattttctatcctacacaatgtaataaatttattg ggtaggatttaacatatgtattctatgttttacattctcattctaaaaaggaatgtgtatgcactcttacaaacttccataatacaa aagaatacagtatgtattagatatgtgcatatattccttccctttatggaaagtttaaaaagtagaaagaatggtataatacct gcaacacaacacgtccctctaataagatcaaggctttcatttgattttgcctatccaccacatctaatcaatggttttgctttgagc aatcaagtcacatgattatattcccatacttgagttgtatatctgcattgtagatatgttctcaaagctcagccttttaaagagtag tagggagggaagatggaccacaggaagaaggggaggaaggtgaagaagaaaacacattcgtgtttctttaccttcacta atagttttgttgacagattccacctactccctgtccatatccctcatactcttaggccagtattcccagtgttattgaccctgatgttt acctgttcgcttgtcatcagcatgtcaccaatctttaaatgccattgtttgtctccttattgtcttgtctctgcttctgcagtaaacaac actgttgtctgaatgagtcagtgtcaggcccttcttataagccagtagaaacgtgcaagtttgtacatgataagaggaaaga gtgtagattttgatgtagaaaaagccaagctccactctaagccagaattttgaatactttttatgcagaaattttgtttttgtatga aatattcttgtgttatttatttacattatgagtgtactgtcagaagctcataaaaattaccctgttcataaaatacattccttcatcca tatgtcatcattattttgctatccatcaatatataaggaaggtgtttcacatgcattagatgcaataaggtaagtggtcatttttagtt ctctttaaatgatttcattgttgactccagtgtagatagtcatcatggcataagatgtatcaaatgaagactaggtgtggtggtgc ataccttcagtcccagcacacagaggcagaggaacatggattgctgtgagtttcaggtggacctggtctacatagtgagttcca aggtagatagagggtgtctcgagagaccctgtaagaaaagtctatgtttaattgccatgaaaaaattagaggattataaaga gggaatatattgttatagttatcaactacaaccagttcaaatcagaagctttaaaatgttattttattgttcagtagtgttttaagca -continued

```
tatatatgtatacacacaaacatatatgtgtttatatatatgtatatgtatactggtcaagtattggctatctattcttgaagtattta tagaaaaattagaaatgtgaaaacatacaacatgtaggtcatttccatattcatataaaagcaaattagaaaaattaatcttta actctgtagtgatatttgagtttgctaatatctatttttttattttctttctag
``` exon3 (SEQ ID NO 34):
```
gattatttttatccaaaatatttgg
```

Example 4

Transcription Factor Engineering

Expression of Protein S may be reduced or abolished by transcriptional down regulation of Protein S mRNA. Transcription factors can be designed to bind specific DNA elements in the promoter region of the CHO Protein S gene. Zinc finger proteins are ideal for such a manipulation and common procedures are reviewed by Wolfe-S A et al. Annu. Rev. Biophys. Struct. vol 3:183-212, 1999 and Jamieson-A C et al. Nature Reviews, vol 2:361-368, 2003. Typically a single zinc finger binds three bases adjacent to each other on the same DNA strand and a forth base on the complementary strand. Thus, several zinc fingers can be combined in order to bind a desired DNA element. Recognition of a DNA element of 15-18 base pairs, which actually can be universal in the genome, needs a combination of 5-6 zinc fingers.

A DNA element having the sequence GGAGAG-GAGGGGGGG (SEQ ID NO 35) from the CHO Protein S promoter are chosen and Zinc finger proteins binding the DNA element is predicted based on the publications by Liu-P Q et al., Journal of Biological Chemistry, Vol. 276 (14), pp. 11323-11334, 2001 and Zhang-L et al. Journal of Biological Chemistry, Vol. 275 (43), pp. 33850-33860, 2000. A synthetic five zinc finger protein based on SP1 and BTEB4 is made by PCR from overlapping oligonucleotides as described in Zhang-L et al. Journal of Biological Chemistry, Vol. 275 (43), pp. 33850-33860, 2000: Zinc finger 5 CXXCXXXXXQS-GHLQRHXXXH (SEQ ID NO 36) interacts with GGAg; zinc finger 4 CXXXXCXXXXXRSDNLARHXXXH (SEQ ID NO 37) interacts with GAGg; zinc finger 3 CXX-CXXXXXRSDNLTRHXXXH (SEQ ID NO 38) interacts with GAGg; zinc finger 2 CXXXXCXXXXXRSDHL-TRHXXXH (SEQ ID NO 39) interacts with GGGg; zinc finger 1 CXXXXCXXXXXRSDHLARHXXXH (SEQ ID NO 40) interacts with GGGa; and N-terminal to the zinc fingers the KRAB domain of KOX1 is inserted.

Upon binding of the engineered zinc finger protein to the GGAGAGGAGGGGGGG (SEQ ID NO 41) DNA element the CHO Protein S transcription was expected to be downregulated.

The CHO Protein S promoter region (SEQ ID NO 29) was cloned into pGL3-basic (Promega, Madison) and was used as reporter construct in a luciferase reporter assay to determine the effect of ZNF-PS. The plasmid encoding the ZNF-PS gene and the CHO Protein S reporter plasmid were transfected into CHO-K1 cells and luciferase activity was determined. ZNF-PS can downregulate Protein S transcription 50% in a dose-response independent manner. FIG. 3a illustrates ZNF-PS downregulation of Protein S. In a similar experiment the CHO-K1 cells were transfected with ZNF-PS and pEGFP (Enhanced Green Flourescent Protein) and Protein S and pEGFP mRNA were determined by real-time PCR. pEGFP served as transfection control. FIG. 3b shows a downregulation of Protein S by 50%.

ZNF-PS
(SEQ ID NO 42)
```
Mdaksltawsrtlvtfkdvfvdftreewklldtaqqivyrnvmlenyknl vslgyqltkpdvilrlekgeepwlvereihqethpdsetafeikssvssr sifkdkqscdikmegmarndlwylsleevwkpgkkkqhichiqgcgkvyg rsdhlarhlrwhtgerpfmctwsycgkrftrsdhltrhkrthtgekkfac pecpkrfmrsdnltrhikthtgerpfacdwqgcdkkfarsdnlarhhrth tgekrfscplcskrftqsghlqrharrhpgfhpdllrrpgarstspsdsl pcslagspapspapspapagl
```

Example 5

Determination of Numbers of Protein S Alleles in the CHO K1 Genome

The CHO-K1 cell line has only 21 chromosomes, compared to the Chinese Hamster which has 22 chromosomes, and only 8 of these 21 are normal. In the 13 altered chomosomes translocations, deletions, and pericentric inversions have been detected (Deaven & Petersen, Chromosoma 1973; 41(2), 129-144). It is not known whether the Protein S gene is present on normal or altered chromosomes or how many alleles are present in the CHO-K1 genome.

The SeeDNA Biotech Inc. company performed a FISH (Flourescence In Situ Hybridization) analysis on the genome of CHO K1 cells (ATCC# CCL-61) using a plasmid containing the Protein S Intron 1 probe (SEQ ID NO 43) in pCR2.1 (Invitrogen, Carlsbad) cloned and supplied by us. The results of the FISH analysis is shown i FIG. 4. The Protein S gene is localized onto two different chromosomes in the same metaphase. The chromosome with locus A (shown by an arrow) is submetacentric and of smaller size. The chromosome with locus B (shown by an arrowhead) is metacentric and of bigger size. The banding pattern of these two chromosomes is also different.

The Protein S Intron 1 probe
(SEQ ID NO 43)
```
ctgctggtatgcctagccctggtgctgccagcctcggagacaaactgtaagtaatccatacctcctggcttctccattccctatgt gccccggcttgaagattttccactaggctgtttgctgcctcctaagtttccagtaagtccgccaccattcagagagtcgcggcag
```

-continued

```
cctgggtctggtgggcagtgtaaaggtgggacaggatcaaagcttgccttgctttgagaaccattgtccacaggacttgattcc
agaacccgggtgacactaagtgtcaaaggaattgcttgaacatagtcctaaatattgctaggaaagctaagtcaagcctgttg
ccctcctcccgtttacaagagtgccccagcccgcaccctctcctgcggctaaccttccttttgcaatttctggactttgaacttgatt
gactggtctcacattgacaaactgtttggggactgctggggtgttacatatgattctctaaccttgatataagaaatagctgttgg
atgttaccttgtaccgaggatcattttctgagggttttgactgttgccgctttgagatggcagcaagaattctgtacaacacacac
attttgtgtttcttggtcttttcctcttcccattctcagattccgggcagtatatcgagttttctcttagaaatataaaacgaaccaca
aggttttagtacattttaatggtcaattaaattgtttttagaagctttaaatatgttcataattaacactgctttcttttgctcttttgtag
tcccagtcactggcatgggagcaataactgtataacaaataccacttaggtcactgcgagcaccaaagaaacttttcaaagat
ggtaattaagtaggagtttgctggaattgcaagttttttattaattagtaaggaatctagcctgatatttttaaatgtctaactaagt
taaagaccagaatgaaactggttcacttttttattgaggataaacaagttacagttataaagcctcaacaatcaaagccctacga
tgaagcagcgtgtgactgtatgcacatgatctatcttgttcagaggaacaatcaaacattttcagatagcatcagggcggtggt
ggtactcgcctataatcctagcaaagtcagaggcaagcagatctctgtgttcaaggccagcctagtctacagagtgagttccag
gacaactggggctacacagagaaacctgtctcagagaaaaacaaaataaaaccaaattcagatagctggtgtttgggaaaa
gagcaaaagacagcagtgctggccacacagagagtagacaagttcattctacaaggacatcacagaaagaatatgtgaccc
aatgacgaccataaactttcttgttcctgtgtcaaattatctccggtttattgatgaagaaccagacactatgagctgcgtctcctc
cttaagattttgttttggtgtcttgtttttgtcaagggggtttcattgtggccctgagcattagatccagggctttgtgcatgctaggc
cagggagctatattcccgaactccagaagactaggaatttgagatataaatagaatttgaattaccttctgtacaattgattgta
tggttctagaaatattgctatattaagggaagcctttgcagaagacagttattttgagatggtgcataacacaaaagaaatgaa
ctaaagcctgaggcctgctctgtagctctgccttgcccttagcctacaataactttctttacctttcaagcatgtgccaccacgcct
gactttcaggcccttcattttaacaagaaagcaagtattcagttatcaactgactttccaaatgcatttgtatgaataaaaactac
aaaaatataaaataagaactatacacacaaaagccttgtatttaaaatttacgctgtggacatattttgctcatcattcgtgag
agcttgcggtaaaaaggcaaggggaagaggaggatatctattttgggtaggctaatttggccttatccagacttccctttttgg
gtggatgcagtctgcccagcacactattggcccatttcttctacatggctttgtgctctgctctgcccttagctaattgtcccctttga
catgcttttgtctttccttaaagtttctatacttcaaaaaccatcccgctacactaatggagtgattttctcaagggttgctttatgttt
ggggtttgtactgcaagagttagtttctgatatagcaatggtgatagtatagtcttctaccatgaactctatgccagcaagtaca
ggggtatatttcacatgggtgttttctgttcactgagtttcatgtcttctttgtatcttttgttttgttttgtgagacagggtttctctgt
agcttttgagtcagtcctggaacttgctggccggccttgaactcacagagattcacctgcctctgcctcccaagtgctgggattta
aggtgtgagtcaccactgccaggttttttctttgtatcttgagtgaactaaataggtaagctttaaataataatatgagcagtctat
ttatatacattaaatattaaatgcattgtgagatgagcatagcctttgaggcccaggaacagaaagatttacttcacattgtaaa
tatactggtatacatacaaacgtacatacnnnnnnngtgtgtgtgtgtgtgtgtgtgtgtgtgcatgccatagcacacatgtg
aagtccagagtacagcattctcttttttctacctttctgtagattcttgtggtcagagtcaggtcaaatcaaatcagacagatgcat
gtataaaatgctcttacccactgaaccatcttgctgcttggtccacaagcttagtggaagaatgctgggaagtgaatagtatgtt
tttaaatgtagttaaccttgacttttttgttgttgttgctgttattgaggccacattttcattgttctgagaaaatattactattttcctca
gacagaattatatatttatttgaagttcatgaattccatattattttcctgtatttattacaaatagcatgcttaaacacttccaagta
gtgaaacagctgctcatgtaggacacggattattgacagtgctgccatttatcagccagtaatccacttggcaggtagcacgct
catcgttatcctttatgcacacaaagccttgtttgaattttatcttttaatgagtgtcaatgaaatggaaagagataagagttaaa
aatacaacccaaactattgtatttacattttctcttttagaagaaacctaaagcagcattacttcttgcccatatttaataaataaca
tcatttaccccttgttccctgcctccagactctcccatatactcctctttcaattttattggcccctttaaatgacatatcattacatgtat
atccctacacataagtataaccagttcagtttgtataatgttacttgcatgtgtgttttcaatgctgatcatttggtagtggataacc
aatggtgtgccctatgaaggggcagagtatttgtatcatgcttagcattcctttgttgactgtaggattttgtttaaggttgaggtc
```

```
                                           -continued
tcttggtctttccctgtctgcttctgcatgtccatggccatccttgttcagctcatgtttatgtagtcatgctgatgaggctttatgga tgtagcttctgacattgctaagcaacacagtctcagcaaactccccagtcctctggttcttacaatctttccacactgtttcaccatg ttgtctgagccttaggtgctgaagttgttttgtgtctgtatccattgggactaggctccacatgtctgcattttgattacttgtggtttt ctgtaacggtctctatgtgttgcaacgagaaggagtagttgctttgacgatgtgtaaagactatcttgtgggtataaggacaaat atttgcatgaagctatggattatgctggtctcaagcatgaactggataaattgtacagctcacacaaaacagctatagctagct gcacagtcaggcatgcactgatctgcttggggagttgttaaccaaagggcttacatagctatgtattttctaagctctagttttac tatcacaaagaaaattaattcacccttaattgtttaataagatgatatatcttagggaaaaaatgaaggtctttttttgacttatat aaaagcttatgttttctacagttttgtcaaaagaacatgcctcgcaagtcctggtgaggaagcgccgcgcaaataccttgcttga agaaactaaaaagggcaatcttgaaagagaatgcatcgaagagctctgc
```

Example 6

Gene Targeting of CHO Protein S Enhanced by Zinc Finger-Nuclease Fusion Proteins Gene targeting by homologous recombination is hard and laborious work because the somatic recombinations that takes place in mammalian cells not very often are homologous. However, site-specific cleavage of the DNA strands can enhance homologous recombination. Engineering of DNA binding zinc fingers fused to endonucleases makes it possible to design almost exactly where the DNA cleavage should occur (Durai et al., Nucleic Acids Research, 2005; 33(18), 5970-5990 and Smith et al., Nucleic Acids Research, 2000; 28(17), 3361-3369). Two zinc finger proteins, designed to bind 5'-GTCCTGAGC-3' (right finger) and 5'-GCTGG-TATG-3' (left finger) elements, were made in the framework published by Mani et al. (Mani et al., Biochemical and Biophysical Research Communications 2005, 335; 447-457). Zinc finger DNA binding specificity of zinc finger has previously been described by (Rebar-E3, et al. Nature Medicine 8 (2002) 1427-1432; Liu-P Q, et al. Journal of Biological Chemistry 276 (2001) 11323-11334; Ren-D, et al. Genes & Development 16 (2002) 27-32; Mani-M, et al Biochemical and Biophysical Research Communications 335 (2005) 447-457).

The right and left zinc finger were both either fused to the nuclease domain of Fok I and Sts I restriction enzyme (SEQ ID NO 44-51). Fok I and Sts I restriction enzyme needs to homodimerize to be able to cleave DNA, which also increase the specificity of the zinc finger pair. The function of the engineered nucleases are illustrated in FIGS. 5 and 6. When the genomic DNA has been cleaved by the zinc finger nucleases the repair mechanism will seek to repair the gap, very likely by homologous recombination. The gene targeting construct (SEQ ID NO 52) devoid of the Protein S gene will be transfected along with the nucleases. In the place of Protein S exon 1 in the genome the EGFP gene will be inserted. FIG. 6 illustrates the flow scheme of the homologous recombination. The gene targeting construct was made by exchanging the luciferase gene in the Protein S reporter construct (example 4) by the EGFP-gene and further inserting Protein S intron 1 after the poly A signal. The construct consists of Protein S promoter, EGFP-gene, PolyA-signal and Protein S intron1, no exon1. The homozygous recombinant CHO cell line will express EGFP and not Protein S because the Protein S signal peptide has been deleted and the transcript will be truncated right after the EGFP coding sequence due to the PolyA signal. Heterozygous cell clones are expected to be most abundant and a PCR analysis will reveal whether we have succeeded to make a homozygous cell clone. A heterozygous cell clone can be treated a second time with a targeting vector containing an antibiotical resistance gene in place of the EGFP gene to facilitate selection.

```
Left zinc finger-Fok I DNA sequence
                                                                    (SEQ ID NO 44)
atgaagctactgtcttctatcgaacaagcatgcccaaaaaagaagagaaaggtagatgaaaaaccttacaagtgtccggaat gtgggaagtcctttagtcggagcgacaacctggcccggcaccagcggacgcataccggtgagaagccctacaaatgcccag aatgcggaaaatcattttcgcggagcagcaacctgcgggagcaccaacgaacccacacaggcgagaaaccatttaaatgtc ctgagtgtggtaagagctttagccggagcgacaacctgacccggcatcaagctactcatacgggcggcggtggcagcggtg gcggtagcggcggtggcagcggtggcggatcccaactagtcaaaagtgaactggaggagaagaaatctgaacttcgtcata aattgaaatatgtgcctcatgaatatattgaattaattgaaattgccagaaattccactcaggatagaattcttgaaatgaaggt aatggaattttttatgaaagtttatggatatagaggtaaacatttgggtggatcaaggaaaccggacggagcaatttatactgt cggatctcctattgattacggtgtgatcgtggatactaaagcttatagcggaggttataatctgccaattggccaagcagatga aatgcaacgatatgtcgaagaaaatcaaacacgaaacaaacatatcaaccctaatgaatggtggaaagtctatccatcttctg taacggaatttaagttttatttgtgagtggtcactttaaaggaaactacaaagctcagcttacacgattaaatcatatcactaatt
```

-continued gtaatggagctgttcttagtgtagaagagcttttaattggtggagaaatgattaaagccggcacattaaccttagaggaagtga gacggaaatttaataacggcgagataaacttttag Left zinc finger-Sts I DNA sequence (SEQ ID NO 45)

atgaagctactgtcttctatcgaacaagcatgcccaaaaaagaagagaaaggtagatgaaaaaccttacaagtgtccggaat gtgggaagtcctttagtcggagcgacaacctggcccggcaccagcggacgcataccggtgagaagccctacaaatgcccag aatgcggaaaatcattttcgcggagcagcaacctgcgggagcaccaacgaacccacacaggcgagaaaccatttaaatgtc ctgagtgtggtaagagctttagccggagcgacaacctgacccggcatcaagctactcatacgggcggcggtggcagcggtg gcggtagcggcggtggcagcggtggcggatccgtattagaaaaaagtgatattgaaaaatttaagaatcaattgcgtacgga actaaccaatattgaccattcttatcttaaaggaattgatatagctagtaaaaagaaaaccagtaatgttgaaaatacggaattt gaagcaatatcaaccaagattttttacggatgagtttgggttttttcaggcaaacatctaggaggaagcaacaaaccagatggact cctgtgggatgatgattgtgcaattattcttgattcaaaagcttactcagaaggctttccactcactgcctcccacacagatgctat gggaagatatttgaggcaatttacagagcgaaaagaagaaataaagccaacgtggtgggatattgctccagaacatttaga caatacatatttcgcttacgtttctgggagttttcgggtaattataaggaacagttacaaaaatttaggcaagatacaaaccatt taggtggggcactagagtttgttaaattgttattactagcaaataattataaaactcaaaaaatgagtaaaaaagaagttaag aaaagtattcttgattataatatttcatatgaagaatatgctccattacttgcagaaatagagtaa Right zinc finger-Fok I DNA sequence (SEQ ID NO 46)

atgaagctactgtcttctatcgaacaagcatgcccaaaaaagaagagaaaggtagatgaaaaaccttacaagtgtccggaat gtgggaagtcctttagtcggagcgacgccctgacccagcaccagcggacgcataccggtgagaagccctacaaatgcccag aatgcggaaaatcattttcgcagagcagccacctggcccggcaccaacgaacccacacaggcgagaaaccatttaaatgtcc tgagtgtggtaagagctttagccagagcagccacctgacccggcatcaagctactcatacgggcggcggtggcagcggtggc ggtagcggcggtggcagcggtggcggatcccaactagtcaaaagtgaactggaggagaagaaatctgaacttcgtcataaa ttgaaatatgtgcctcatgaatatattgaattaattgaaattgccagaaattccactcaggatagaattcttgaaatgaaggtaa tggaattttttatgaaagtttatggatatagaggtaaacatttgggtggatcaaggaaaccggacggagcaatttatactgtcg gatctcctattgattacggtgtgatcgtggatactaaagcttatagcggaggttataatctgccaattggccaagcagatgaaat gcaacgatatgtcgaagaaaatcaaacacgaaacaaacatatcaaccctaatgaatggtggaaagtctatccatcttctgtaa cggaatttaagttttttatttgtgagtggtcactttaaaggaaactacaaagctcagcttacacgattaaatcatatcactaattgta atggagctgttcttagtgtagaagagcttttaattggtggagaaatgattaaagccggcacattaaccttagaggaagtgaga cggaaatttaataacggcgagataaacttttag Right zinc finger-Sts I DNA sequence (SEQ ID NO 47)

atgaagctactgtcttctatcgaacaagcatgcccaaaaaagaagagaaaggtagatgaaaaaccttacaagtgtccggaat gtgggaagtcctttagtcggagcgacgccctgacccagcaccagcggacgcataccggtgagaagccctacaaatgcccag aatgcggaaaatcattttcgcagagcagccacctggcccggcaccaacgaacccacacaggcgagaaaccatttaaatgtcc tgagtgtggtaagagctttagccagagcagccacctgacccggcatcaagctactcatacgggcggcggtggcagcggtggc ggtagcggcggtggcagcggtggcggatccgtattagaaaaaagtgatattgaaaaatttaagaatcaattgcgtacggaac taaccaatattgaccattcttatcttaaaggaattgatatagctagtaaaaagaaaaccagtaatgttgaaaatacggaatttg aagcaatatcaaccaagattttttacggatgagtttgggttttttcaggcaaacatctaggaggaagcaacaaaccagatggactc ctgtgggatgatgattgtgcaattattcttgattcaaaagcttactcagaaggctttccactcactgcctcccacacagatgctat gggaagatatttgaggcaatttacagagcgaaaagaagaaataaagccaacgtggtgggatattgctccagaacatttaga caatacatatttcgcttacgtttctgggagttttcgggtaattataaggaacagttacaaaaatttaggcaagatacaaaccatt -continued taggtggggcactagagtttgttaaattgttattactagcaaataattataaaactcaaaaaatgagtaaaaagaagttaag aaaagtattcttgattataatatttcatatgaagaatatgctccattacttgcagaaatagagtaa Left zinc finger-Fok I protein sequence (SEQ ID NO 48)

mkllssieqacpkkkrkvdekpykcpecgksfsrsdnlarhqrthtgekpykcpecgksfsrssnlrehqrthtgekpfkcpe cgksfsrsdnltrhqathtggggsgggsgggsgggsqlvkseleekkselrhklkyvpheyielieiarnstqdrilemkvmef fmkvygyrgkhlggsrkpdgaiytvgspidygvivdtkaysggynlpigqademqryveenqtrnkhinpnewwkvyps svtefkflfvsghfkgnykaqltrlnhitncngavlsveelliggemikagtltleevrrkfnngeinf Left zinc finger-Sts I protein sequence (SEQ ID NO 49)

mkllssieqacpkkkrkvdekpykcpecgksfsrsdnlarhqrthtgekpykcpecgksfsrssnlrehqrthtgekpfkcpe cgksfsrsdnltrhqathtggggsgggsgggsgggsvleksdiekfknqlrteltnidhsylkgidiaskkktsnventefeaist kiftdelgfsgkhlggsnkpdgllwdddcaiildskaysegfpltashtdamgrylrqfterkeeikptwwdiapehidntyfay vsgsfsgnykeqlqkfrqdtnhlggalefvkllllannyktqkmskkevkksildynisyeeyapllaeie Right zinc finger-Fok I protein sequence (SEQ ID NO 50)

mkllssieqacpkkkrkvdekpykcpecgksfsrsdaltqhqrthtgekpykcpecgksfsqsshlarhqrthtgekpfkcpe cgksfsqsshltrhqathtggggsgggsgggsgggsqlvkseleekkselrhklkyvpheyielieiarnstqdrilemkvmef fmkvygyrgkhlggsrkpdgaiytvgspidygvivdtkaysggynlpigqademqryveenqtrnkhinpnewwkvyps svtefkflfvsghfkgnykaqltrlnhitncngavlsveelliggemikagtltleevrrkfnngeinf Right zinc finger-Sts I protein sequence (SEQ ID NO 51)

mkllssieqacpkkkrkvdekpykcpecgksfsrsdaltqhqrthtgekpykcpecgksfsqsshlarhqrthtgekpfkcpe cgksfsqsshltrhqathtggggsgggsgggsgggsvleksdiekfknqlrteltnidhsylkgidiaskkktsnventefeaist kiftdelgfsgkhlggsnkpdgllwdddcaiildskaysegfpltashtdamgrylrqfterkeeikptwwdiapehldntyfay vsgsfsgnykeqlqkfrqdtnhlggalefvkllllannyktqkmskkevkksildynisyeeyapllaeie Protein S promoter-EGFP-Protein S intron 1 targeting construct (SEQ ID NO 52)

ggtaccgagctcttacgcgtgctagcccgggctcgagatctcaaccccttttgaccatacacatttctactctttgtgtttgctgga gctgttttctccccacactcaaccccctttgctgaagcctggaacttgcttttccacagcttaagttgttataggtttcaatcatctgtc cacctccctgactttcataattttgtgaaataccttgcatatatatgggactaaatattattttctcctggttgtccataatagat taatttaattcctaaacaaagaacagaacatagattggtatagtagaagagtttcccttctccctactgcatgaatggaaattcc ccaaaccatccttatcagagaaattaactcacatactagtcaccttttcattcagctggatgacaaaatcattttaaaaaaagaga ataaagaaaacagataagaacaactagatctaggaataatacttaaaatatgattctgcttagtaggtttcattcacacaccta gaaaaaaaaatcagtcaatgtttcctttgggcagaaaatgagcaataatgggtatgcattgaccactactgttggacatagcct tattgcttcatatagcatctattcaaagtctcagatcaacactatgaaaacctgtcatctctgtattagatgatgtgactggggctg taaagggtaagctcttttcttacagctatacaacaacgctaagaccaagttctgtgctttgagcccaggcagtttagtttcccagg agcaacctaaagcctgattcacaggcatatgtatgatccaaactgaatggtagtacatcaataccaaaacaatctattggtgga aacacaccataggtgatcgaaatactccatttctttcctctcatgacttctgttctgagcagtcctcttcctaaagtctacattgtc ttctgagttcaggctgacatcttgacatcctcctggctggcacagtctctggacaaggagggaagaaggagagaaggggaaa gggagaggagggggggagggagagaaagaatgggaagaggaaggatatgaaagagagaagagaggagggaaggcg ggaggaagggagggagggagggagggagagagggagagagggagagagagagagagagagagagagagagagag agagagagagagagagagagagagggagagggagagagacagagagagagagggagagggagagagag agagagagagagagagagagagagagagtgaggagagagagagagagttttcttcaccattggacattcct aaagaaaagaagtaaatgcaggattggggacagtgacagaggacctctgataaactttctgaggcctctgacctcactctctc -continued

```
ggagccctcctccaccacccacccccccctccctagctgagaaaagcttccaggaaatgtcccagtcatcgcttccctcccgg gctgggggctgggagcgggcggtcccctcaggccaggctgctccggccgcgctcgggcagggccacaacagagctggga aagctgagcccaggctcgcagctcctctgggcggagcgccggctcggtcccgctgcgccagccgtgatccccggcagcctg ctcagccatggtgagcaagggcgaggagctgttcaccggggtggtgcccatcctggtcgagctggacggcgacgtaaacgg ccacaagttcagcgtgtccggcgagggcgagggcgatgccacctacggcaagctgaccctgaagttcatctgcaccaccggc aagctgcccgtgccctggcccaccctcgtgaccaccctgacctacggcgtgcagtgcttcagccgctaccccgaccacatgaag cagcacgacttcttcaagtccgccatgcccgaaggctacgtccaggagcgcaccatcttcttcaaggacgacggcaactacaa gacccgcgccgaggtgaagttcgagggcgacacccttggtgaaccgcatcgagctgaagggcatcgacttcaaggaggacg gcaacatcctggggcacaagctggagtacaactacaacagccacaacgtctatatcatggccgacaagcagaagaacggca tcaaggtgaacttcaagatccgccacaacatcgaggacggcagcgtgcagctcgccgaccactaccagcagaacacccccat cggcgacggccccgtgctgctgcccgacaaccactacctgagcacccagtccgccctgagcaaagaccccaacgagaagcg cgatcacatggtcctgctggagttcgtgaccgccgccgggatcactctcggcatggacgagctgtacaagtaaagcggccgc gactctagagtcggggcggccggccgcttcgagcagacatgataagatacattgatgagtttggacaaaccacaactagaat gcagtgaaaaaaatgctttatttgtgaaatttgtgatgctattgcttttatttgtaaccattataagctgcaataaacaagttaaca acaacaattgcattcattttatgtttcaggttcaggggaggtgtgggaggttttttaaagcaagtaaaacctctacaaatgtgg taaaatcgataaggatcctgctggtatgcctagccctggtgctgccagcctcggagacaaactgtaagtaatccatacctcctg gcttctccattccctatgtgccccggcttgaagattttccactaggctgtttgctgcctcctaagtttccagtaagtccgccaccatt cagagagtcgcggcagcctgggtctggtgggcagtgtaaaggtgggacaggatcaaagcttgccttgctttgagaaccattgt ccacaggacttgattccagaacccgggtgacactaagtgtcaaaggaattgcttgaacatagtcctaaatattgctaggaaag ctaagtcaagcctgttgccctcctcccgtttacaagagtgccccagcccgcaccctctcctgcggctaaccttccttttgcaatttct ggactttgaacttgattgactggtctcacattgacaaactgtttggggactgctggggtgttacatatgattctctaaccttgatat aagaaatagctgttggatgttaccttgtaccgaggatcattttctgagggttttgactgttgccgctttgagatggcagcaagaa ttctgtacaacacacacatttttgtgtttcttggtctttcctcttcccattctcagattccgggcagtatatcgagttttctcttagaaat ataaaacgaaccacaaggttttagtacattttaatggtcaattaaattgtttttagaagcttaaatatgttcataattaacactgct ttcttttgctcttttgtagtcccagtcactggcatgggagcaataactgtataacaaataccacttaggtcactgcgagcaccaaa gaaacttttcaaagatggtaattaagtaggagtttgctggaattgcaagttttattaattagtaaggaatctagcctgatattttt aaatgtctaactaagttaaagaccagaatgaaactggttcacttttttattgaggataaacaagttacagttataaagcctcaac aatcaaagccctacgatgaagcagcgtgtgactgtatgcacatgatctatcttgttcagaggaacaatcaaacattttcagata gcatcagggcggtggtggtactcgcctataatcctagcaaagtcagaggcaagcagatctctgtgttcaaggccagcctagtc tacagagtgagttccaggacaactggggctacacagagaaacctgtctcagagaaaacaaaataaaaccaaattcagata gctggtgtttgggaaaagagcaaaagacagcagtgctggccacacagagagtagacaagttcattctacaaggacatcaca gaaagaatatgtgacccaatgacgaccataaactttcttgttcctgtgtcaaattatctccggtttattgatgaagaaccagaca ctatgagctgcgtctcctccttaagattttgttttggtgtcttgtttttgtcaaggggtttcattgtggccctgagcattagatccagg gctttgtgcatgctaggccaggagctatattcccgaactccagaagactaggaatttgagatataaatagaatttgaattacct tctgtacaattgattgtatggttctagaaatattgctatattaagggaagcctttgcagaagacagttattttgagatggtgcata acacaaaagaaatgaactaaagcctgaggcctgctctgtagctctgccttgcccttagcctacaataactttctttacctttcaag catgtgccaccacgcctgactttcaggcccttcattttaacaagaaagcaagtattcagttatcaactgactttccaaatgcatttg tatgaataaaaactacaaaaatataaaaataagaactatacacaaaagccttgtatttaaaatttacgctgtggacatatttt gctcatcattcgtgagagcttgcggtaaaaggcaaaggggaagaggaggatatctattttgggtaggctaatttggccttatc cagacttcccttttgggtggatgcagtctgcccagcacactattggcccatttcttctacatggctttgtgctctgctctgcccttag
```

-continued

```
ctaattgtcccctttgacatgcttttgtctttccttaaagtttctatacttcaaaaaccatcccgctacactaatggagtgattttctca
agggttgctttatgtttggggtttgtactgcaagagttagtttctgatatagcaatggtgatagtatagtcttctaccatgaactct
atgccagcaagtacaggggtatatttcacatgggtgttttctgttcactgagtttcatgtcttctttgtatcttttttgttttgttttgtga
gacagggtttctctgtagcttttgagtcagtcctggaacttgctggccggccttgaactcacagagattcacctgcctctgcctcc
caagtgctgggatttaaggtgtgagtcaccactgccaggttttttctttgtatcttgagtgaactaaataggtaagctttaaataat
aatatgagcagtctatttatatacattaaatattaaatgcattgtgagatgagcatagcctttgaggcccaggaacagaaagat
ttacttcacattgtaaatatactggtatacatacaaacgtacatacnnnnnnngtgtgtgtgtgtgtgtgtgtgtgtgcatgc
catagcacacatgtgaagtccagagtacagcattctcttttctaccttctgtagattcttgtggtcagagtcaggtcaaatcaaa
tcagacagatgcatgtataaaatgctcttacccactgaaccatcttgctgcttggtccacaagcttagtggaagaatgctggga
agtgaatagtatgttttaaatgtagttaaccttgactttttgttgttgttgctgttattgaggccacattttcattgttctgagaaaat
attactattttcctcagacagaattatatatttatttgaagttcatgaattccatattattttcctgtatttattacaaatagcatgctta
aacacttccaagtagtgaaacagctgctcatgtaggacacggattattgacagtgctgccatttatcagccagtaatccacttgg
caggtagcacgctcatcgttatcctttatgcacacaaagccttgtttgaattttatctttttaatgagtgtcaatgaaatggaaaga
gataagagttaaaaatacaacccaaactattgtatttacatttctcttttagaagaaacctaaagcagcattacttcttgcccatat
ttaataaataacatcatttacccttgttccctgcctccagactctcccatatactcctctttcaattttattggccccctttaaatgacat
atcattacatgtatatccctacacataagtataaccagttcagtttgtataatgttacttgcatgtgtgttttcaatgctgatcatttg
gtagtggataaccaatggtgtgccctatgaaggggcagagtatttgtatcatgcttagcattcctttgtcgaccgatgcccttga
gagccttcaacccagtcagctccttccggtgggcgcggggcatgactatcgtcgccgcacttatgactgtcttctttatcatgcaa
ctcgtaggacaggtgccggcagcgctcttccgcttcctcgctcactgactcgctgcgctcggtcgttcggctgcggcagcggt
atcagctcactcaaaggcggtaatacggttatccacagaatcaggggataacgcaggaaagaacatgtgagcaaaaggcca
gcaaaaggccaggaaccgtaaaaaggccgcgttgctggcgtttttccataggctccgcccccctgacgagcatcacaaaaatc
gacgctcaagtcagaggtggcgaaacccgacaggactataaagataccaggcgtttccccctggaagctccctcgtgcgctct
cctgttccgaccctgccgcttaccggatacctgtccgcctttctcccttcgggaagcgtggcgctttctcatagctcacgctgtagg
tatctcagttcggtgtaggtcgttcgctccaagctgggctgtgtgcacgaaccccccgttcagcccgaccgctgcgccttatccg
gtaactatcgtcttgagtccaacccggtaagacacgacttatcgccactggcagcagccactggtaacaggattagcagagcg
aggtatgtaggcggtgctacagagttcttgaagtggtggcctaactacggctacactagaagaacagtatttggtatctgcgct
ctgctgaagccagttaccttcggaaaaagagttggtagctcttgatccggcaaacaaaccaccgctggtagcggtggtttttttg
tttgcaagcagcagattacgcgcagaaaaaaaggatctcaagaagatcctttgatcttttctacggggtctgacgctcagtgga
acgaaaactcacgttaagggattttggtcatgagattatcaaaaaggatcttcacctagatccttttaaattaaaaatgaagtttt
aaatcaatctaaagtatatatgagtaaacttggtctgacagttaccaatgcttaatcagtgaggcacctatctcagcgatctgtct
atttcgttcatccatagttgcctgactccccgtcgtgtagataactacgatacgggagggcttaccatctggccccagtgctgca
atgataccgcgagacccacgctcaccggctccagatttatcagcaataaaccagccagccggaagggccgagcgcagaagt
ggtcctgcaactttatccgcctccatccagtctattaattgttgccgggaagctagagtaagtagttcgccagttaatagtttgcg
caacgttgttgccattgctacaggcatcgtggtgtcacgctcgtcgtttggtatggcttcattcagctccggttcccaacgatcaa
ggcgagttacatgatccccatgttgtgcaaaaaagcggttagctccttcggtcctccgatcgttgtcagaagtaagttggccgc
agtgttatcactcatggttatggcagcactgcataattctcttactgtcatgccatccgtaagatgcttttctgtgactggtgagta
ctcaaccaagtcattctgagaatagtgtatgcggcgaccgagttgctcttgcccggcgtcaatacgggataataccgcgccaca
tagcagaactttaaaagtgctcatcattggaaaacgttcttcggggcgaaaactctcaaggatcttaccgctgttgagatccagt
tcgatgtaacccactcgtgcacccaactgatcttcagcatcttttactttcaccagcgtttctgggtgagcaaaaacaggaaggc
aaaatgccgcaaaaaagggaataagggcgacacggaaatgttgaatactcatactcttcctttttcaatattattgaagcattta
```

-continued

```
tcagggttattgtctcatgagcggatacatatttgaatgtatttagaaaaataaacaaatagggggttccgcgcacatttccccga aaagtgccacctgacgcgccctgtagcggcgcattaagcgcggcgggtgtggtggttacgcgcagcgtgaccgctacacttg ccagcgccctagcgcccgctcctttcgctttcttcccttcctttctcgccacgttcgccggctttccccgtcaagctctaaatcgggg gctccctttagggttccgatttagtgctttacggcacctcgaccccaaaaaacttgattagggtgatggttcacgtagtgggccat cgccctgatagacggttttcgccctttgacgttggagtccacgttctttaatagtggactcttgttccaaactggaacaacactca accctatctcggtctattcttttgatttataagggattttgccgatttcggcctattggttaaaaaatgagctgatttaacaaaaatt taacgcgaattttaacaaaatattaacgcttacaatttgccattcgccattcaggctgcgcaactgttgggaagggcgatcggtg cgggcctcttcgctattacgccagcccaagctaccatgataagtaagtaatattaaggtacgggaggtacttggagcggccgc aataaaatatctttattttcattacatctgtgtgttggttttttgtgtgaatcgatagtactaacatacgctctccatcaaaacaaaa cgaaacaaacaaactagcaaaataggctgtccccagtgcaagtgcaggtgccagaacatttctctatcgata.
```

The invention claimed is:

1. An amino acid sequence comprising the sequence of SEQ ID NO 3.

* * * * *

SEQUENCE LISTING

<160> NUMBER OF SEQ ID NOS: 52

<210> SEQ ID NO 1
<211> LENGTH: 23
<212> TYPE: DNA
<213> ORGANISM: Artificial
<220> FEATURE:
<223> OTHER INFORMATION: Synthetic

<400> SEQUENCE: 1
gcccaggctc gcagctcctc tgg    23

<210> SEQ ID NO 2
<211> LENGTH: 23
<212> TYPE: DNA
<213> ORGANISM: Artificial
<220> FEATURE:
<223> OTHER INFORMATION: Synthetic

<400> SEQUENCE: 2
caggtgacac ctgccagctg gtg    23

<210> SEQ ID NO 3
<211> LENGTH: 2306
<212> TYPE: DNA
<213> ORGANISM: Artificial
<220> FEATURE:
<223> OTHER INFORMATION: Synthetic

<400> SEQUENCE: 3
gcccaggctc gcagctcctc tgggcggagc gccggctcgg tccccgctgc gccagccgtg    60
atccccggca gcctgctcag caatgagggt cctgagcgcg cgctgtcggc tactgctggt    120
atgcctagcc ctggtgctgc cagcctcgga gacaaacttt ttgtcaaaag aacatgcctc    180
gcaagtcctg gtgaggaagc gccgcgcaaa taccttgctt gaagaaacta aaaagggcaa    240
tcttgaaaga gaatgcatcg aagagctctg caataaagag gaagccaggg aggtctttga    300
aaacaatccc gaaacggatt attttttatcc aaaatatttg ggttgtctgg gcatgttccg    360
tgctggcctg ttcagtgctg cgcggcagtc tgttaatgct taccccgacc tcaggagctg    420
tgtcaatgcc atcccagacc aatgtgatcc tatgccatgc aatgaagatg ggtatctgag    480
ctgcaaagat ggccaagctg ctttcacatg catctgcaaa ccaggatggc aaggggacaa    540
```

| | |
|---|---|
| atgccagttt gatgtaaatg aatgtaaaga tcccttaaat gtaaatgggg gctgcagcca | 600 |
| gatttgtgac aacactcctg gaagttacca ctgctcctgc agaagtggct ttgctatgct | 660 |
| ttcaaacaaa aaagactgca aagatgtgga tgaatgctct atgaagccca gtgtttgtgg | 720 |
| ctcagctgtg tgcaagaaca ctccaggaga ctatgagtgt gaatgtcctg acggctacag | 780 |
| atatgatccc tcatcgaagt cttgcaaaga tgtggacgaa tgctctgaga catgtgtgc | 840 |
| tcaattgtgt gtcaattacc ctggaggcta ctcttgttac tgtgatggaa agaaaggatt | 900 |
| caagcttgcc caagatcaga agagttgtga gggtattcca gtgtgccttc ccttgaacct | 960 |
| tgacaaaaat tatgaattat tgtacttggc tgagcagttt gtaggagttg tcttatatct | 1020 |
| gaaatttcgt ttgccagaaa ttaccagatt ttcagctgaa tttgattttc ggacatatga | 1080 |
| ttcagagggc atcatcctgt atgcagaatc tcttgatcac tcaaattggc tcctgattgc | 1140 |
| acttcgtgat ggaaaaattg aagttcagtt taagaatgag ttttcaaccc aaatcacaac | 1200 |
| cggaggcaat gttattaaca atggtaaatg aacatggta tccgtggaag aattagacga | 1260 |
| cagtgttagc attaaaatag ctaaagaagc tgtgatgaat ataaataaat ttgggagcct | 1320 |
| ctttaaacct acagatggat ttctggacac caaaatatac tttgcaggat tacctcgggt | 1380 |
| agtggaaagt gcactcatta aaccgattaa ccctcgtctg gatggatgta tacgaggctg | 1440 |
| gaacttgatg aaacaaggag ctttaggtgc aaaggaaatt attcaaggaa acaaaataa | 1500 |
| gcattgcttc ctcatggtgg agaagggctc ctactaccct ggttctggaa ttgctcggtt | 1560 |
| cagcatagat tacaataatg taaccaatgc agagggctgg caaataaatg tgaccttgaa | 1620 |
| tattcgtcca tccactggca ctggaattat gcttgccttg gtttctggag acaaagtgcc | 1680 |
| ctttgccttg tccttggtgg gctccagctc tgaaaattct caggatattg tggtatttgt | 1740 |
| tgaaaattca gtggtggctc gaatggaggc cataactctg tgttctgacc agcaatccca | 1800 |
| actgaaatgt aatgttaaca gacatggcct agagctatgg agcccactga gaaagatgt | 1860 |
| catctactct aaagatattc aaggacaact agcagtcttg gacaaagcaa tgaaaggaaa | 1920 |
| cgtggccact tatctgggtg gcattccaga tctttccttc agtgccacgc cagtgaatgc | 1980 |
| cttctacagt ggctgcatgg aagtgaacat caacgggggtg cagttggatc tggatgaagc | 2040 |
| catttctaaa cataatgaca tcagagctca ctcatgtcct tcagttaaga aaatccagaa | 2100 |
| gaacgtctaa tgtctgtttt ctgtgcttat aatgcccctt tccttgtaat tatgctcacg | 2160 |
| cccctatcac cagctggcag gtgtcacctg tgaagtgcaa tgtttgaaat gatgtggtac | 2220 |
| tttgtccttc agatttttgt tatataaacc acgttttttt tttttttta aagtctttct | 2280 |
| tctattgctg tctagaaatt aaataa | 2306 |

<210> SEQ ID NO 4
<211> LENGTH: 2028
<212> TYPE: DNA
<213> ORGANISM: Artificial
<220> FEATURE:
<223> OTHER INFORMATION: Synthetic

<400> SEQUENCE: 4

| | |
|---|---|
| atgagggtcc tgagcgcgcg ctgtcggcta ctgctggtat gcctagccct ggtgctgcca | 60 |
| gcctcggaga caaacttttt gtcaaaagaa catgcctcgc aagtcctggt gaggaagcgc | 120 |
| cgcgcaaata ccttgcttga agaaactaaa aagggcaatc ttgaaagaga atgcatcgaa | 180 |
| gagctctgca ataaagagga agccaggggag gtctttgaaa acaatcccga aacggattat | 240 |
| ttttatccaa atatttgggg ttgtctgggc atgttccgtg ctggcctgtt cagtgctgcg | 300 |

```
cggcagtctg ttaatgctta ccccgacctc aggagctgtg tcaatgccat cccagaccaa    360
tgtgatccta tgccatgcaa tgaagatggg tatctgagct gcaaagatgg ccaagctgct    420
ttcacatgca tctgcaaacc aggatggcaa ggggacaaat gccagtttga tgtaaatgaa    480
tgtaaagatc ccttaaatgt aaatggggc tgcagccaga tttgtgacaa cactcctgga    540
agttaccact gctcctgcag aagtggcttt gctatgcttt caaacaaaaa agactgcaaa    600
gatgtggatg aatgctctat gaagcccagt gtttgtggct cagctgtgtg caagaacact    660
ccaggagact atgagtgtga atgtcctgac ggctacagat atgatccctc atcgaagtct    720
tgcaaagatg tggacgaatg ctctgagaac atgtgtgctc aattgtgtgt caattaccct    780
ggaggctact cttgttactg tgatggaaag aaaggattca agcttgccca agatcagaag    840
agttgtgagg gtattccagt gtgccttccc ttgaaccttg acaaaaatta tgaattattg    900
tacttggctg agcagtttgt aggagttgtc ttatatctga aatttcgttt gccagaaatt    960
accagatttt cagctgaatt tgattttcgg acatatgatt cagagggcat catcctgtat   1020
gcagaatctc ttgatcactc aaattggctc ctgattgcac ttcgtgatgg aaaaattgaa   1080
gttcagttta agaatgagtt ttcaacccaa atcacaaccg gaggcaatgt tattaacaat   1140
ggtaaatgga acatggtatc cgtggaagaa ttagacgaca gtgttagcat taaaatagct   1200
aaagaagctg tgatgaatat aaataaattt gggagcctct ttaaacctac agatggatt    1260 ctggacacca aaatatactt tgcaggatta cctcgggtag tggaaagtgc actcattaaa   1320
ccgattaacc ctcgtctgga tggatgtata cgaggctgga acttgatgaa acaaggagct   1380
ttaggtgcaa aggaaattat tcaaggaaaa caaaataagc attgcttcct catggtggag   1440
aagggctcct actaccctgg ttctggaatt gctcggttca gcatagatta caataatgta   1500
accaatgcag agggctggca aataaatgtg accttgaata ttcgtccatc cactggcact   1560
ggaattatgc ttgccttggt ttctggagac aaagtgccct tgccttgtc cttggtgggc   1620 tccagctctg aaaattctca ggatattgtg gtatttgttg aaaattcagt ggtggctcga   1680
atggaggcca taactctgtg ttctgaccag caatcccaac tgaaatgtaa tgttaacaga   1740
catggcctag agctatggag cccactgaag aaagatgtca tctactctaa agatattcaa   1800
ggacaactag cagtcttgga caaagcaatg aaaggaaacg tggccactta tctgggtggc   1860
attccagatc tttccttcag tgccacgcca gtgaatgcct tctacagtgg ctgcatggaa   1920
gtgaacatca acgggtgca gttggatctg gatgaagcca tttctaaaca taatgacatc   1980
agagctcact catgtcctc agttaagaaa atccagaaga acgtctaa               2028
```

<210> SEQ ID NO 5
<211> LENGTH: 675
<212> TYPE: PRT
<213> ORGANISM: Artificial
<220> FEATURE:
<223> OTHER INFORMATION: Synthetic

<400> SEQUENCE: 5

Met Arg Val Leu Ser Ala Arg Cys Arg Leu Leu Leu Val Cys Leu Ala
1               5                   10                  15

Leu Val Leu Pro Ala Ser Glu Thr Asn Phe Leu Ser Lys Glu His Ala
                20                  25                  30

Ser Gln Val Leu Val Arg Lys Arg Arg Ala Asn Thr Leu Leu Glu Glu
            35                  40                  45

Thr Lys Lys Gly Asn Leu Glu Arg Glu Cys Ile Glu Glu Leu Cys Asn
        50                  55                  60

```
Lys Glu Glu Ala Arg Glu Val Phe Glu Asn Asn Pro Glu Thr Asp Tyr
 65                  70                  75                  80

Phe Tyr Pro Lys Tyr Leu Gly Cys Leu Gly Met Phe Arg Ala Gly Leu
             85                  90                  95

Phe Ser Ala Ala Arg Gln Ser Val Asn Ala Tyr Pro Asp Leu Arg Ser
            100                 105                 110

Cys Val Asn Ala Ile Pro Asp Gln Cys Asp Pro Met Pro Cys Asn Glu
            115                 120                 125

Asp Gly Tyr Leu Ser Cys Lys Asp Gly Gln Ala Ala Phe Thr Cys Ile
130                 135                 140

Cys Lys Pro Gly Trp Gln Gly Asp Lys Cys Gln Phe Asp Val Asn Glu
145                 150                 155                 160

Cys Lys Asp Pro Leu Asn Val Asn Gly Gly Cys Ser Gln Ile Cys Asp
                165                 170                 175

Asn Thr Pro Gly Ser Tyr His Cys Ser Cys Arg Ser Gly Phe Ala Met
            180                 185                 190

Leu Ser Asn Lys Lys Asp Cys Lys Asp Val Asp Glu Cys Ser Met Lys
    195                 200                 205

Pro Ser Val Cys Gly Ser Ala Val Cys Lys Asn Thr Pro Gly Asp Tyr
210                 215                 220

Glu Cys Glu Cys Pro Asp Gly Tyr Arg Tyr Asp Pro Ser Ser Lys Ser
225                 230                 235                 240

Cys Lys Asp Val Asp Glu Cys Ser Glu Asn Met Cys Ala Gln Leu Cys
                245                 250                 255

Val Asn Tyr Pro Gly Gly Tyr Ser Cys Tyr Cys Asp Gly Lys Lys Gly
            260                 265                 270

Phe Lys Leu Ala Gln Asp Gln Lys Ser Cys Glu Gly Ile Pro Val Cys
    275                 280                 285

Leu Pro Leu Asn Leu Asp Lys Asn Tyr Glu Leu Leu Tyr Leu Ala Glu
290                 295                 300

Gln Phe Val Gly Val Val Leu Tyr Leu Lys Phe Arg Leu Pro Glu Ile
305                 310                 315                 320

Thr Arg Phe Ser Ala Glu Phe Asp Phe Arg Thr Tyr Asp Ser Glu Gly
            325                 330                 335

Ile Ile Leu Tyr Ala Glu Ser Leu Asp His Ser Asn Trp Leu Leu Ile
            340                 345                 350

Ala Leu Arg Asp Gly Lys Ile Glu Val Gln Phe Lys Asn Glu Phe Ser
            355                 360                 365

Thr Gln Ile Thr Thr Gly Gly Asn Val Ile Asn Asn Gly Lys Trp Asn
    370                 375                 380

Met Val Ser Val Glu Glu Leu Asp Asp Ser Val Ser Ile Lys Ile Ala
385                 390                 395                 400

Lys Glu Ala Val Met Asn Ile Asn Lys Phe Gly Ser Leu Phe Lys Pro
            405                 410                 415

Thr Asp Gly Phe Leu Asp Thr Lys Ile Tyr Phe Ala Gly Leu Pro Arg
            420                 425                 430

Val Val Glu Ser Ala Leu Ile Lys Pro Ile Asn Pro Arg Leu Asp Gly
            435                 440                 445

Cys Ile Arg Gly Trp Asn Leu Met Lys Gln Gly Ala Leu Gly Ala Lys
450                 455                 460

Glu Ile Ile Gln Gly Lys Gln Asn Lys His Cys Phe Leu Met Val Glu
465                 470                 475                 480
```

```
Lys Gly Ser Tyr Tyr Pro Gly Ser Gly Ile Ala Arg Phe Ser Ile Asp
                485                 490                 495
Tyr Asn Asn Val Thr Asn Ala Glu Gly Trp Gln Ile Asn Val Thr Leu
            500                 505                 510
Asn Ile Arg Pro Ser Thr Gly Thr Gly Ile Met Leu Ala Leu Val Ser
        515                 520                 525
Gly Asp Lys Val Pro Phe Ala Leu Ser Leu Val Gly Ser Ser Ser Glu
    530                 535                 540
Asn Ser Gln Asp Ile Val Val Phe Val Glu Asn Ser Val Val Ala Arg
545                 550                 555                 560
Met Glu Ala Ile Thr Leu Cys Ser Asp Gln Gln Ser Gln Leu Lys Cys
                565                 570                 575
Asn Val Asn Arg His Gly Leu Glu Leu Trp Ser Pro Leu Lys Lys Asp
            580                 585                 590
Val Ile Tyr Ser Lys Asp Ile Gln Gly Gln Leu Ala Val Leu Asp Lys
        595                 600                 605
Ala Met Lys Gly Asn Val Ala Thr Tyr Leu Gly Gly Ile Pro Asp Leu
    610                 615                 620
Ser Phe Ser Ala Thr Pro Val Asn Ala Phe Tyr Ser Gly Cys Met Glu
625                 630                 635                 640
Val Asn Ile Asn Gly Val Gln Leu Asp Leu Asp Glu Ala Ile Ser Lys
                645                 650                 655
His Asn Asp Ile Arg Ala His Ser Cys Pro Ser Val Lys Lys Ile Gln
            660                 665                 670
Lys Asn Val
        675

<210> SEQ ID NO 6
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (3)..(19)
<223> OTHER INFORMATION: n is a, c, g, or t

<400> SEQUENCE: 6
agnnnnnnnn nnnnnnnnnc t                                          21

<210> SEQ ID NO 7
<211> LENGTH: 21
<212> TYPE: DNA
<213> ORGANISM: Artificial
<220> FEATURE:
<223> OTHER INFORMATION: Synthetic

<400> SEQUENCE: 7
agtgtgaatg tcctgacggc t                                          21

<210> SEQ ID NO 8
<211> LENGTH: 37
<212> TYPE: DNA
<213> ORGANISM: Artificial
<220> FEATURE:
<223> OTHER INFORMATION: Synthetic

<400> SEQUENCE: 8
gatctaaaaa agtgtgaatg tcctgacggc tttttta                         37
```

```
<210> SEQ ID NO 9
<211> LENGTH: 37
<212> TYPE: DNA
<213> ORGANISM: Artificial
<220> FEATURE:
<223> OTHER INFORMATION: Synthetic

<400> SEQUENCE: 9
gatctaaaaa agccgtcagg acattcacac tttttta                              37

<210> SEQ ID NO 10
<211> LENGTH: 21
<212> TYPE: DNA
<213> ORGANISM: Artificial
<220> FEATURE:
<223> OTHER INFORMATION: Synthetic

<400> SEQUENCE: 10
agctgcaaag atggccaagc t                                               21

<210> SEQ ID NO 11
<211> LENGTH: 37
<212> TYPE: DNA
<213> ORGANISM: Artificial
<220> FEATURE:
<223> OTHER INFORMATION: Synthetic

<400> SEQUENCE: 11
gatctaaaaa agctgcaaag atggccaagc tttttta                              37

<210> SEQ ID NO 12
<211> LENGTH: 37
<212> TYPE: DNA
<213> ORGANISM: Artificial
<220> FEATURE:
<223> OTHER INFORMATION: Synthetic

<400> SEQUENCE: 12
gatctaaaaa agcttggcca tctttgcagc tttttta                              37

<210> SEQ ID NO 13
<211> LENGTH: 21
<212> TYPE: DNA
<213> ORGANISM: Artificial
<220> FEATURE:
<223> OTHER INFORMATION: Synthetic

<400> SEQUENCE: 13
agaacatgcc tcgcaagtcc t                                               21

<210> SEQ ID NO 14
<211> LENGTH: 37
<212> TYPE: DNA
<213> ORGANISM: Artificial
<220> FEATURE:
<223> OTHER INFORMATION: Synthetic

<400> SEQUENCE: 14
gatctaaaaa agaacatgcc tcgcaagtcc tttttta                              37

<210> SEQ ID NO 15
<211> LENGTH: 37
<212> TYPE: DNA
<213> ORGANISM: Artificial
<220> FEATURE:
<223> OTHER INFORMATION: Synthetic
```

-continued

```
<400> SEQUENCE: 15
gatctaaaaa aggacttgcg aggcatgttc tttttta                              37

<210> SEQ ID NO 16
<211> LENGTH: 21
<212> TYPE: DNA
<213> ORGANISM: Artificial
<220> FEATURE:
<223> OTHER INFORMATION: Synthetic

<400> SEQUENCE: 16
agaaactaaa aagggcaatc t                                               21

<210> SEQ ID NO 17
<211> LENGTH: 37
<212> TYPE: DNA
<213> ORGANISM: Artificial
<220> FEATURE:
<223> OTHER INFORMATION: Synthetic

<400> SEQUENCE: 17
gatctaaaaa agaaactaaa aagggcaatc tttttta                              37

<210> SEQ ID NO 18
<211> LENGTH: 37
<212> TYPE: DNA
<213> ORGANISM: Artificial
<220> FEATURE:
<223> OTHER INFORMATION: Synthetic

<400> SEQUENCE: 18
gatctaaaaa agattgccct ttttagtttc tttttta                              37

<210> SEQ ID NO 19
<211> LENGTH: 21
<212> TYPE: DNA
<213> ORGANISM: Artificial
<220> FEATURE:
<223> OTHER INFORMATION: Synthetic

<400> SEQUENCE: 19
agccagattt gtgacaacac t                                               21

<210> SEQ ID NO 20
<211> LENGTH: 37
<212> TYPE: DNA
<213> ORGANISM: Artificial
<220> FEATURE:
<223> OTHER INFORMATION: Synthetic

<400> SEQUENCE: 20
gatctaaaaa agccagattt gtgacaacac tttttta                              37

<210> SEQ ID NO 21
<211> LENGTH: 37
<212> TYPE: DNA
<213> ORGANISM: Artificial
<220> FEATURE:
<223> OTHER INFORMATION: Synthetic

<400> SEQUENCE: 21
gatctaaaaa agtgttgtca caaatctggc tttttta                              37
```

```
<210> SEQ ID NO 22
<211> LENGTH: 25
<212> TYPE: PRT
<213> ORGANISM: Artificial
<220> FEATURE:
<223> OTHER INFORMATION: Synthetic

<400> SEQUENCE: 22

Met Arg Val Leu Ser Val Arg Cys Arg Leu Leu Leu Val Cys Leu Ala
1               5                   10                  15

Leu Val Leu Pro Ala Ser Glu Thr Asn
            20                  25

<210> SEQ ID NO 23
<211> LENGTH: 24
<212> TYPE: DNA
<213> ORGANISM: Artificial
<220> FEATURE:
<223> OTHER INFORMATION: Synthetic

<400> SEQUENCE: 23
ctgctggtat gcctagccct ggtg                                              24

<210> SEQ ID NO 24
<211> LENGTH: 24
<212> TYPE: DNA
<213> ORGANISM: Artificial
<220> FEATURE:
<223> OTHER INFORMATION: Synthetic

<400> SEQUENCE: 24
tgcagagctc ttcgatgcat tctc                                              24

<210> SEQ ID NO 25
<211> LENGTH: 24
<212> TYPE: DNA
<213> ORGANISM: Artificial
<220> FEATURE:
<223> OTHER INFORMATION: Synthetic

<400> SEQUENCE: 25
aagggcaatc ttgaaagaga atgc                                              24

<210> SEQ ID NO 26
<211> LENGTH: 25
<212> TYPE: DNA
<213> ORGANISM: Artificial
<220> FEATURE:
<223> OTHER INFORMATION: Synthetic

<400> SEQUENCE: 26
ccaaatattt tggataaaaa taatc                                             25

<210> SEQ ID NO 27
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n in position 3 is Adenosine or Guanosine

<400> SEQUENCE: 27
aancaacccc ttttgaccat                                                   20
```

<210> SEQ ID NO 28
<211> LENGTH: 21
<212> TYPE: DNA
<213> ORGANISM: Artificial
<220> FEATURE:
<223> OTHER INFORMATION: Synthetic

<400> SEQUENCE: 28
cccagaggag ctgcgagcct g                                              21

<210> SEQ ID NO 29
<211> LENGTH: 1631
<212> TYPE: DNA
<213> ORGANISM: Artificial
<220> FEATURE:
<223> OTHER INFORMATION: Synthetic

<400> SEQUENCE: 29
aarcaacccc ttttgaccat acacatttct actctttgtg tttgctggag ctgttttctc     60
cccacactca acccccttttg ctgaagcctg gaacttgctt tccacagctt aagttgttat   120
aggtttcaat catctgtcca cctccctgac tttcataatt ttgtgaaata cccttgcata   180
tatatatggg actaaatatt attttctcct ggttgtccat aatagattaa tttaattcct   240
aaacaaagaa cagaacatag attggtatag tagaagagtt tcccttctcc ctactgcatg   300
aatggaaatt ccccaaacca tccttatcag agaaattaac tcacatacta gtcacctttc   360
attcagctgg atgacaaaat catttttaaaa aaagagaata agaaaacag ataagaacaa    420 ctagatctag gaataatact taaaatatga ttctgcttag taggttttcat tcacacacct   480 agaaaaaaaa atcagtcaat gttttccttttg ggcagaaaat gagcaataat gggtatgcat  540
tgaccactac tgttggacat agccttattg cttcatatag catctattca aagtctcaga   600
tcaacactat gaaaacctgt catctctgta ttagatgatg tgactggggc tgtaaagggt   660
aagctctttt cttacagcta caacaacg ctaagaccaa gttctgtgct ttgagcccag      720
gcagtttagt ttcccaggag caacctaaag cctgattcac aggcatatgt atgatccaaa   780
ctgaatggta gtacatcaat accaaaacaa tctattggtg gaaacacacc ataggtgatc   840
gaaatactcc attttctttt cctctcatga cttctgttct gagcagtcct cttcctaaag   900
tctacattgt cttctgagtt caggctgaca tcttgacatc ctcctggctg gcacagtctc   960
tggacaagga gggaagaagg agagaaggg aaagggagag gagggggga gggagagaaa    1020 gaatgggaag aggaaggata tgaaagagag aagagaggag ggaaggcggg aggaagggag  1080
ggagggaggg agggagagag ggagagagag gagagagaga gagagagaga gagagagaga  1140
gagagagaga gagagagaga gagagaggga gagggagaga gagacagaga gagagagagg  1200
gagagggaga gagagagaga gagagagaga gagagagaga gagagagaga gtgaggagag  1260
agagagagag tttctcttcac cattggacat tcctaaagaa aagaagtaaa tgcaggattg  1320
gggacagtga cagaggacct ctgataaact ttctgaggcc tctgacctca ctctctcgga   1380
gccctcctcc accaccccacc cccccctcc ctagctgaga aaagcttcca ggaaatgtcc   1440
cagtcatcgc ttccctccc gggctggggg ctgggagcgg gcggtcccct caggccaggg   1500
ctgctccggc cgcgctcggg cagggccaca acagagctgg gaaagctgag cccaggctcg   1560
cagctcctct gggcggagcg ccggctcggt ccccgctgcg ccagccgtga tccccggcag  1620
cctgctcagc a                                                      1631

<210> SEQ ID NO 30
<211> LENGTH: 75
<212> TYPE: DNA
<213> ORGANISM: Artificial
<220> FEATURE:
<223> OTHER INFORMATION: Synthetic

<400> SEQUENCE: 30

```
atgagggtcc tgagcgtacg ctgtcggcta ctgctggtat gcctagccct ggtgctgcca      60
gcctcggaga caaac                                                       75
```

<210> SEQ ID NO 31
<211> LENGTH: 4209
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2647)..(2652)
<223> OTHER INFORMATION: n is a, c, g, or t

<400> SEQUENCE: 31

```
tgtaagtaat ccatacctcc tggcttctcc attccctatg tgccccggct tgaagatttt      60
ccactaggct gtttgctgcc tcctaagttt ccagtaagtc cgccaccatt cagagagtcg     120
cggcagcctg ggtctggtgg gcagtgtaaa ggtgggacag gatcaaagct tgccttgctt     180
tgagaaccat tgtccacagg acttgattcc agaacccggg tgacactaag tgtcaaagga     240
attgcttgaa catagtccta aatattgcta ggaaagctaa gtcaagcctg ttgccctcct     300
cccgtttaca agagtgcccc agcccgcacc ctctcctgcg gctaaccttc cttttgcaat     360
ttctggactt tgaacttgat tgactggtct cacattgaca aactgtttgg ggactgctgg     420
ggtgttacat atgattctct aaccttgata taagaaatag ctgttggatg ttaccttgta     480
ccgaggatca ttttctgagg gttttgactg ttgccgcttt gagatggcag caagaattct     540
gtacaacaca cacatttttg tgtttcttgg tctttcctct tcccattctc agattccggg     600
cagtatatcg agttttctct tagaaatata aaacgaacca caaggtttta gtacatttta     660
atggtcaatt aaattgtttt tagaagctta aatatgttca taattaacac tgctttcttt     720
tgctcttttg tagtcccagt cactggcatg ggagcaataa ctgtataaca aataccactt     780
aggtcactgc gagcaccaaa gaaacttttc aaagatggta attaagtagg agtttgctgg     840
aattgcaagt ttttattaat tagtaaggaa tctagcctga tattttaaa tgtctaacta      900 agttaaagac cagaatgaaa ctggttcact ttttattgag gataaacaag ttacagttat     960
aaagcctcaa caatcaaagc cctacgatga agcagcgtgt gactgtatgc acatgatcta    1020
tcttgttcag aggaacaatc aaacattttc agatagcatc agggcggtgg tggtactcgc    1080
ctataatcct agcaaagtca gaggcaagca gatctctgtg ttcaaggcca gcctagtcta    1140
cagagtgagt tccaggacaa ctggggctac acagagaaac ctgtctcaga gaaaacaaa     1200 ataaaaccaa attcagatag ctggtgtttg ggaaagagc aaaagacagc agtgctggcc    1260
acacagagag tagacaagtt cattctacaa ggacatcaca gaaagaatat gtgacccaat    1320
gacgaccata aactttcttg ttcctgtgtc aaattatctc cggtttattg atgaagaacc    1380
agacactatg agctgcgtct cctccttaag attttgtttt ggtgtcttgt ttttgtcaag    1440
gggtttcatt gtggccctga gcattagatc cagggctttg tgcatgctag ccagggagc    1500 tatattcccg aactccagaa gactaggaat ttgagatata aatagaattt gaattacctt    1560
```

```
ctgtacaatt gattgtatgg ttctagaaat attgctatat taagggaagc ctttgcagaa   1620
gacagttatt ttgagatggt gcataacaca aaagaaatga actaaagcct gaggcctgct   1680
ctgtagctct gccttgccct tagcctacaa taactttctt tacctttcaa gcatgtgcca   1740
ccacgcctga ctttcaggcc cttcatttta acaagaaagc aagtattcag ttatcaactg   1800
actttccaaa tgcatttgta tgaataaaaa ctacaaaaat ataaaaataa gaactataca   1860
cacaaaagcc ttgtatttaa aatttacgct gtggacatat tttgctcatc attcgtgaga   1920
gcttgcggta aaaaggcaaa ggggaagagg aggatatcta ttttgggtag gctaatttgg   1980
ccttatccag acttcccttt tgggtggatg cagtctgccc agcacactat ggcccatttt   2040
cttctacatg gctttgtgct ctgctctgcc cttagctaat tgtccccttt gacatgcttt   2100
tgtctttcct taaagtttct atacttcaaa aaccatcccg ctacactaat ggagtgattt   2160
tctcaagggt tgctttatgt ttggggtttg tactgcaaga gttagtttct gatatagcaa   2220
tggtgatagt atagtcttct accatgaact ctatgccagc aagtacaggg gtatatttca   2280
catgggtgtt ttctgttcac tgagtttcat gtcttctttg tatcttttg ttttgttttg   2340 tgagacaggg tttctctgta gcttttgagt cagtcctgga acttgctggc cggccttgaa   2400
ctcacagaga ttcacctgcc tctgcctccc aagtgctggg atttaaggtg tgagtcacca   2460
ctgccaggtt ttttctttgt atcttgagtg aactaaatag gtaagcttta aataataata   2520
tgagcagtct atttatatac attaaatatt aaatgcattg tgagatgagc atagcctttg   2580
aggcccagga acagaaagat ttacttcaca ttgtaaatat actggtatac atacaaacgt   2640
acatacnnnn nngtgtgtgt gtgtgtgtgt gtgtgtgtgt gcatgccata gcacacatgt   2700
gaagtccaga gtacagcatt ctcttttct accttttctgt agattcttgt ggtcagagtc   2760
aggtcaaatc aaatcagaca gatgcatgta taaaatgctc ttacccactg aaccatcttg   2820
ctgcttggtc cacaagctta gtggaagaat gctgggaagt gaatagtatg ttttaaatg   2880 tagttaacct tgactttttg ttgttgttgc tgttattgag gccacatttt cattgttctg   2940
agaaaatatt actattttcc tcagacagaa ttatatattt atttgaagtt catgaattcc   3000
atattatttt cctgtattta ttacaaatag catgcttaaa cacttccaag tagtgaaaca   3060
gctgctcatg taggacacgg attattgaca gtgctgccat ttatcagcca gtaatccact   3120
tggcaggtag cacgctcatc gttatccttt atgcacacaa agccttgttt gaattttatc   3180
ttttaatgag tgtcaatgaa atggaaagag ataagagtta aaaatacaac ccaaactatt   3240
gtatttacat ttctctttta gaagaaacct aaagcagcat tacttcttgc ccatatttaa   3300
taaataacat catttaccct tgttccctgc ctccagactc tcccatatac tcctctttca   3360
attttattgg cccctttaaa tgacatatca ttacatgtat atccctacac ataagtataa   3420
ccagttcagt ttgtataatg ttacttgcat gtgtgttttc aatgctgatc atttggtagt   3480
ggataaccaa tggtgtgccc tatgaagggg cagagtattt gtatcatgct tagcattcct   3540
ttgttgactg taggattttg tttaaggttg aggtctcttg gtctttcccc tgtctgcttc   3600
tgcatgtcca tggccatcct tgttcagctc atgtttatgt agtcatgctg atgaggcttt   3660
atggatgtag cttctgacat tgctaagcaa cacagtctca gcaaactccc cagtcctctg   3720
gttcttacaa tctttccaca ctgtttcacc atgttgtctg agccttaggt gctgaagttg   3780
ttttgtgtct gtatccattg ggactaggct ccacatgtct gcattttgat tacttgtggt   3840
tttctgtaac ggtctctatg tgttgcaacg agaaggagta gttgctttga cgatgtgtaa   3900
agactatctt gtgggtataa ggacaaatat ttgcatgaag ctatggatta tgctggtctc   3960
```

```
aagcatgaac tggataaatt gtacagctca cacaaaacag ctatagctag ctgcacagtc    4020
aggcatgcac tgatctgctt ggggagttgt taaccaaagg gcttacatag ctatgtattt    4080
tctaagctct agttttacta tcacaaagaa aattaattca cccttaattg tttaataaga    4140
tgatatatct tagggaaaaa atgaaggtct ttttttgact tatataaaag cttatgtttt    4200
ctacagttt                                                            4209

<210> SEQ ID NO 32
<211> LENGTH: 155
<212> TYPE: DNA
<213> ORGANISM: Artificial
<220> FEATURE:
<223> OTHER INFORMATION: Synthetic

<400> SEQUENCE: 32
tgtcaaaaga acatgcctcg caagtcctgg tgaggaagcg ccgcgcaaat accttgcttg      60
aagaaactaa aaagggcaat cttgaaagag aatgcatcga agagctctgc aataagagg     120 aagccaggga ggtctttgaa aacaatcccg aaacg                               155

<210> SEQ ID NO 33
<211> LENGTH: 3239
<212> TYPE: DNA
<213> ORGANISM: Artificial
<220> FEATURE:
<223> OTHER INFORMATION: Synthetic

<400> SEQUENCE: 33
gtaagagttc gtggaaatga ccaagtccac actcggatat atattggcag tcagaacact      60
gccagcttga gctaccttgc ttctgtttga aagctaatga cttaggagtt catttctcat     120
gtgttaccac tgacatttca ggcaggctgc caatgacagg cactccagcc aaactccatt     180
tcccttaagt ctcattactc gcaactagta tcgactttat aatgtgtgac tattttatta     240
tcctaaccaa atctggtagc cttgagggtg caagagaaga tgcgactgaa gggtaagtga     300
ccatatatgt acttgcattg tcactgtgct tttgttttgg ttgattgtgt ttgagacagt     360
ctcttactct gtagctccaa ctacaaggag ctccctatcc atctgctttg gcttcagcct     420
cccaagtact gtgattatag actggtgtgt cttgccattt atctttaaga ggctctagat     480
agaaatgggg ccacctaact gagattagtc attacagcat tatgtatgct gactgtatac     540
tattctgtaa ccttcatgaa gtttcccgag gccactgata atcagcagta atcattagtg     600
tctaaaaatt tccaagttac ccacccgcca aacataacat aaagacagca acatgggact     660
ctttgtccat tctgtgtttc aggagagggc aatttatagt atgcttgtaa ctaacaggag     720
tagcattaat atctccaagg agcactttga gcatgacctt gagagtctac atggaacact     780
gttcagggtc tcctcagatg ttctacctga gctgaattat acaatctgga ggaaaagaaa     840
gagatgacat acacaaggct cctcctttgc ctctgccaca gctcccagaa ccatgacaac     900
agctgagtga taaagagcaa ggactctttg tccatactta gaaaatttgt ccccaactgt     960
agctacttgt ggtctgtggt tgttattgta gctcttttt aatccctatg tgttctgata    1020
ggttcaaaga agaaattttc cccaaatatg caacaattaa attttaatct acctagaatt    1080
gagacaaaaa tgtgacgaaa taccttgatc aaaaaaacaa ctcaggagga aagggttttt    1140
tttttttttt ttggtttact aacctgaatt gagggaagca aaagtaggag ctcaaaccag    1200
gtgggaacct ggaggcagga gctgatgcag aggcatggag gagtgctgct tactggtctg    1260
ctcctcatgg cttgctcagc ttgttttctt atagaaccca gggccaccgt cacaaaagta    1320
```

```
ccatcacctg caatgggttg ggcccttccc cagggatctc tgattaagaa aattccctac    1380
aggtctgtct acaattcttt tttgtttgtt tgtttgtttg tttgtttgtt tgttttcgag    1440
acagggtttg tctgtatagc tttggagcct gtcctggaac tcactctgta gaccaggttg    1500
gcctcgaagt cacaaagatc cacctgcctt tgcctcccta gtgctgggat taaaggcttg    1560
tgtcaccact gccaggccta ttttaaggaa gcattttctc ccttgagatt ccttcctctc    1620
aaatgattct agcttgtatc aagttgacat aaaattagcc agcacagaca acaacaatag    1680
aaaattttct atcctacaca atgtaataaa tttattgggt aggatttaac atatgtattc    1740
tatgttttac attctcattc taaaaaggaa tgtgtatgca ctcttacaaa cttccataat    1800
acaaaagaat acagtatgta ttagatatgt gcatatattc cttcccttta tggaaagttt    1860
aaaaagtaga aagaatggta taataaactg caacacaaca cgtccctcta ataagatcaa    1920
ggctttcatt tgattttgcc tatccaccac atctaatcaa tggttttgct ttgagcaatc    1980
aagtcacatg attatattac ccatacttga gttgtatatc tgcattgtag atatgttctc    2040
aaagctcagc ctttaaagag tagtagggag ggaagatgga ccacaggaag aaggggagg     2100
aaggtgaaga aggaaaacac attcgtgttt ctttaccttc actaatagtt ttgttgacag    2160
attccaccta ctccctgtcc atatccctca tactcttagg ccagtattcc cagtgttatt    2220
gaccctgatg tttacctgtt cgcttgtcat cagcatgtca ccaatcttta aatgccattg    2280
tttgtctcct tattgtcttg tctctgcttc tgcagtaaac aacactgttg tctgaatgag    2340
tcagtgtcag gccccttct tataagccag tagaaacgtg caagtttgta catgataaga     2400
ggaaagagtg tagattttga tgtagaaaaa gccaagctcc actctaagcc agaatttga     2460
atacttttta tgcagaaatt ttgttttgt atgaaatatt cttgtgttat ttatttacat     2520
tatgagtgta ctgtcagaag ctcataaaaa ttaccctgtt cataaaatac attccttcat    2580
ccatatgtca tcattatttt gctatccatc aatatataag gaaggtgttt cacatgcatt    2640
agatgcaata aggtaagtgg tcattttagt tctctttaaa tgatttcatt gttgactcca    2700
gtgtagatag tcatcatggc ataagatgta tcaaatgaag actaggtgtg gtggtgcata    2760
ccttcagtcc cagcacacag aggcagagga acatggattg ctgtgagttt caggtggacc    2820
tggtctacat agtgagttcc aaggtagata gagggtgtct cgagagaccc tgtaagaaaa    2880
gtctatgttt aattgccatg aaaaaattag aggattataa aagagggaat atattgttat    2940
agttatcaac tacaaccagt tcaaatcaga agctttaaaa tgttatttta ttgttcagta    3000
gtgttttaag catatatatg tatacacaca aacatatatg tgtttatata tatgtatatg    3060
tatactggtc aagtattggc tatctattct tgaagtattt atagaaaaat tagaaatgtg    3120
aaaacataca acatgtaggt catttccata ttcatataaa agcaaattag aaaaattaat    3180
ctttaactct gtagtgatat ttgagtttgc taatatctat ttttttattt tctttctag    3239
```

<210> SEQ ID NO 34
<211> LENGTH: 25
<212> TYPE: DNA
<213> ORGANISM: Artificial
<220> FEATURE:
<223> OTHER INFORMATION: Synthetic

<400> SEQUENCE: 34

```
gattattttt atccaaaata tttgg                                            25
```

```
<210> SEQ ID NO 35
<211> LENGTH: 15
<212> TYPE: DNA
<213> ORGANISM: Artificial
<220> FEATURE:
<223> OTHER INFORMATION: Synthetic

<400> SEQUENCE: 35
ggagaggagg ggggg                                                     15

<210> SEQ ID NO 36
<211> LENGTH: 21
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid

<400> SEQUENCE: 36

Cys Xaa Xaa Cys Xaa Xaa Xaa Xaa Xaa Gln Ser Gly His Leu Gln Arg
1               5                  10                  15

His Xaa Xaa Xaa His
            20

<210> SEQ ID NO 37
<211> LENGTH: 23
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid

<400> SEQUENCE: 37

Cys Xaa Xaa Xaa Xaa Cys Xaa Xaa Xaa Xaa Xaa Arg Ser Asp Asn Leu
1               5                  10                  15

Ala Arg His Xaa Xaa Xaa His
            20

<210> SEQ ID NO 38
<211> LENGTH: 21
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
```

```
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid

<400> SEQUENCE: 38

Cys Xaa Xaa Cys Xaa Xaa Xaa Xaa Xaa Arg Ser Asp Asn Leu Thr Arg
1               5                   10                  15

His Xaa Xaa Xaa His
            20

<210> SEQ ID NO 39
<211> LENGTH: 23
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid

<400> SEQUENCE: 39

Cys Xaa Xaa Xaa Xaa Cys Xaa Xaa Xaa Xaa Arg Ser Asp His Leu
1               5                   10                  15

Thr Arg His Xaa Xaa Xaa His
            20

<210> SEQ ID NO 40
<211> LENGTH: 23
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid

<400> SEQUENCE: 40

Cys Xaa Xaa Xaa Xaa Cys Xaa Xaa Xaa Xaa Arg Ser Asp His Leu
1               5                   10                  15

Ala Arg His Xaa Xaa Xaa His
            20

<210> SEQ ID NO 41
<211> LENGTH: 15
<212> TYPE: PRT
<213> ORGANISM: Artificial
```

<220> FEATURE:
<223> OTHER INFORMATION: Synthetic

<400> SEQUENCE: 41

Gly Gly Ala Gly Ala Gly Gly Ala Gly Gly Gly Gly Gly Gly Gly
1               5                   10                  15

<210> SEQ ID NO 42
<211> LENGTH: 321
<212> TYPE: PRT
<213> ORGANISM: Artificial
<220> FEATURE:
<223> OTHER INFORMATION: Synthetic

<400> SEQUENCE: 42

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
                20                  25                  30

Thr Ala Gln Gln Ile Val Tyr Arg Asn Val Met Leu Glu Asn Tyr Lys
            35                  40                  45

Asn Leu Val Ser Leu Gly Tyr Gln Leu Thr Lys Pro Asp Val Ile Leu
        50                  55                  60

Arg Leu Glu Lys Gly Glu Glu Pro Trp Leu Val Glu Arg Glu Ile His
65                  70                  75                  80

Gln Glu Thr His Pro Asp Ser Glu Thr Ala Phe Glu Ile Lys Ser Ser
                85                  90                  95

Val Ser Ser Arg Ser Ile Phe Lys Asp Lys Gln Ser Cys Asp Ile Lys
                100                 105                 110

Met Glu Gly Met Ala Arg Asn Asp Leu Trp Tyr Leu Ser Leu Glu Glu
            115                 120                 125

Val Trp Lys Pro Gly Lys Lys Lys Gln His Ile Cys His Ile Gln Gly
        130                 135                 140

Cys Gly Lys Val Tyr Gly Arg Ser Asp His Leu Ala Arg His Leu Arg
145                 150                 155                 160

Trp His Thr Gly Glu Arg Pro Phe Met Cys Thr Trp Ser Tyr Cys Gly
                165                 170                 175

Lys Arg Phe Thr Arg Ser Asp His Leu Thr Arg His Lys Arg Thr His
                180                 185                 190

Thr Gly Glu Lys Lys Phe Ala Cys Pro Glu Cys Pro Lys Arg Phe Met
            195                 200                 205

Arg Ser Asp Asn Leu Thr Arg His Ile Lys Thr His Thr Gly Glu Arg
        210                 215                 220

Pro Phe Ala Cys Asp Trp Gln Gly Cys Asp Lys Lys Phe Ala Arg Ser
225                 230                 235                 240

Asp Asn Leu Ala Arg His His Arg Thr His Thr Gly Glu Lys Arg Phe
                245                 250                 255

Ser Cys Pro Leu Cys Ser Lys Arg Phe Thr Gln Ser Gly His Leu Gln
                260                 265                 270

Arg His Ala Arg Arg His Pro Gly Phe His Pro Asp Leu Leu Arg Arg
            275                 280                 285

Pro Gly Ala Arg Ser Thr Ser Pro Ser Asp Ser Leu Pro Cys Ser Leu
        290                 295                 300

Ala Gly Ser Pro Ala Pro Ser Pro Ala Pro Ser Pro Ala Pro Ala Gly
305                 310                 315                 320

Leu

<210> SEQ ID NO 43
<211> LENGTH: 4364
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2692)..(2697)
<223> OTHER INFORMATION: n is a, c, g, or t

<400> SEQUENCE: 43

| | | | | | |
|---|---|---|---|---|---|
| ctgctggtat | gcctagccct | ggtgctgcca | gcctcggaga | caaactgtaa | gtaatccata | 60 |
| cctcctggct | tctccattcc | ctatgtgccc | cggcttgaag | attttccact | aggctgtttg | 120 |
| ctgcctccta | agtttccagt | aagtccgcca | ccattcagag | agtcgcggca | gcctgggtct | 180 |
| ggtgggcagt | gtaaaggtgg | gacaggatca | agcttgcct | tgctttgaga | accattgtcc | 240 |
| acaggacttg | attccagaac | ccgggtgaca | ctaagtgtca | aaggaattgc | ttgaacatag | 300 |
| tcctaaatat | tgctaggaaa | gctaagtcaa | gcctgttgcc | ctcctcccgt | ttacaagagt | 360 |
| gccccagccc | gcaccctctc | ctgcggctaa | ccttcctttt | gcaatttctg | gactttgaac | 420 |
| ttgattgact | ggtctcacat | tgacaaactg | tttggggact | gctggggtgt | tacatatgat | 480 |
| tctctaacct | tgatataaga | aatagctgtt | ggatgttacc | ttgtaccgag | gatcattttc | 540 |
| tgagggtttt | gactgttgcc | gctttgagat | ggcagcaaga | attctgtaca | acacacacat | 600 |
| ttttgtgttt | cttggtcttt | cctcttccca | ttctcagatt | ccgggcagta | tatcgagttt | 660 |
| tctcttagaa | atataaaacg | aaccacaagg | ttttagtaca | ttttaatggt | caattaaatt | 720 |
| gttttagaa | gcttaaatat | gttcataatt | aacactgctt | tcttttgctc | ttttgtagtc | 780 |
| ccagtcactg | gcatgggagc | aataactgta | taacaaatac | cacttaggtc | actgcgagca | 840 |
| ccaaagaaac | ttttcaaaga | tggtaattaa | gtaggagttt | gctggaattg | caagttttta | 900 |
| ttaattagta | aggaatctag | cctgatattt | taaatgtct | aactaagtta | aagaccagaa | 960 |
| tgaaactggt | tcacttttta | ttgaggataa | acaagttaca | gttataaagc | ctcaacaatc | 1020 |
| aaagccctac | gatgaagcag | cgtgtgactg | tatgcacatg | atctatcttg | ttcagaggaa | 1080 |
| caatcaaaca | ttttcagata | gcatcagggc | ggtggtggta | ctcgcctata | atcctagcaa | 1140 |
| agtcagaggc | aagcagatct | ctgtgttcaa | ggccagccta | gtctacagag | tgagttccag | 1200 |
| gacaactggg | gctacacaga | gaaacctgtc | tcagagaaaa | acaaaataaa | accaaattca | 1260 |
| gatagctggt | gtttgggaaa | agagcaaaag | acagcagtgc | tggccacaca | gagagtagac | 1320 |
| aagttcattc | tacaaggaca | tcacagaaag | aatatgtgac | ccaatgacga | ccataaactt | 1380 |
| tcttgttcct | gtgtcaaatt | atctccggtt | tattgatgaa | gaaccagaca | ctatgagctg | 1440 |
| cgtctcctcc | ttaagatttt | gttttggtgt | cttgttttg | tcaagggggtt | tcattgtggc | 1500 |
| cctgagcatt | agatccaggg | ctttgtgcat | gctaggccag | ggagctatat | tcccgaactc | 1560 |
| cagaagacta | ggaatttgag | atataaatag | aatttgaatt | accttctgta | caattgattg | 1620 |
| tatggttcta | gaaatattgc | tatattaagg | gaagcctttg | cagaagacag | ttattttgag | 1680 |
| atggtgcata | acacaaaaga | aatgaactaa | agcctgaggc | ctgctctgta | gctctgcctt | 1740 |
| gcccttagcc | tacaataact | ttctttacct | ttcaagcatg | tgccaccacg | cctgactttc | 1800 |
| aggcccttca | ttttaacaag | aaagcaagta | ttcagttatc | aactgacttt | ccaaatgcat | 1860 |
| ttgtatgaat | aaaaactaca | aaaatataaa | aataagaact | atacacacaa | aagccttgta | 1920 |
| tttaaaattt | acgctgtgga | catattttgc | tcatcattcg | tgagagcttg | cggtaaaaag | 1980 |

```
gcaaagggga agaggaggat atctattttg ggtaggctaa tttggcctta tccagacttc    2040
ccttttgggt ggatgcagtc tgcccagcac actattggcc catttcttct acatggcttt    2100
gtgctctgct ctgcccttag ctaattgtcc cctttgacat gcttttgtct ttccttaaag    2160
tttctatact tcaaaaacca tcccgctaca ctaatggagt gattttctca agggttgctt    2220
tatgtttggg gtttgtactg caagagttag tttctgatat agcaatggtg atagtatagt    2280
cttctaccat gaactctatg ccagcaagta caggggtata tttcacatgg gtgttttctg    2340
ttcactgagt ttcatgtctt ctttgtatct ttttgttttg ttttgtgaga cagggtttct    2400
ctgtagcttt tgagtcagtc ctggaacttg ctggccggcc ttgaactcac agagattcac    2460
ctgcctctgc ctcccaagtg ctgggattta aggtgtgagt caccactgcc aggttttttc    2520
tttgtatctt gagtgaacta aataggtaag ctttaaataa taatatgagc agtctattta    2580
tatacattaa atattaaatg cattgtgaga tgagcatagc ctttgaggcc caggaacaga    2640
aagatttact tcacattgta aatatactgg tatacataca aacgtacata cnnnnnngtg    2700
tgtgtgtgtg tgtgtgtgtg tgtgtgcatg ccatagcaca catgtgaagt ccagagtaca    2760
gcattctctt tttctacctt tctgtagatt cttgtggtca gagtcaggtc aaatcaaatc    2820
agacagatgc atgtataaaa tgctcttacc cactgaacca tcttgctgct tggtccacaa    2880
gcttagtgga agaatgctgg gaagtgaata gtatgttttt aaatgtagtt aaccttgact    2940
ttttgttgtt gttgctgtta ttgaggccac attttcattg ttctgagaaa atattactat    3000
tttcctcaga cagaattata tatttatttg aagttcatga attccatatt attttcctgt    3060
atttattaca aatagcatgc ttaaacactt ccaagtagtg aaacagctgc tcatgtagga    3120
cacggattat tgacagtgct gccatttatc agccagtaat ccacttggca ggtagcacgc    3180
tcatcgttat cctttatgca cacaaagcct tgtttgaatt ttatctttta atgagtgtca    3240
atgaaatgga aagagataag agttaaaaat acaacccaaa ctattgtatt tacatttctc    3300
ttttagaaga aacctaaagc agcattactt cttgcccata tttaataaat aacatcattt    3360
acccttgttc cctgcctcca gactctccca tatactcctc tttcaatttt attggcccct    3420
ttaaatgaca tatcattaca tgtatatccc tacacataag tataaccagt tcagtttgta    3480
taatgttact tgcatgtgtg ttttcaatgc tgatcatttg gtagtggata accaatggtg    3540
tgccctatga aggggcagag tatttgtatc atgcttagca ttcctttgtt gactgtagga    3600
ttttgtttaa ggttgaggtc tcttggtctt tcccctgtct gcttctgcat gtccatggcc    3660
atccttgttc agctcatgtt tatgtagtca tgctgatgag gctttatgga tgtagcttct    3720
gacattgcta agcaacacag tctcagcaaa ctccccagtc ctctggttct tacaatcttt    3780
ccacactgtt tcaccatgtt gtctgagcct taggtgctga agttgttttg tgtctgtatc    3840
cattgggact aggctccaca tgtctgcatt ttgattactt gtggttttct gtaacggtct    3900
ctatgtgttg caacgagaag gagtagttgc tttgacgatg tgtaaagact atcttgtggg    3960
tataaggaca aatatttgca tgaagctatg gattatgctg gtctcaagca tgaactggat    4020
aaattgtaca gctcacacaa aacagctata gctagctgca cagtcaggca tgcactgatc    4080
tgcttgggga gttgttaacc aaagggctta catagctatg tattttctaa gctctagttt    4140
tactatcaca aagaaaatta attcacccct aattgtttaa taagatgata tatcttaggg    4200
aaaaaatgaa ggtctttttt tgacttatat aaaagcttat gttttctaca gttttgtcaa    4260
aagaacatgc ctcgcaagtc ctggtgagga agcgccgcgc aaataccttg cttgaagaaa    4320
ctaaaaaggg caatcttgaa agagaatgca tcgaagagct ctgc                    4364
```

<210> SEQ ID NO 44
<211> LENGTH: 948
<212> TYPE: DNA
<213> ORGANISM: Artificial
<220> FEATURE:
<223> OTHER INFORMATION: Synthetic

<400> SEQUENCE: 44

| | | | | | |
|---|---|---|---|---|---|
| atgaagctac | tgtcttctat | cgaacaagca | tgcccaaaaa | agaagagaaa | ggtagatgaa | 60 |
| aaaccttaca | agtgtccgga | atgtgggaag | tcctttagtc | ggagcgacaa | cctggcccgg | 120 |
| caccagcgga | cgcataccgg | tgagaagccc | tacaaatgcc | cagaatgcgg | aaaatcattt | 180 |
| tcgcggagca | gcaacctgcg | ggagcaccaa | cgaacccaca | caggcgagaa | accatttaaa | 240 |
| tgtcctgagt | gtggtaagag | ctttagccgg | agcgacaacc | tgacccggca | tcaagctact | 300 |
| catacgggcg | gcggtggcag | cggtggcggt | agcggcggtg | gcagcggtgg | cggatcccaa | 360 |
| ctagtcaaaa | gtgaactgga | ggagaagaaa | tctgaacttc | gtcataaatt | gaaatatgtg | 420 |
| cctcatgaat | atattgaatt | aattgaaatt | gccagaaatt | ccactcagga | tagaattctt | 480 |
| gaaatgaagg | taatggaatt | ttttatgaaa | gtttatggat | atagaggtaa | acatttgggt | 540 |
| ggatcaagga | aaccggacgg | agcaatttat | actgtcggat | ctcctattga | ttacggtgtg | 600 |
| atcgtggata | ctaaagctta | tagcggaggt | tataatctgc | caattggcca | agcagatgaa | 660 |
| atgcaacgat | atgtcgaaga | aaatcaaaca | cgaaacaaac | atatcaaccc | taatgaatgg | 720 |
| tggaaagtct | atccatcttc | tgtaacggaa | tttaagtttt | tatttgtgag | tggtcacttt | 780 |
| aaaggaaact | acaaagctca | gcttacacga | ttaaatcata | tcactaattg | taatggagct | 840 |
| gttcttagtg | tagaagagct | tttaattggt | ggagaaatga | ttaaagccgg | cacattaacc | 900 |
| ttagaggaag | tgagacggaa | atttaataac | ggcgagataa | acttttag | | 948 |

<210> SEQ ID NO 45
<211> LENGTH: 978
<212> TYPE: DNA
<213> ORGANISM: Artificial
<220> FEATURE:
<223> OTHER INFORMATION: Synthetic

<400> SEQUENCE: 45

| | | | | | |
|---|---|---|---|---|---|
| atgaagctac | tgtcttctat | cgaacaagca | tgcccaaaaa | agaagagaaa | ggtagatgaa | 60 |
| aaaccttaca | agtgtccgga | atgtgggaag | tcctttagtc | ggagcgacaa | cctggcccgg | 120 |
| caccagcgga | cgcataccgg | tgagaagccc | tacaaatgcc | cagaatgcgg | aaaatcattt | 180 |
| tcgcggagca | gcaacctgcg | ggagcaccaa | cgaacccaca | caggcgagaa | accatttaaa | 240 |
| tgtcctgagt | gtggtaagag | ctttagccgg | agcgacaacc | tgacccggca | tcaagctact | 300 |
| catacgggcg | gcggtggcag | cggtggcggt | agcggcggtg | gcagcggtgg | cggatccgta | 360 |
| ttagaaaaaa | gtgatattga | aaaatttaag | aatcaattgc | gtacggaact | aaccaatatt | 420 |
| gaccattctt | atcttaaagg | aattgatata | gctagtaaaa | agaaaaccag | taatgttgaa | 480 |
| aatacggaat | ttgaagcaat | atcaaccaag | attttttacgg | atgagttggg | ttttttcaggc | 540 |
| aaacatctag | gaggaagcaa | caaaccagat | ggactcctgt | gggatgatga | ttgtgcaatt | 600 |
| attcttgatt | caaaagctta | ctcagaaggc | tttccactca | ctgcctccca | cacagatgct | 660 |
| atgggaagat | atttgaggca | atttacagag | cgaaaagaag | aaataaagcc | aacgtggtgg | 720 |
| gatattgctc | cagaacattt | agacaataca | tatttcgctt | acgtttctgg | agttttttcg | 780 |
| ggtaattata | aggaacagtt | acaaaaattt | aggcaagata | caaaccattt | aggtggggca | 840 |

```
ctagagtttg ttaaattgtt attactagca ataattata aaactcaaaa aatgagtaaa    900
aaagaagtta agaaaagtat tcttgattat aatatttcat atgaagaata tgctccatta    960
cttgcagaaa tagagtaa                                                  978
```

<210> SEQ ID NO 46
<211> LENGTH: 948
<212> TYPE: DNA
<213> ORGANISM: Artificial
<220> FEATURE:
<223> OTHER INFORMATION: Synthetic

<400> SEQUENCE: 46

```
atgaagctac tgtcttctat cgaacaagca tgcccaaaaa agaagagaaa ggtagatgaa     60
aaaccttaca agtgtccgga atgtgggaag tcctttagtc ggagcgacgc cctgacccag    120
caccagcgga cgcataccgg tgagaagccc tacaaatgcc cagaatgcgg aaaatcattt    180
tcgcagagca gccacctggc ccggcaccaa cgaacccaca caggcgagaa accatttaaa    240
tgtcctgagt gtggtaagag ctttagccag agcagccacc tgacccggca tcaagctact    300
catacgggcg gcgtggcag cggtggcggt agcggcggtg gcagcggtgg cggatcccaa    360
ctagtcaaaa gtgaactgga ggagaagaaa tctgaacttc gtcataaatt gaaatatgtg    420
cctcatgaat atattgaatt aattgaaatt gccagaaatt ccactcagga tagaattctt    480
gaaatgaagg taatggaatt ttttatgaaa gtttatggat atagaggtaa acatttgggt    540
ggatcaagga aaccggacgg agcaatttat actgtcggat ctcctattga ttacggtgtg    600
atcgtggata ctaaagctta tagcggaggt tataatctgc caattggcca agcagatgaa    660
atgcaacgat atgtcgaaga aaatcaaaca cgaaacaaac atatcaaccc taatgaatgg    720
tggaaagtct atccatcttc tgtaacggaa tttaagtttt tatttgtgag tggtcacttt    780
aaaggaaact acaaagctca gcttacacga ttaaatcata tcactaattg taatggagct    840
gttcttagtg tagaagagct tttaattggt ggagaaatga ttaaagccgg cacattaacc    900
ttagaggaag tgagacggaa atttaataac ggcgagataa acttttag                 948
```

<210> SEQ ID NO 47
<211> LENGTH: 978
<212> TYPE: DNA
<213> ORGANISM: Artificial
<220> FEATURE:
<223> OTHER INFORMATION: Synthetic

<400> SEQUENCE: 47

```
atgaagctac tgtcttctat cgaacaagca tgcccaaaaa agaagagaaa ggtagatgaa     60
aaaccttaca agtgtccgga atgtgggaag tcctttagtc ggagcgacgc cctgacccag    120
caccagcgga cgcataccgg tgagaagccc tacaaatgcc cagaatgcgg aaaatcattt    180
tcgcagagca gccacctggc ccggcaccaa cgaacccaca caggcgagaa accatttaaa    240
tgtcctgagt gtggtaagag ctttagccag agcagccacc tgacccggca tcaagctact    300
catacgggcg gcgtggcag cggtggcggt agcggcggtg gcagcggtgg cggatccgta    360
ttagaaaaaa gtgatattga aaaatttaag aatcaattgc gtacggaact aaccaatatt    420
gaccattctt atcttaaagg aattgatata gctagtaaaa agaaaaccag taatgttgaa    480
aatacggaat ttgaagcaat atcaaccaag attttttacgg atgagttggg ttttcaggc    540 aaacatctag gaggaagcaa caaaccagat ggactcctgt gggatgatga ttgtgcaatt    600
attcttgatt caaaagctta ctcagaaggc tttccactca ctgcctccca cacagatgct    660
```

```
atgggaagat atttgaggca atttacagag cgaaaagaag aaataaagcc aacgtggtgg    720
gatattgctc cagaacattt agacaataca tatttcgctt acgttctgg gagttttcg     780 ggtaattata aggaacagtt acaaaaattt aggcaagata caaaccattt aggtggggca   840
ctagagtttg ttaaattgtt attactagca ataattata aaactcaaaa aatgagtaaa    900
aaagaagtta agaaaagtat tcttgattat aatatttcat atgaagaata tgctccatta   960
cttgcagaaa tagagtaa                                                 978
```

<210> SEQ ID NO 48
<211> LENGTH: 315
<212> TYPE: PRT
<213> ORGANISM: Artificial
<220> FEATURE:
<223> OTHER INFORMATION: Synthetic

<400> SEQUENCE: 48

```
Met Lys Leu Leu Ser Ser Ile Glu Gln Ala Cys Pro Lys Lys Lys Arg
1               5                   10                  15

Lys Val Asp Glu Lys Pro Tyr Lys Cys Pro Glu Cys Gly Lys Ser Phe
            20                  25                  30

Ser Arg Ser Asp Asn Leu Ala Arg His Gln Arg Thr His Thr Gly Glu
        35                  40                  45

Lys Pro Tyr Lys Cys Pro Glu Cys Gly Lys Ser Phe Ser Arg Ser Ser
    50                  55                  60

Asn Leu Arg Glu His Gln Arg Thr His Thr Gly Glu Lys Pro Phe Lys
65                  70                  75                  80

Cys Pro Glu Cys Gly Lys Ser Phe Ser Arg Ser Asp Asn Leu Thr Arg
                85                  90                  95

His Gln Ala Thr His Thr Gly Gly Gly Ser Gly Gly Gly Ser Gly
            100                 105                 110

Gly Gly Ser Gly Gly Gly Ser Gln Leu Val Lys Ser Glu Leu Glu Glu
        115                 120                 125

Lys Lys Ser Glu Leu Arg His Lys Leu Lys Tyr Val Pro His Glu Tyr
    130                 135                 140

Ile Glu Leu Ile Glu Ile Ala Arg Asn Ser Thr Gln Asp Arg Ile Leu
145                 150                 155                 160

Glu Met Lys Val Met Glu Phe Phe Met Lys Val Tyr Gly Tyr Arg Gly
                165                 170                 175

Lys His Leu Gly Gly Ser Arg Lys Pro Asp Gly Ala Ile Tyr Thr Val
            180                 185                 190

Gly Ser Pro Ile Asp Tyr Gly Val Ile Val Asp Thr Lys Ala Tyr Ser
        195                 200                 205

Gly Gly Tyr Asn Leu Pro Ile Gly Gln Ala Asp Glu Met Gln Arg Tyr
    210                 215                 220

Val Glu Glu Asn Gln Thr Arg Asn Lys His Ile Asn Pro Asn Glu Trp
225                 230                 235                 240

Trp Lys Val Tyr Pro Ser Ser Val Thr Glu Phe Lys Phe Leu Phe Val
                245                 250                 255

Ser Gly His Phe Lys Gly Asn Tyr Lys Ala Gln Leu Thr Arg Leu Asn
            260                 265                 270

His Ile Thr Asn Cys Asn Gly Ala Val Leu Ser Val Glu Glu Leu Leu
        275                 280                 285
```

Ile Gly Gly Glu Met Ile Lys Ala Gly Thr Leu Thr Leu Glu Glu Val
290                 295                 300

Arg Arg Lys Phe Asn Asn Gly Glu Ile Asn Phe
305                 310                 315

<210> SEQ ID NO 49
<211> LENGTH: 325
<212> TYPE: PRT
<213> ORGANISM: Artificial
<220> FEATURE:
<223> OTHER INFORMATION: Synthetic

<400> SEQUENCE: 49

Met Lys Leu Leu Ser Ser Ile Glu Gln Ala Cys Pro Lys Lys Lys Arg
1               5                   10                  15

Lys Val Asp Glu Lys Pro Tyr Lys Cys Pro Glu Cys Gly Lys Ser Phe
                20                  25                  30

Ser Arg Ser Asp Asn Leu Ala Arg His Gln Arg Thr His Thr Gly Glu
            35                  40                  45

Lys Pro Tyr Lys Cys Pro Glu Cys Gly Lys Ser Phe Ser Arg Ser Ser
        50                  55                  60

Asn Leu Arg Glu His Gln Arg Thr His Thr Gly Glu Lys Pro Phe Lys
65                  70                  75                  80

Cys Pro Glu Cys Gly Lys Ser Phe Ser Arg Ser Asp Asn Leu Thr Arg
                85                  90                  95

His Gln Ala Thr His Thr Gly Gly Gly Ser Gly Gly Gly Ser Gly
            100                 105                 110

Gly Gly Ser Gly Gly Gly Ser Val Leu Glu Lys Ser Asp Ile Glu Lys
        115                 120                 125

Phe Lys Asn Gln Leu Arg Thr Glu Leu Thr Asn Ile Asp His Ser Tyr
130                 135                 140

Leu Lys Gly Ile Asp Ile Ala Ser Lys Lys Thr Ser Asn Val Glu
145                 150                 155                 160

Asn Thr Glu Phe Glu Ala Ile Ser Thr Lys Ile Phe Thr Asp Glu Leu
                165                 170                 175

Gly Phe Ser Gly Lys His Leu Gly Gly Ser Asn Lys Pro Asp Gly Leu
            180                 185                 190

Leu Trp Asp Asp Cys Ala Ile Ile Leu Asp Ser Lys Ala Tyr Ser
        195                 200                 205

Glu Gly Phe Pro Leu Thr Ala Ser His Thr Asp Ala Met Gly Arg Tyr
210                 215                 220

Leu Arg Gln Phe Thr Glu Arg Lys Glu Glu Ile Lys Pro Thr Trp Trp
225                 230                 235                 240

Asp Ile Ala Pro Glu His Leu Asp Asn Thr Tyr Phe Ala Tyr Val Ser
                245                 250                 255

Gly Ser Phe Ser Gly Asn Tyr Lys Glu Gln Leu Gln Lys Phe Arg Gln
            260                 265                 270

Asp Thr Asn His Leu Gly Gly Ala Leu Glu Phe Val Lys Leu Leu Leu
        275                 280                 285

Leu Ala Asn Asn Tyr Lys Thr Gln Lys Met Ser Lys Lys Glu Val Lys
290                 295                 300

Lys Ser Ile Leu Asp Tyr Asn Ile Ser Tyr Glu Glu Tyr Ala Pro Leu
305                 310                 315                 320

Leu Ala Glu Ile Glu
            325

```
<210> SEQ ID NO 50
<211> LENGTH: 315
<212> TYPE: PRT
<213> ORGANISM: Artificial
<220> FEATURE:
<223> OTHER INFORMATION: Synthetic

<400> SEQUENCE: 50

Met Lys Leu Leu Ser Ser Ile Glu Gln Ala Cys Pro Lys Lys Arg
1               5                   10                  15

Lys Val Asp Glu Lys Pro Tyr Lys Cys Pro Glu Cys Gly Lys Ser Phe
            20                  25                  30

Ser Arg Ser Asp Ala Leu Thr Gln His Gln Arg Thr His Thr Gly Glu
        35                  40                  45

Lys Pro Tyr Lys Cys Pro Glu Cys Gly Lys Ser Phe Ser Gln Ser Ser
    50                  55                  60

His Leu Ala Arg His Gln Arg Thr His Thr Gly Glu Lys Pro Phe Lys
65                  70                  75                  80

Cys Pro Glu Cys Gly Lys Ser Phe Ser Gln Ser Ser His Leu Thr Arg
                85                  90                  95

His Gln Ala Thr His Thr Gly Gly Gly Ser Gly Gly Gly Ser Gly
            100                 105                 110

Gly Gly Ser Gly Gly Gly Ser Gln Leu Val Lys Ser Glu Leu Glu Glu
        115                 120                 125

Lys Lys Ser Glu Leu Arg His Lys Leu Lys Tyr Val Pro His Glu Tyr
    130                 135                 140

Ile Glu Leu Ile Glu Ile Ala Arg Asn Ser Thr Gln Asp Arg Ile Leu
145                 150                 155                 160

Glu Met Lys Val Met Glu Phe Phe Met Lys Val Tyr Gly Tyr Arg Gly
                165                 170                 175

Lys His Leu Gly Gly Ser Arg Lys Pro Asp Gly Ala Ile Tyr Thr Val
            180                 185                 190

Gly Ser Pro Ile Asp Tyr Gly Val Ile Val Asp Thr Lys Ala Tyr Ser
        195                 200                 205

Gly Gly Tyr Asn Leu Pro Ile Gly Gln Ala Asp Glu Met Gln Arg Tyr
    210                 215                 220

Val Glu Glu Asn Gln Thr Arg Asn Lys His Ile Asn Pro Asn Glu Trp
225                 230                 235                 240

Trp Lys Val Tyr Pro Ser Ser Val Thr Glu Phe Lys Phe Leu Phe Val
                245                 250                 255

Ser Gly His Phe Lys Gly Asn Tyr Lys Ala Gln Leu Thr Arg Leu Asn
            260                 265                 270

His Ile Thr Asn Cys Asn Gly Ala Val Leu Ser Val Glu Glu Leu Leu
        275                 280                 285

Ile Gly Gly Glu Met Ile Lys Ala Gly Thr Leu Thr Leu Glu Glu Val
    290                 295                 300

Arg Arg Lys Phe Asn Asn Gly Glu Ile Asn Phe
305                 310                 315

<210> SEQ ID NO 51
<211> LENGTH: 325
<212> TYPE: PRT
<213> ORGANISM: Artificial
<220> FEATURE:
<223> OTHER INFORMATION: Synthetic
```

<400> SEQUENCE: 51

```
Met Lys Leu Leu Ser Ser Ile Glu Gln Ala Cys Pro Lys Lys Lys Arg
1               5                   10                  15
Lys Val Asp Glu Lys Pro Tyr Lys Cys Pro Glu Cys Gly Lys Ser Phe
            20                  25                  30
Ser Arg Ser Asp Ala Leu Thr Gln His Gln Arg Thr His Thr Gly Glu
        35                  40                  45
Lys Pro Tyr Lys Cys Pro Glu Cys Gly Lys Ser Phe Ser Gln Ser Ser
    50                  55                  60
His Leu Ala Arg His Gln Arg Thr His Thr Gly Glu Lys Pro Phe Lys
65                  70                  75                  80
Cys Pro Glu Cys Gly Lys Ser Phe Ser Gln Ser Ser His Leu Thr Arg
                85                  90                  95
His Gln Ala Thr His Thr Gly Gly Gly Ser Gly Gly Gly Ser Gly
            100                 105                 110
Gly Gly Ser Gly Gly Gly Ser Val Leu Glu Lys Ser Asp Ile Glu Lys
            115                 120                 125
Phe Lys Asn Gln Leu Arg Thr Glu Leu Thr Asn Ile Asp His Ser Tyr
130                 135                 140
Leu Lys Gly Ile Asp Ile Ala Ser Lys Lys Lys Thr Ser Asn Val Glu
145                 150                 155                 160
Asn Thr Glu Phe Glu Ala Ile Ser Thr Lys Ile Phe Thr Asp Glu Leu
            165                 170                 175
Gly Phe Ser Gly Lys His Leu Gly Gly Ser Asn Lys Pro Asp Gly Leu
            180                 185                 190
Leu Trp Asp Asp Asp Cys Ala Ile Ile Leu Asp Ser Lys Ala Tyr Ser
            195                 200                 205
Glu Gly Phe Pro Leu Thr Ala Ser His Thr Asp Ala Met Gly Arg Tyr
210                 215                 220
Leu Arg Gln Phe Thr Glu Arg Lys Glu Glu Ile Lys Pro Thr Trp Trp
225                 230                 235                 240
Asp Ile Ala Pro Glu His Leu Asp Asn Thr Tyr Phe Ala Tyr Val Ser
            245                 250                 255
Gly Ser Phe Ser Gly Asn Tyr Lys Glu Gln Leu Gln Lys Phe Arg Gln
            260                 265                 270
Asp Thr Asn His Leu Gly Gly Ala Leu Glu Phe Val Lys Leu Leu Leu
            275                 280                 285
Leu Ala Asn Asn Tyr Lys Thr Gln Lys Met Ser Lys Lys Glu Val Lys
290                 295                 300
Lys Ser Ile Leu Asp Tyr Asn Ile Ser Tyr Glu Tyr Ala Pro Leu
305                 310                 315                 320
Leu Ala Glu Ile Glu
                325
```

<210> SEQ ID NO 52
<211> LENGTH: 9064
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (5360)..(5365)
<223> OTHER INFORMATION: n is a, c, g, or t -continued

```
<400> SEQUENCE: 52
ggtaccgagc tcttacgcgt gctagcccgg gctcgagatc tcaaccccctt ttgaccatac      60 acatttctac tctttgtgtt tgctggagct gttttctccc cacactcaac ccccttttgct    120 gaagcctgga acttgctttc cacagcttaa gttgttatag gtttcaatca tctgtccacc    180
tccctgactt tcataatttt gtgaaatacc cttgcatata tatatgggac taaatattat    240
tttctcctgg ttgtccataa tagattaatt taattcctaa acaaagaaca gaacatagat    300
tggtatagta gaagagtttc ccttctccct actgcatgaa tggaaattcc ccaaaccatc    360
cttatcagag aaattaactc acatactagt cacctttcat tcagctggat gacaaaatca    420 tttttaaaaaa agagaataaa gaaaacagat aagaacaact agatctagga ataatactta    480
aaatatgatt ctgcttagta ggtttcattc acacacctag aaaaaaaaat cagtcaatgt    540
ttcctttggg cagaaaatga gcaataatgg gtatgcattg accactactg ttggacatag    600
ccttattgct tcatatagca tctattcaaa gtctcagatc aacactatga aaacctgtca    660
tctctgtatt agatgatgtg actggggctg taaagggtaa gctcttttct tacagctata    720
caacaacgct aagaccaagt tctgtgcttt gagcccaggc agtttagttt cccaggagca    780
acctaaagcc tgattcacag gcatatgtat gatccaaact gaatggtagt acatcaatac    840
caaaacaatc tattggtgga aacacaccat aggtgatcga aatactccat tttcttttcc    900
tctcatgact tctgttctga gcagtcctct tcctaaagtc tacattgtct tctgagttca    960
ggctgacatc ttgacatcct cctggctggc acagtctctg gacaaggagg gaagaaggag   1020
agaaggggaa agggagagga gggggggagg gagagaaaga atgggaagag gaaggatatg   1080
aaagagagaa gagaggaggg aaggcgggag gaagggaggg agggagggag ggagagaggg   1140
agagagagga gagagagaga gagagagaga gagagagaga gagagagaga gagagagaga   1200
gagagggaga gggagagaga gacagagaga gagagaggga gagggagaga gagagagaga   1260
gagagagaga gagagagaga gagagagagt gaggagagag agagagagtt ttcttcacca   1320
ttggacattc ctaaagaaaa gaagtaaatg caggattggg gacagtgaca gaggacctct   1380
gataaacttt ctgaggcctc tgacctcact ctctcggagc cctcctccac cacccacccc   1440 cccctccct agctgagaaa agcttccagg aaatgtccca gtcatcgctt cccctcccgg   1500
gctgggggct gggagcgggc ggtcccctca ggccagggct gctccggccg cgctcgggca   1560
gggccacaac agagctggga aagctgagcc caggctcgca gctcctctgg gcggagcgcc   1620
ggctcggtcc ccgctgcgcc agccgtgatc cccggcagcc tgctcagcca tggtgagcaa   1680
gggcgaggag ctgttcaccg gggtggtgcc catcctggtc gagctggacg gcgacgtaaa   1740
cggccacaag ttcagcgtgt ccggcgaggg cgagggcgat gccacctacg gcaagctgac   1800
cctgaagttc atctgcacca ccggcaagct gcccgtgccc tggcccaccc tcgtgaccac   1860
cctgacctac ggcgtgcagt gcttcagccg ctacccgac cacatgaagc agcacgactt   1920
cttcaagtcc gccatgcccg aaggctacgt ccaggagcgc accatcttct tcaaggacga   1980
cggcaactac aagacccgcg ccgaggtgaa gttcgagggc gacacccttgg tgaaccgcat   2040 cgagctgaag ggcatcgact tcaaggagga cggcaacatc ctggggcaca agctggagta   2100
caactacaac agccacaacg tctatatcat ggccgacaag cagaagaacg gcatcaaggt   2160
gaacttcaag atccgccaca acatcgagga cggcagcgtg cagctcgccg accactacca   2220
gcagaacacc cccatcggcg acggccccgt gctgctgccc gacaaccact acctgagcac   2280
ccagtccgcc ctgagcaaag accccaacga gaagcgcgat cacatggtcc tgctggagtt   2340
```

```
cgtgaccgcc gccgggatca ctctcggcat ggacgagctg tacaagtaaa gcggccgcga    2400
ctctagagtc ggggcggccg gccgcttcga gcagacatga taagatacat tgatgagttt    2460
ggacaaacca caactagaat gcagtgaaaa aaatgcttta tttgtgaaat tgtgatgct     2520 attgctttat ttgtaaccat tataagctgc aataaacaag ttaacaacaa caattgcatt    2580
cattttatgt ttcaggttca gggggaggtg tgggaggttt tttaaagcaa gtaaaacctc    2640
tacaaatgtg gtaaaatcga taaggatcct gctggtatgc ctagccctgg tgctgccagc    2700
ctcggagaca aactgtaagt aatccatacc tcctggcttc tccattccct atgtgccccg    2760
gcttgaagat tttccactag gctgtttgct gcctcctaag tttccagtaa gtccgccacc    2820
attcagagag tcgcggcagc ctgggtctgg tgggcagtgt aaaggtggga caggatcaaa    2880
gcttgccttg ctttgagaac cattgtccac aggacttgat tccagaaccc gggtgacact    2940
aagtgtcaaa ggaattgctt gaacatagtc ctaaatattg ctaggaaagc taagtcaagc    3000
ctgttgccct cctcccgttt acaagagtgc cccagcccgc accctctcct gcggctaacc    3060
ttccttttgc aatttctgga ctttgaactt gattgactgg tctcacattg acaaactgtt    3120
tggggactgc tggggtgtta catatgattc tctaaccttg atataagaaa tagctgttgg    3180
atgttacctt gtaccgagga tcattttctg agggttttga ctgttgccgc tttgagatgg    3240
cagcaagaat tctgtacaac acacacattt ttgtgtttct tggtctttcc tcttcccatt    3300
ctcagattcc gggcagtata tcgagttttc tcttagaaat ataaacgaa ccacaaggtt     3360 ttagtacatt ttaatggtca attaaattgt ttttagaagc ttaaatatgt tcataattaa    3420
cactgctttc ttttgctctt tgtagtccc agtcactggc atgggagcaa taactgtata     3480
acaaatacca cttaggtcac tgcgagcacc aaagaaactt ttcaaagatg gtaattaagt    3540
aggagtttgc tggaattgca gttttttatt aattagtaag gaatctagcc tgatattttt    3600
aaatgtctaa ctaagttaaa gaccagaatg aaactggttc acttttatt gaggataaac     3660 aagttacagt tataaagcct caacaatcaa agccctacga tgaagcagcg tgtgactgta    3720
tgcacatgat ctatcttgtt cagaggaaca atcaaacatt ttcagatagc atcagggcgg    3780
tggtggtact cgcctataat cctagcaaag tcagaggcaa gcagatctct gtgttcaagg    3840
ccagcctagt ctacagagtg agttccagga caactggggc tacacagaga aacctgtctc    3900
agagaaaaac aaaataaaac caaattcaga tagctggtgt ttgggaaaag agcaaaagac    3960
agcagtgctg gccacacaga gagtagacaa gttcattcta caaggacatc acagaaagaa    4020
tatgtgaccc aatgacgacc ataaactttc ttgttcctgt gtcaaattat ctccggttta    4080
ttgatgaaga accagacact atgagctgcg tctcctcctt aagattttgt tttggtgtct    4140 tgttttgtc aagggggtttc attgtggccc tgagcattag atccagggct ttgtgcatgc     4200
taggccaggg agctatattc ccgaactcca gaagactagg aatttgagat ataaatagaa    4260
tttgaattac cttctgtaca attgattgta tggttctaga atattgcta tattaaggga     4320 agcctttgca gaagacagtt attttgagat ggtgcataac acaaagaaa tgaactaaag     4380 cctgaggcct gctctgtagc tctgccttgc ccttagccta caataacttt ctttacctt     4440 caagcatgtg ccaccacgcc tgactttcag gcccttcatt ttaacaagaa agcaagtatt    4500
cagttatcaa ctgactttcc aaatgcattt gtatgaataa aaactacaaa aatataaaaa    4560
taagaactat acacacaaaa gccttgtatt taaaatttac gctgtggaca tattttgctc    4620
atcattcgtg agagccttgcg gtaaaaaggc aaagggggaag aggaggatat ctattttggg  4680
taggctaatt tggccttatc cagacttccc ttttgggtgg atgcagtctg cccagcacac    4740
```

```
tattggccca tttcttctac atggctttgt gctctgctct gcccttagct aattgtcccc   4800
tttgacatgc ttttgtcttt ccttaaagtt tctatacttc aaaaaccatc ccgctacact   4860
aatggagtga ttttctcaag ggttgcttta tgtttggggt ttgtactgca agagttagtt   4920
tctgatatag caatggtgat agtatagtct tctaccatga actctatgcc agcaagtaca   4980
ggggtatatt tcacatgggt gttttctgtt cactgagttt catgtcttct ttgtatcttt   5040
ttgttttgtt ttgtgagaca gggtttctct gtagcttttg agtcagtcct ggaacttgct   5100
ggccggcctt gaactcacag agattcacct gcctctgcct cccaagtgct gggatttaag   5160
gtgtgagtca ccactgccag ttttttcttt tgtatcttga gtgaactaaa taggtaagct   5220
ttaaataata atatgagcag tctatttata tacattaaat attaaatgca ttgtgagatg   5280
agcatagcct ttgaggccca ggaacagaaa gatttacttc acattgtaaa tatactggta   5340
tacatacaaa cgtacatacn nnnnngtgtg tgtgtgtgtg tgtgtgtgtg tgtgcatgcc   5400
atagcacaca tgtgaagtcc agagtacagc attctctttt tctacctttc tgtagattct   5460
tgtggtcaga gtcaggtcaa atcaaatcag acagatgcat gtataaaatg ctcttaccca   5520
ctgaaccatc ttgctgcttg gtccacaagc ttagtggaag aatgctggga agtgaatagt   5580 atgttttttaa atgtagttaa ccttgacttt ttgttgttgt tgctgttatt gaggccacat   5640
tttcattgtt ctgagaaaat attactattt tcctcagaca gaattatata tttatttgaa   5700
gttcatgaat tccatattat tttcctgtat ttattacaaa tagcatgctt aaacacttcc   5760
aagtagtgaa acagctgctc atgtaggaca cggattattg acagtgctgc catttatcag   5820
ccagtaatcc acttggcagg tagcacgctc atcgttatcc tttatgcaca caaagccttg   5880
tttgaatttt atcttttaat gagtgtcaat gaaatggaaa gagataagag ttaaaaatac   5940
aacccaaact attgtattta catttctctt ttagaagaaa cctaaagcag cattacttct   6000
tgcccatatt taataaataa catcatttac ccttgttccc tgcctccaga ctctcccata   6060
tactcctctt tcaattttat tggccccttt aaatgacata tcattacatg tatatcccta   6120
cacataagta taaccagttc agtttgtata atgttacttg catgtgtgtt ttcaatgctg   6180
atcatttggt agtggataac caatggtgtg ccctatgaag gggcagagta tttgtatcat   6240
gcttagcatt cctttgtcga ccgatgccct tgagagcctt caacccagtc agctccttcc   6300
ggtgggcgcg gggcatgact atcgtcgccg cacttatgac tgtcttcttt atcatgcaac   6360
tcgtaggaca ggtgccggca gcgctcttcc gcttcctcgc tcactgactc gctgcgctcg   6420
gtcgttcggc tgcggcgagc ggtatcagct cactcaaagg cggtaatacg gttatccaca   6480
gaatcagggg ataacgcagg aaagaacatg tgagcaaaag gccagcaaaa ggccaggaac   6540
cgtaaaaagg ccgcgttgct ggcgtttttc cataggctcc gcccccctga cgagcatcac   6600
aaaaatcgac gctcaagtca gaggtggcga aacccgacag gactataaag ataccaggcg   6660
tttccccctg gaagctccct cgtgcgctct cctgttccga ccctgccgct taccggatac   6720
ctgtccgcct ttctcccttc gggaagcgtg gcgctttctc atagctcacg ctgtaggtat   6780
ctcagttcgg tgtaggtcgt tcgctccaag ctgggctgtg tgcacgaacc cccgttcag   6840 cccgaccgct gcgccttatc cggtaactat cgtcttgagt ccaacccggt aagacacgac   6900
ttatcgccac tggcagcagc cactggtaac aggattagca gagcgaggta tgtaggcggt   6960
gctacagagt tcttgaagtg gtggcctaac tacggctaca ctagaagaac agtatttggt   7020
atctgcgctc tgctgaagcc agttaccttc ggaaaaagag ttggtagctc ttgatccggc   7080
aaacaaacca ccgctggtag cggtggtttt tttgtttgca agcagcagat tacgcgcaga   7140
```

```
aaaaaaggat ctcaagaaga tcctttgatc ttttctacgg ggtctgacgc tcagtggaac    7200
gaaaactcac gttaagggat tttggtcatg agattatcaa aaaggatctt cacctagatc    7260
cttttaaatt aaaaatgaag ttttaaatca atctaaagta tatatgagta aacttggtct    7320
gacagttacc aatgcttaat cagtgaggca cctatctcag cgatctgtct atttcgttca    7380
tccatagttg cctgactccc cgtcgtgtag ataactacga tacggagggg cttaccatct    7440
ggccccagtg ctgcaatgat accgcgagac ccacgctcac cggctccaga tttatcagca    7500
ataaaccagc cagccggaag ggccgagcgc agaagtggtc ctgcaacttt atccgcctcc    7560
atccagtcta ttaattgttg ccgggaagct agagtaagta gttcgccagt taatagtttg    7620
cgcaacgttg ttgccattgc tacaggcatc gtggtgtcac gctcgtcgtt tggtatggct    7680
tcattcagct ccggttccca acgatcaagg cgagttacat gatccccat gttgtgcaaa    7740 aaagcggtta gctccttcgg tcctccgatc gttgtcagaa gtaagttggc cgcagtgtta    7800
tcactcatgg ttatggcagc actgcataat tctcttactg tcatgccatc cgtaagatgc    7860
ttttctgtga ctggtgagta ctcaaccaag tcattctgag aatagtgtat gcggcgaccg    7920
agttgctctt gcccggcgtc aatacgggat aataccgcgc cacatagcag aactttaaaa    7980
gtgctcatca ttggaaaacg ttcttcgggg cgaaaactct caaggatctt accgctgttg    8040
agatccagtt cgatgtaacc cactcgtgca cccaactgat cttcagcatc ttttactttc    8100
accagcgttt ctgggtgagc aaaaacagga aggcaaaatg ccgcaaaaaa gggaataagg    8160
gcgacacgga aatgttgaat actcatactc ttcctttttc aatattattg aagcatttat    8220
cagggttatt gtctcatgag cggatacata tttgaatgta tttagaaaaa taaacaaata    8280
ggggttccgc gcacatttcc ccgaaaagtg ccacctgacg cgccctgtag cggcgcatta    8340
agcgcggcgg gtgtggtggt tacgcgcagc gtgaccgcta cacttgccag cgccctagcg    8400
cccgctcctt tcgctttctt cccttccttt ctcgccacgt tcgccggctt tccccgtcaa    8460
gctctaaatc gggggctccc tttagggttc cgatttagtg ctttacggca cctcgacccc    8520
aaaaaacttg attagggtga tggttcacgt agtgggccat cgccctgata gacggttttt    8580
cgccctttga cgttggagtc cacgttcttt aatagtggac tcttgttcca aactggaaca    8640
acactcaacc ctatctcggt ctattctttt gatttataag ggattttgcc gatttcggcc    8700
tattggttaa aaaatgagct gatttaacaa aaatttaacg cgaattttaa caaaatatta    8760
acgcttacaa tttgccattc gccattcagg ctgcgcaact gttgggaagg gcgatcggtg    8820
cgggcctctt cgctattacg ccagcccaag ctaccatgat aagtaagtaa tattaaggta    8880
cgggaggtac ttggagcggc cgcaataaaa tatctttatt ttcattacat ctgtgtgttg    8940
gttttttgtg tgaatcgata gtactaacat acgctctcca tcaaaacaaa acgaaacaaa    9000
acaaactagc aaaataggct gtccccagtg caagtgcagg tgccagaaca tttctctatc    9060
gata                                                                9064
```